(12) United States Patent
Blanchetot et al.

(10) Patent No.: US 11,649,295 B2
(45) Date of Patent: May 16, 2023

(54) ASYMMETRIC MULTISPECIFIC ANTIBODIES

(71) Applicant: argenx BV, Ghent (BE)

(72) Inventors: Christophe Frederic Jerome Blanchetot, Destelbergen (BE); Johannes Joseph Wilhelmus De Haard, Oudelande (NL)

(73) Assignee: argenx BV, Ghent (BE)

( * ) Notice: Subject to any disclaimer, the term of this patent is extended or adjusted under 35 U.S.C. 154(b) by 621 days.

(21) Appl. No.: 16/599,883

(22) Filed: Oct. 11, 2019

(65) Prior Publication Data

US 2020/0157248 A1 May 21, 2020

Related U.S. Application Data

(62) Division of application No. 15/503,602, filed as application No. PCT/EP2015/069186 on Aug. 20, 2015, now Pat. No. 10,487,156.

(30) Foreign Application Priority Data

Aug. 20, 2014 (GB) .................................... 1414823

(51) Int. Cl.
   *C07K 16/46* (2006.01)
   *C07K 16/42* (2006.01)
   *C07K 1/22* (2006.01)

(52) U.S. Cl.
   CPC .............. *C07K 16/468* (2013.01); *C07K 1/22* (2013.01); *C07K 16/42* (2013.01); *C07K 2317/22* (2013.01); *C07K 2317/31* (2013.01); *C07K 2317/51* (2013.01); *C07K 2317/515* (2013.01); *C07K 2317/52* (2013.01); *C07K 2317/522* (2013.01); *C07K 2317/526* (2013.01); *C07K 2317/569* (2013.01); *C07K 2317/64* (2013.01)

(58) Field of Classification Search
   CPC ........ C07K 16/468; C07K 1/22; C07K 16/42; C07K 2317/22; C07K 2317/31; C07K 2317/51; C07K 2317/515; C07K 2317/52; C07K 2317/522; C07K 2317/526; C07K 2317/569; C07K 2317/64
   See application file for complete search history.

(56) References Cited

U.S. PATENT DOCUMENTS

| | | | | |
|---|---|---|---|---|
| 10,047,163 | B2 * | 8/2018 | Liu | .................... C07K 16/2803 |
| 2009/0182127 | A1 * | 7/2009 | Kjaergaard | ........ C07K 16/2803 |
| | | | | 530/387.3 |
| 2013/0178605 | A1 | 7/2013 | Blein | |

FOREIGN PATENT DOCUMENTS

| | | |
|---|---|---|
| WO | WO 2007/024715 A2 | 3/2007 |
| WO | WO 2011/080350 A1 | 7/2011 |
| WO | WO 2012/023053 A2 | 2/2012 |
| WO | WO 2013/064701 A2 | 5/2013 |
| WO | WO 2013/088259 A2 | 6/2013 |
| WO | WO 2013/124451 A1 | 8/2013 |
| WO | WO 2013/136186 A2 | 9/2013 |
| WO | WO 2014/124326 A1 | 8/2014 |

OTHER PUBLICATIONS

Lloyd et al. Protein Engineering, Design & Selection 22:159-168 (Year: 2009).*
Edwards et al., J Mol Biol. 334(1): 103-118 (Year: 2003).*
Piche-Nicholas et al MABS 10(1): 81-94 (Year: 2018).*
Yu et all., Investigative Ophthalmology & Visual Science 49(2): 522-527 (Year: 2008).*
Poosarla et al., Biotechn. Bioeng. 114(6): 1331-1342 (Year: 2017).*
International Search Report with Written Opinion corresponding to International Patent Application No. PCT/EP2015/069186, dated Jan. 20, 2016.
Klein et al. (Nov. 1, 2012) "Progress in Overcoming the Chain Association Issue in Bispecific Heterodimeric IgG Antibodies", mAbs. 4(6):653-663.
MacCallum et al., (Oct. 11, 1996) "Antibody-Antigen Interactions: Contact Analysis and Binding Site Topography", Journal of Molecular Biology 262(5): 732-745.
Pascalis et al., (Sep. 15, 2002) "Grafting of 'Abbreviated' Complementarity-Determining Regions Containing Specificity-Determining Residues Essential for Ligand Contact to Engineer a Less Immunogenic Humanized Monoclonal Antibody", Journal of Immunology 169(6): 3076-3084.
Vidarsson et al. (Oct. 20, 2014) "IgG Subclasses and Allotypes: From Structure to Effector Functions", Front. Immunol. 5: 520 doi: 10.3389/fimmu.2014.00520.
Wu et al., (Nov. 19, 1999) "Humanization of a Murine Monoclonal Antibody by Simultaneous Optimization of Framework and CDR Residues", Journal of Molecular Biology 294(1): 151-162.

* cited by examiner

*Primary Examiner* — Phuong Huynh
(74) *Attorney, Agent, or Firm* — Dechert LLP; Andrew T Wilkins; Victoria E. Pedanou

(57) ABSTRACT

The present invention relates to multispecific antibodies, for example bispecific antibodies, and methods for the isolation or purification of the same. The antibodies of the invention comprise first and second heavy chain-light chain pairings wherein each pairing comprises a distinct selective recognition site including one or more amino acid residues contributed from the heavy chain and the light chain of the pairing. The first and second selective recognition sites differ by at least one amino acid residue and can be differentially bound by first and second selective recognition agents according to the methods of the invention. Such methods facilitate the production of antibody preparations enriched for multispecific antibodies having the correct functional heavy chain-light chain pairings.

16 Claims, 11 Drawing Sheets

Specification includes a Sequence Listing.

```
             1       --PKANPTVTLFPPSSEELQANKATLVCLISDFYPGAVTVAWKADGSPVKAGVETTKPSKQSNNKYAASSYLSLTPEQWKSHRSYSCQVTHEGSTVEKTVAPTECS
IGLC1*01     1       --PKANPTVTLFPPSSEELQANKATLVCLISDFYPGAVTVAWKADGSPVKAGVETTKPSKQSNNKYAASSYLSLTPEQWKSHRSYSCQVTHEGSTVEKTVAPTECS
IGLC2*01     1       GQ..A.S.............................................S..........T..................................
IGLC3*01     1       -..A.S..............................................S.........T..................................
IGLC6*01     1       GQ..A.S.........................V...........K......NT........I......K...........................A..
IGLC7*01     1       GQ..A.S...............................................V.......I...........R.....................A..
```

A

B

SEQUENCE LISTING

<160> NUMBER OF SEQ ID NOS: 19

<210> SEQ ID NO 1
<211> LENGTH: 98
<212> TYPE: PRT
<213> ORGANISM: Homo sapiens

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 2
<211> LENGTH: 98
<212> TYPE: PRT
<213> ORGANISM: Homo sapiens

<400> SEQUENCE: 2

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val

<210> SEQ ID NO 3
<211> LENGTH: 101
<212> TYPE: PRT
<213> ORGANISM: Homo sapiens

<400> SEQUENCE: 3

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr

```
                65                  70                  75                  80
Tyr Thr Cys Asn Val Asp His Lys Pro Ser Asn Thr Lys Val Asp Lys
                    85                  90                  95
Thr Val Glu Arg Lys
            100

<210> SEQ ID NO 4
<211> LENGTH: 101
<212> TYPE: PRT
<213> ORGANISM: Homo sapiens

<400> SEQUENCE: 4

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Thr Ser Ser Asn Phe Gly Thr Gln Thr
65                  70                  75                  80
Tyr Thr Cys Asn Val Asp His Lys Pro Ser Asn Thr Lys Val Asp Lys
                    85                  90                  95
Thr Val Glu Arg Lys
            100

<210> SEQ ID NO 5
<211> LENGTH: 101
<212> TYPE: PRT
<213> ORGANISM: Homo sapiens

<400> SEQUENCE: 5

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Ser Leu Gly Thr Gln Thr
65                  70                  75                  80
Tyr Thr Cys Asn Val Asp His Lys Pro Ser Asn Thr Lys Val Asp Lys
                    85                  90                  95
Thr Val Glu Arg Lys
            100

<210> SEQ ID NO 6
<211> LENGTH: 101
<212> TYPE: PRT
<213> ORGANISM: Homo sapiens

<400> SEQUENCE: 6

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
                20                  25                  30
```

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys
            100

<210> SEQ ID NO 7
<211> LENGTH: 110
<212> TYPE: PRT
<213> ORGANISM: Homo sapiens

<400> SEQUENCE: 7

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr
            100                 105                 110

<210> SEQ ID NO 8
<211> LENGTH: 110
<212> TYPE: PRT
<213> ORGANISM: Homo sapiens

<400> SEQUENCE: 8

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr
            100                 105                 110

<210> SEQ ID NO 9
<211> LENGTH: 110
<212> TYPE: PRT
<213> ORGANISM: Homo sapiens
```

<400> SEQUENCE: 9

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Tyr Ser Gly Leu Tyr Ser
        50                  55                  60

Leu Ser Ser Val Val Thr Val Pro Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr
            100                 105                 110

<210> SEQ ID NO 10
<211> LENGTH: 104
<212> TYPE: PRT
<213> ORGANISM: Homo sapiens

<400> SEQUENCE: 10

Pro Lys Ala Asn Pro Thr Val Thr Leu Phe Pro Pro Ser Ser Glu Glu
1               5                   10                  15

Leu Gln Ala Asn Lys Ala Thr Leu Val Cys Leu Ile Ser Asp Phe Tyr
                20                  25                  30

Pro Gly Ala Val Thr Val Ala Trp Lys Ala Asp Gly Ser Pro Val Lys
            35                  40                  45

Ala Gly Val Glu Thr Thr Lys Pro Ser Lys Gln Ser Asn Asn Lys Tyr
        50                  55                  60

Ala Ala Ser Ser Tyr Leu Ser Leu Thr Pro Glu Gln Trp Lys Ser His
65                  70                  75                  80

Arg Ser Tyr Ser Cys Gln Val Thr His Glu Gly Ser Thr Val Glu Lys
                85                  90                  95

Thr Val Ala Pro Thr Glu Cys Ser
            100

<210> SEQ ID NO 11
<211> LENGTH: 106
<212> TYPE: PRT
<213> ORGANISM: Homo sapiens

<400> SEQUENCE: 11

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
        50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 12
<211> LENGTH: 105
<212> TYPE: PRT
<213> ORGANISM: Homo sapiens

<400> SEQUENCE: 12

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 13
<211> LENGTH: 106
<212> TYPE: PRT
<213> ORGANISM: Homo sapiens

<400> SEQUENCE: 13

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Val Ser Asp
            20                  25                  30

Phe Tyr Pro Gly Ala Val Thr Val Ala Trp Lys Ala Asp Gly Ser Pro
        35                  40                  45

Val Lys Val Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Arg Val Thr His Glu Gly Ser Thr Val
                85                  90                  95

Glu Lys Thr Val Ala Pro Ala Glu Cys Ser
            100                 105

<210> SEQ ID NO 14
<211> LENGTH: 106
<212> TYPE: PRT
<213> ORGANISM: Homo sapiens

<400> SEQUENCE: 14

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Lys Val Ala Trp Lys Ala Asp Gly Ser Pro
        35                  40                  45

Val Asn Thr Gly Val Glu Thr Thr Thr Pro Ser Lys Gln Ser Asn Asn

```
                    50                  55                  60
Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                     85                  90                  95

Glu Lys Thr Val Ala Pro Ala Glu Cys Ser
                100                 105
```

<210> SEQ ID NO 15
<211> LENGTH: 116
<212> TYPE: PRT
<213> ORGANISM: Llama glama

<400> SEQUENCE: 15

```
Glu Val Gln Leu Val Glu Ser Gly Gly Gly Leu Val Arg Ala Gly Gly
 1               5                  10                  15

Ser Leu Arg Leu Ser Cys Ala Ala Ser Gly Ser Ile Phe Gly Thr Thr
                20                  25                  30

Asn Met Gly Trp Tyr Arg Gln Ala Pro Gly Thr Gln Arg Asp Leu Val
                35                  40                  45

Ala Thr Ile Asn Asn Gly Gly Ile Thr Asn Tyr Ala Asp Ser Val Lys
 50                  55                  60

Gly Arg Phe Thr Ile Ser Thr Asp Tyr Thr Lys Asn Thr Val Tyr Leu
 65                  70                  75                  80

Gln Met Asp Arg Leu Lys Pro Glu Asp Thr Ala Val Tyr Tyr Cys Asn
                85                  90                  95

Ala Glu Tyr His Phe Arg Pro Pro Ser Trp Gly Gln Gly Thr Gln Val
                100                 105                 110

Thr Val Ser Ser
        115
```

<210> SEQ ID NO 16
<211> LENGTH: 120
<212> TYPE: PRT
<213> ORGANISM: Llama glama

<400> SEQUENCE: 16

```
Gln Val Gln Leu Val Glu Ser Gly Gly Gly Leu Val Gln Pro Gly Gly
 1               5                  10                  15

Ser Leu Arg Leu Ser Cys Arg Ala Ser Gly Ala Ile Phe Ser Ile Asn
                20                  25                  30

His Met Gly Trp Tyr Arg Gln Ala Pro Gly Lys Gln Arg Glu Leu Val
                35                  40                  45

Ala Thr Ile Thr Ser Gly Gly Ser Thr Asn Tyr Ala Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Ser Cys Asn
                85                  90                  95

Leu Asp Trp Thr Thr Gly Trp Gly Ser Arg Arg Asp Tyr Trp Gly Gln
                100                 105                 110

Gly Thr Gln Val Thr Val Ser Ser
        115                 120
```

<210> SEQ ID NO 17
<211> LENGTH: 124
<212> TYPE: PRT

<213> ORGANISM: Llama glama

<400> SEQUENCE: 17

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Asp Ile Tyr
            20                  25                  30

Thr Met Gly Trp Phe Arg Gln Val Pro Gly Lys Glu Arg Glu Phe Val
        35                  40                  45

Ala Asp Ile Gly Arg Ala Gly Gly Thr Thr His Tyr Ala Asp Ser Val
    50                  55                  60

Lys Gly Arg Phe Ala Ile Ser Arg Asp Asn Ala Asn Asp Ala Val His
65                  70                  75                  80

Leu Gln Met Asn Ser Leu Lys Pro Glu Asp Thr Ala Val Tyr Tyr Cys
                85                  90                  95

Ala Thr Lys Val Val Pro Arg Ala Gly Arg Arg Leu Leu Asp Tyr Asp
            100                 105                 110

Tyr Trp Gly Gln Gly Thr Gln Val Thr Val Ser Ser
        115                 120

<210> SEQ ID NO 18
<211> LENGTH: 120
<212> TYPE: PRT
<213> ORGANISM: Llama glama

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Arg Ala Ser Gly Ala Ile Phe Ser Ile Asn
            20                  25                  30

His Met Gly Trp Tyr Arg Gln Ala Pro Gly Lys Gln Arg Glu Leu Val
        35                  40                  45

Ala Thr Ile Thr Ser Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Ser Cys Asn
                85                  90                  95

Leu Asp Trp Thr Thr Gly Trp Gly Ser Arg Arg Asp Tyr Trp Gly Gln
            100                 105                 110

Gly Thr Gln Val Thr Val Ser Ser
        115                 120

<210> SEQ ID NO 19
<211> LENGTH: 120
<212> TYPE: PRT
<213> ORGANISM: Llama glama

<400> SEQUENCE: 19

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Arg Tyr
            20                  25                  30

Gly Met Ser Trp Phe Arg Gln Ala Pro Gly Lys Glu Arg Glu Phe Val
        35                  40                  45

Ala Thr Ile Ser Arg Gly Gly Ser Ser Thr Asn Tyr Ala Asp Ser Thr
    50                  55                  60

```
Lys Gly Arg Phe Thr Val Ser Arg Asp Asn Ala Lys Asn Thr Val Val
 65              70                  75                  80

Leu Gln Met Asn Ser Leu Lys Pro Glu Asp Thr Ala Val Tyr Tyr Cys
                 85                  90                  95

Ala Ala Asp Thr Asn Trp Pro Val Gly Ala Tyr Glu Tyr Trp Gly Gln
            100                 105                 110

Gly Thr Gln Val Thr Val Ser Ser
        115             120
```

ASYMMETRIC MULTISPECIFIC ANTIBODIES

CROSS-REFERENCE TO RELATED APPLICATIONS

This application is a divisional of U.S. patent application Ser. No. 15/503,602, filed Aug. 18, 2017, now U.S. Pat. No. 10,487,156, which is a 35 U.S.C. § 371 filing of International Patent Application No. PCT/EP2015/069186, filed Aug. 20, 2015, which claims priority to United Kingdom Patent Application No. 1414823.3, filed Aug. 20, 2014, the entire disclosures of which are hereby incorporated herein by reference.

FIELD OF THE INVENTION

The present invention relates to multispecific antibodies, for example bispecific antibodies, and methods for the isolation or purification of the same. The antibodies and methods of the invention facilitate the production of antibody preparations enriched for multispecific antibodies having the correct functional heavy chain-light chain pairings required for the antibody to bind two or more epitopes on the same antigen or different antigens.

BACKGROUND TO THE INVENTION

Naturally occurring antibodies, including bivalent antibodies, exhibit immunoreactivity to a specific epitope on a particular target antigen. Multispecific antibodies, as the name indicates, are antibodies engineered to recognise and bind more than one epitope, potentially on different target antigens of interest.

Naturally occurring antibodies typically include combinations of heavy and light immunoglobulin chains, wherein the antigen binding properties of the molecule are determined by the variable regions or domains of the heavy and light chains i.e. the VH and VL domains, respectively. More specifically, the antigen binding sites of any antibody typically include residues contributed by three complementarity determining regions (CDRs) within each of the VH and VL domains.

Multispecific antibodies differ from naturally occurring antibodies in that they incorporate more than one VH-VL domain pairing such that they can recognise and bind to more than one epitope. Commercially these antibodies are extremely important for their ability to bind more than one target antigen. However, significant difficulties exist in the manufacture and isolation of multispecific antibodies as a result of mispairings between the different heavy chains and light chains incorporated into the same antibody molecule. These mispairings can lead to the inadvertent production of monospecific antibodies or antibodies having non-functional or non-productive antigen binding sites, thereby reducing the yield of the multispecific antibody of interest.

FIG. 1 illustrates the difficulties that can arise in the production of a bispecific antibody exhibiting immunoreactivity for two distinct epitopes. The bispecific antibody as shown (A) includes two distinct heavy chains and two distinct light chains. However, only the correct pairing of these four immunoglobulin chains gives rise to an antibody having the required binding profile i.e. specificity for both target antigens. There are in fact nine other potential combinations that can form from a mixture of the four heavy and light chains shown, which result in bivalent monospecific antibodies (E and H), monovalent monospecific antibodies (B, C, G and J) and non-binding antibodies (D, F and I). This problem becomes worse the more complex the multispecific antibody molecule i.e. the more epitopes or antigens the antibody is intended to bind.

Various attempts have been made to improve multispecific antibody production by addressing the problem of incorrect chain pairing. Several approaches have focussed on engineering antibodies so as to promote the correct pairing between VH-VL domains. For instance, US2010/0254989A1 describes the construction of bispecific cMet-ErbB1 antibodies, where the VH and VL of the individual antibodies are fused genetically via a GlySer linker. An alternative approach uses rat-mouse quadromas for generating bispecific antibodies, where the mouse and the rat antibody predominantly forms the original VH-VL pairings and the bispecific antibody consists of the rat and the mouse Fc (Lindhofer et al., J Immunol. (1995) 155: 1246-1252).

For bispecific antibodies including an Fc domain, researchers have also focussed on introducing mutations into the constant region of the heavy chains to promote the correct heterodimerization of the Fc portion. Several such techniques are reviewed in Klein et al. (mAbs (2012) 4:6, 1-11), the contents of which are incorporated herein by reference in their entirety. These techniques include the "knobs-into-holes" (KiH) approach which involves the introduction of a bulky residue into one of the CH3 domains of one of the antibody heavy chains. This bulky residue fits into a complementary "hole" in the other CH3 domain of the paired heavy chain so as to promote correct pairing of heavy chains.

Researchers have also attempted to resolve the problem of achieving correct association of heavy chain and light chain pairs. One approach uses the CrossMab principle (as reviewed in Klein et al.), which involves domain swapping between heavy and light chains so as to promote the formation of the correct pairings. Others have sought to engineer the interfaces between the paired VH-VL domains or paired CH1-CL domains of the heavy and light chains so as to increase the affinity between the heavy chain and its cognate light chain (Lewis et al. Nature Biotechnology (2014) 32: 191-198). Techniques such as those described above that require extensive antibody engineering have met with some success; however, the production of antibodies harbouring specific mutations can be labour intensive and can result in antibodies which are highly immunogenic in humans and/or suffer from a loss of effector function.

An alternative approach to the production of multispecific antibody preparations having the correct antigen specificity has been the development of methods that enrich for antibodies having the correct heavy chain-light chain pairings. For example, Spiess et al. (Nature Biotechnology (2013) 31: 753-758) describe a method for the production of a MET-EGFR bispecific antibody from a co-culture of bacteria expressing two distinct half-antibodies. Methods have also been described wherein the constant region of at least one of the heavy chains of a bispecific antibody is mutated so as to alter its binding affinity for an affinity agent, for example Protein A. This allows correctly paired heavy chain heterodimers to be isolated based on a purification technique that exploits the differential binding of the two heavy chains to an affinity agent (see US2010/0331527, WO2013/136186). The limitation with methods that select for correct heavy chain heterodimerization based on differential binding is that they do not select for antibodies having the correct heavy chain-light chain pairings such that these techniques are typically applied to multispecific antibodies having a shared or common light chain.

International patent application no. PCT/EP2012/071866 (WO2013/064701) addresses the problem of incorrect chain pairing using a method for multispecific antibody isolation based on the use of anti-idiotypic binding agents, in particular anti-idiotypic antibodies. The anti-idiotypic binding agents are employed in a two-step selection method in which a first agent is used to capture antibodies having a VH-VL domain pairing specific for a first antigen and a second agent is subsequently used to capture antibodies also having a second VH-VL domain pairing specific for a second antigen.

The drawback with this method is that the anti-idiotypic binding agents used to isolate the antibody must be specific for each multispecific antibody produced, depending on its antigen binding profile. Therefore, although the principle of the method described in PCT/EP2012/071866 is generally applicable to the isolation of any multispecific antibody, the reagents i.e. the anti-idiotypic binding agents, must be generated in accordance with the specific VH-VL domain pairings of the multispecific antibody to be isolated.

SUMMARY OF INVENTION

The present invention improves upon the state of the art by providing multispecific antibodies having at least two distinct heavy chain-light chain pairings wherein the pairings can be distinguished by the presence of selective recognition sites. Each selective recognition site comprises residues contributed by both the heavy and light chain of the pairing, but does not include residues located within the antigen binding site.

In a first aspect, the present invention provides a multispecific antibody comprising
(i) a first pairing comprising a first heavy chain paired with a first light chain, wherein the first pairing comprises a first antigen binding site; and
(ii) a second pairing comprising a second heavy chain paired with a second light chain wherein the second pairing comprises a second antigen binding site,
characterised in that the first pairing comprises a first selective recognition site comprising at least one amino acid residue from the first heavy chain and at least one amino acid residue from the first light chain and the second pairing comprises a second selective recognition site comprising at least one amino acid residue from the second heavy chain and at least one amino acid residue from the second light chain, wherein the first and second selective recognition sites do not include residues from the antigen binding site of the first or second pairing,
and wherein the combination of amino acid residues of the first selective recognition site differs by at least one amino acid residue from the combination of amino acid residues of the second selective recognition site such that the first and second selective recognition sites can be differentially bound by first and second selective recognition agents.

The present invention also provides multispecific antibodies having at least two distinct heavy chain-light chain pairings wherein the first and second heavy chains differ by at least one amino acid residue in the constant region, preferably in the CH1 domain. The first and second heavy chains can differ because each chain comprises a fragment derived from the constant region of a different human immunoglobulin subtype or a different allotype, preferably different human allotypes. In certain embodiments, the first and second heavy chains comprise the entire constant region from different human immunoglobulin subtypes or different allotypes, wherein the constant regions differ by at least one amino acid residue in the CH1 domain. These differences can be exploited such that multispecific antibodies having the correct heavy chain-light chain pairings can be identified and purified.

Thus, provided herein is a multispecific antibody comprising
(i) a first pairing comprising a first heavy chain paired with a first light chain, wherein the first pairing comprises a first antigen binding site; and
(ii) a second pairing comprising a second heavy chain paired with a second light chain wherein the second pairing comprises a second antigen binding site,
characterised in that the first and second heavy chain each comprise a fragment derived from the constant region of a different human immunoglobulin subtype, wherein the fragments differ by at least one amino acid residue.

Further provided is a multispecific antibody comprising
(i) a first pairing comprising a first heavy chain paired with a first light chain, wherein the first pairing comprises a first antigen binding site; and
(ii) a second pairing comprising a second heavy chain paired with a second light chain wherein the second pairing comprises a second antigen binding site,
characterised in that the first and second heavy chain each comprise a fragment derived from the constant region of a different immunoglobulin allotype, wherein the fragments differ by at least one amino acid residue.

Preferably, the fragments derived from the constant region of the different human immunoglobulin subtypes or the different allotypes comprise or consist of the CH1 domain.

Multispecific antibodies of the present invention can be isolated according to the methods provided herein. These methods exploit the variation that can be found in immunoglobulin heavy and light chains outside of the antigen binding site, and in particular, the natural variation found in the constant regions of heavy chain-light chain pairings, so as to produce multispecific antibody preparations enriched for antibodies having the correct functional VH-VL pairings required for target antigen recognition and binding.

The methods of the present invention achieve isolation and/or purification of multispecific antibodies using selective recognition agents that recognise the selective recognition sites within the distinct immunoglobulin heavy chain-light chain pairings. The fact that the methods of the invention are based on the selective binding of agents to regions of the antibody outside the antigen binding sites, means that the methods are broadly applicable to the purification of multispecific antibodies irrespective of the epitopes or antigens to which the antibody is designed to bind.

In a further aspect, the present invention provides a method for the isolation of a multispecific antibody according to the first aspect of the invention from a sample, said method comprising:
a. contacting the sample with a first selective recognition agent which selectively binds to the first selective recognition site;
b. releasing any antibodies bound to the first selective recognition agent to obtain a second sample containing antibodies having the first heavy chain-light chain pairing;
c. contacting the second sample with a second selective recognition agent which selectively binds to the second selective recognition site;

d. releasing any antibodies bound to the second selective recognition agent thereby obtaining a preparation of antibodies having both first and second heavy chain-light chain pairings.

The invention also relates to reagents and kits for producing multispecific antibodies according to the invention, and also reagents, particularly antibodies, and kits for isolating multispecific antibodies using the methods of the invention.

In a further aspect, the present invention provides an antibody or antigen binding fragment thereof that binds to a multispecific antibody according to any of the preceding aspects of the invention, wherein the antibody or antigen binding fragment thereof binds to an epitope, wherein the epitope is:
(i) comprised within the first pairing (the first heavy chain paired with the first light chain) but not the second pairing (the second heavy chain paired with the second light chain); or
(ii) comprised within the second pairing (the second heavy chain paired with the second light chain) but not the first pairing (the first heavy chain paired with the first light chain) and wherein the epitope does not include residues from the antigen binding site.

In a further aspect, the present invention provides a kit for producing a multispecific antibody according to the first aspect of the invention comprising one or more polynucleotides, wherein the polynucleotide(s) encode(s) fragments of the first and second heavy chains and fragments of the first and second light chains wherein the fragments contain at least the residues of the first and second selective recognition sites. Also provided herein is a kit for isolating a multispecific antibody according to the method aspect of the invention wherein the kit comprises a first selective recognition agent and a second selective recognition agent. Further provided is a kit for producing and isolating a multispecific antibody of the present invention wherein the kit comprises:
(i) one or more polynucleotides, wherein the polynucleotide(s) encode(s) fragments of the first and second heavy chains and fragments of the first and second light chains wherein the fragments contain at least the residues of the first and second selective recognition sites; and
(ii) a first selective recognition agent and a second selective recognition agent wherein the first and second selective recognition agents can selectively bind the first and second selective recognition sites within the fragments encoded by the one or more polynucleotides of (i).

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF DRAWINGS

FIG. 3 Alignment of CH1 domains derived from human IgG heavy chain subtypes and allotypes demonstrating sequence variation between different allotypes. Sequences, from top to bottom, correspond to SEQ ID NOs: 1-9, respectively.

FIG. 5 Alignment of CL domains derived from human lambda chain allotypes demonstrating sequence variation between different allotypes. Sequences, from top to bottom, correspond to SEQ ID NOs: 10, 11, 12, 14, and 13, respectively.

DETAILED DESCRIPTION

A. Definitions

"Antibody" and "Immunoglobulin"

Figure 1:
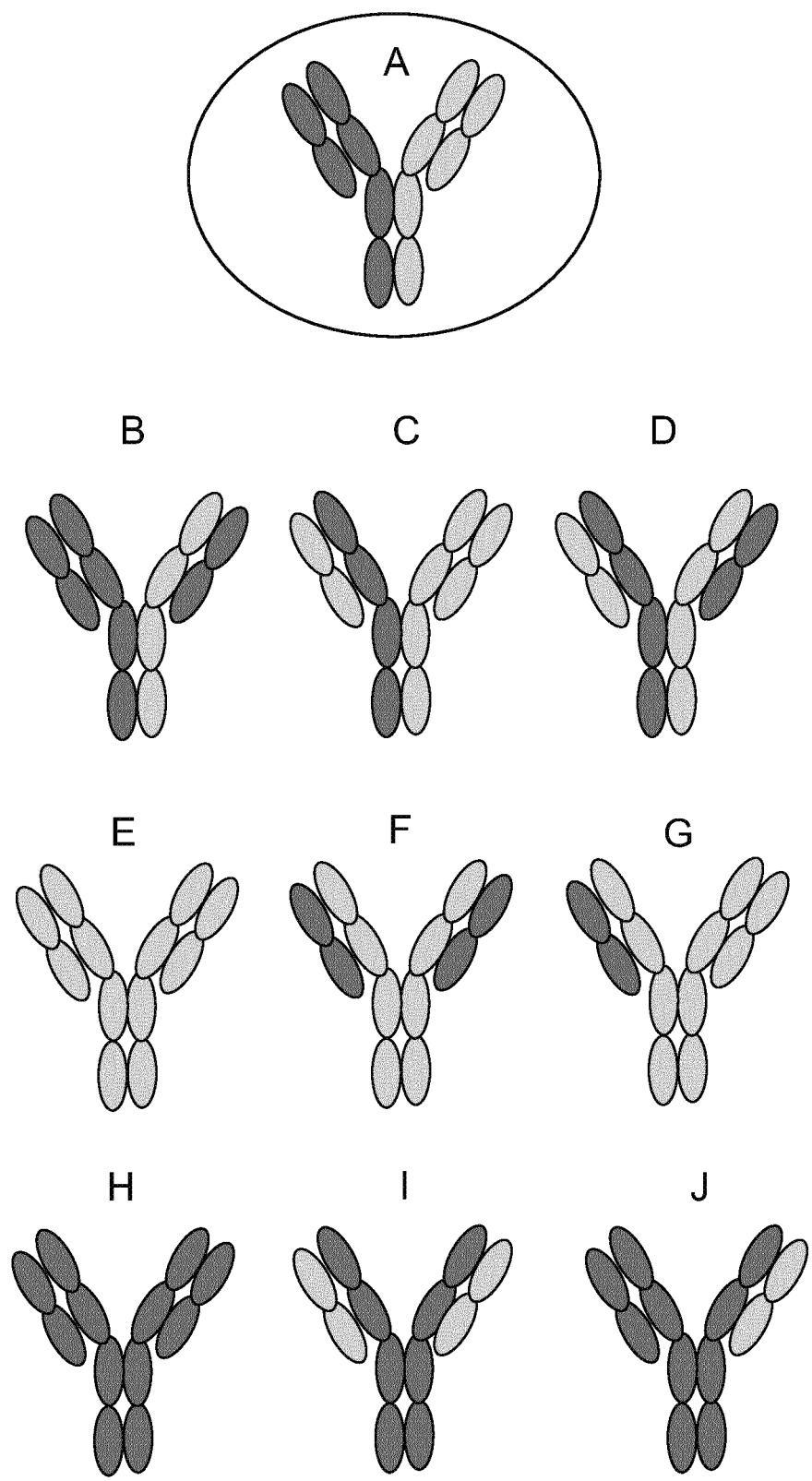
FIG. 1 shows the ten different pairings of heavy and light chain combinations that can result from the production of a bispecific antibody having two distinct heavy chains and two distinct light chains.

As used herein, the term "immunoglobulin" includes a molecule having a combination of two heavy chains and two light chains. An "antibody" or "antibody molecule" refers to an immunoglobulin with a specific immunoreactive activity to an antigen of interest (e.g. a human antigen). Antibodies and immunoglobulins comprise light and heavy chains, with or without an interchain covalent linkage between them. Basic immunoglobulin structures in vertebrate systems are relatively well understood.

The generic term "immunoglobulin" comprises five distinct classes of antibody that can be distinguished biochemically. All five classes of antibodies are within the scope of the present invention, although the following discussion will generally be directed to the IgG class of immunoglobulin molecules. Naturally occurring IgG immunoglobulins comprise two identical light polypeptide chains of molecular weight approximately 23,000 Daltons, and two identical heavy polypeptide chains of molecular weight 53,000-70,000. The four chains are joined by disulfide bonds in a "Y" configuration wherein the light chains bracket the heavy chains starting at the mouth of the "Y" and continuing through the variable region (see FIG. 2).

The light chains of an antibody are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells.

In the heavy chain, the amino acid sequence runs from an N-terminus at the forked end of the Y configuration to the C-terminus at the bottom of each chain. Those skilled in the art will appreciate that heavy chains are classified as gamma, mu, alpha, delta, or epsilon, (γ, μ, α, δ, ε) with some subclasses or subtypes among them (e.g., γ1-γ4). It is the nature of this chain that determines the "class" of the antibody as IgG, IgM, IgA, IgD or IgE, respectively. The immunoglobulin subclasses (subtypes or isotypes) e.g., IgG1, IgG2, IgG3, IgG4, IgA1, etc. are well characterized and are known to confer functional specialization. Modified versions of each of these classes and isotypes are readily discernable to the skilled artisan in view of the instant disclosure and, accordingly, are within the scope of the instant invention.

"Variable Region" and "Variable Domains"

The variable region of an antibody is the portion which allows the antibody to selectively recognise and specifically bind epitopes on antigens. The variable region is typically made up of the variable domain of the heavy chain (VH) and the variable domain of the light chain (VL), both domains of which are located at the N terminus of their respective polypeptides (see FIG. 2).

The term "variable" refers to the fact that certain portions of the variable domains VH and VL differ extensively in sequence among antibodies and are used in the binding and specificity of each particular antibody for its target antigen. However, the variability is not evenly distributed throughout the variable domains of antibodies. It is concentrated in three segments called "hypervariable loops" in each of the VL domain and the VH domain which form part of the antigen binding site. The first, second and third hypervariable loops of the VLambda light chain domain may be defined as comprising residues 24-33 (L1(λ), consisting of 9, 10 or 11 amino acid residues), 49-53 (L2(λ), consisting of 3 residues) and 90-96 (L3(λ), consisting of 5 residues) in the VL domain (Morea et al., Methods 20:267-279 (2000)). The first, second and third hypervariable loops of the VKappa light chain domain may be defined as comprising residues 25-33 (L1 (κ), consisting of 6, 7, 8, 11, 12 or 13 residues), 49-53 (L2(κ), consisting of 3 residues) and 90-97 (L3(κ), consisting of 6 residues) in the VL domain (Morea et al., Methods 20:267-279 (2000)). The first, second and third hypervariable loops of the VH domain may be defined as comprising residues 25-33 (H1, consisting of 7, 8 or 9 residues), 52-56 (H2, consisting of 3 or 4 residues) and 91-105 (H3, highly variable in length) in the VH domain (Morea et al., Methods 20:267-279 (2000)).

The hypervariable loops (L1, L2, L3, H1, H2 and H3) may each comprise part of a "complementarity determining region" or "CDR", as defined below. The terms "hypervariable loop" and "complementarity determining region" are not strictly synonymous, since the hypervariable loops (HVs) are defined on the basis of structure, whereas complementarity determining regions (CDRs) are defined based on sequence variability (Kabat et al., Sequences of Proteins of Immunological Interest, 5th Ed. Public Health Service, National Institutes of Health, Bethesda, Md., 1983).

The CDRs of the VL and VH domains can typically be defined as comprising the following amino acids: residues 24-34 (LCDR1), 50-56 (LCDR2) and 89-97 (LCDR3) in the light chain variable domain, and residues 31-35 or 31-35b (HCDR1), 50-65 (HCDR2) and 95-102 (HCDR3) in the heavy chain variable domain; (Kabat et al., Sequences of Proteins of Immunological Interest, 5th Ed. Public Health Service, National Institutes of Health, Bethesda, Md. (1991)). Thus, the HVs may be comprised within the corresponding CDRs and references herein to the "hypervariable loops" of VH and VL domains should be interpreted as also encompassing the corresponding CDRs, and vice versa, unless otherwise indicated.

The more highly conserved portions of variable domains are called the framework region (FR), as defined below. The variable domains of native heavy and light chains each comprise four FRs (FR1, FR2, FR3 and FR4, respectively), largely adopting a β-sheet configuration, connected by the three hypervariable loops. The hypervariable loops in each chain are held together in close proximity by the FRs and, with the hypervariable loops from the other chain, contribute to the formation of the antigen binding site of antibodies. Structural analysis of antibodies revealed the relationship between the sequence and the shape of the binding site formed by the complementarity determining regions (Chothia et al., J. Mol. Biol. 227: 799-817 (1992)); Tramontano et al., J. Mol. Biol, 215:175-182 (1990)). Despite their high sequence variability, five of the six loops adopt just a small repertoire of main-chain conformations, called "canonical structures". These conformations are first of all determined by the length of the loops and secondly by the presence of key residues at certain positions in the loops and in the framework regions that determine the conformation through their packing, hydrogen bonding or the ability to assume unusual main-chain conformations.

"CDR"

As used herein, the term "CDR" or "complementarity determining region" means the non-contiguous antigen binding sites found within the variable region of both heavy and light chain polypeptides. These particular regions have been described by Kabat et al., J. Biol. Chem. 252, 6609-6616 (1977) and Kabat et al., Sequences of protein of immunological interest. (1991), and by Chothia et al., J. Mol. Biol. 196:901-917 (1987) and by MacCallum et al., J. Mol. Biol. 262:732-745 (1996) where the definitions include overlapping or subsets of amino acid residues when compared against each other. The amino acid residues which encompass the CDRs as defined by each of the above cited references are set forth for comparison. Preferably, the term "CDR" is a CDR as defined by Kabat based on sequence comparisons.

TABLE 1

CDR definitions

| | CDR Definitions | | |
|---|---|---|---|
| | Kabat[1] | Chothia[2] | MacCallum[3] |
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra "Framework Region"

The term "framework region" or "FR region" as used herein, includes the amino acid residues that are part of the variable region, but are not part of the CDRs (e.g., using the Kabat definition of CDRs). Therefore, a variable region framework is between about 100-120 amino acids in length but includes only those amino acids outside of the CDRs. For the specific example of a heavy chain variable domain and for the CDRs as defined by Kabat et al., framework region 1 corresponds to the domain of the variable region encompassing amino acids 1-30; framework region 2 corresponds to the domain of the variable region encompassing amino acids 36-49; framework region 3 corresponds to the domain of the variable region encompassing amino acids 66-94, and framework region 4 corresponds to the domain of the variable region from amino acids 103 to the end of the variable region. The framework regions for the light chain are similarly separated by each of the light claim variable region CDRs. Similarly, using the definition of CDRs by Chothia et al. or McCallum et al. the framework region boundaries are separated by the respective CDR termini as described above. In preferred embodiments the CDRs are as defined by Kabat.

The framework regions largely adopt a β-sheet conformation and the CDRs form loops which connect, and in some cases form part of, the β-sheet structure. Thus, these framework regions act to form a scaffold that provides for positioning the six CDRs in correct orientation by inter-chain, non-covalent interactions.

"Antigen Binding Site"

As used herein, the "antigen binding site" is the site within the variable region of the antibody which allows the antibody to selectively recognise and specifically bind epitopes on antigens. In naturally occurring antibodies, the six CDRs present on each monomeric antibody are short, non-contiguous sequences of amino acids that are specifically positioned to form the antigen binding site as the antibody assumes its three dimensional configuration in an aqueous environment. As used herein, "residues from the antigen binding site" correspond to residues located within one or more of the CDRs present in either the VH or VL domain. The antigen binding site formed by the positioned CDRs defines a surface complementary to the epitope on the immunoreactive antigen. This complementary surface promotes the non-covalent binding of the antibody to the immunoreactive antigen epitope. The position of CDRs can be readily identified by one of ordinary skill in the art.

"Epitope"

The term "epitope" refers to a specific arrangement of amino acids located on a peptide or protein to which an antibody or antibody fragment binds. Epitopes often consist of a chemically active surface grouping of molecules such as amino acids or sugar side chains, and have specific three dimensional structural characteristics as well as specific charge characteristics. Epitopes can be linear, i.e., involving binding to a single sequence of amino acids, or conformational, i.e., involving binding to two or more sequences of amino acids in various regions of the antigen that may not necessarily be contiguous.

"Constant Region" and "Constant Domains"

Figure 2:
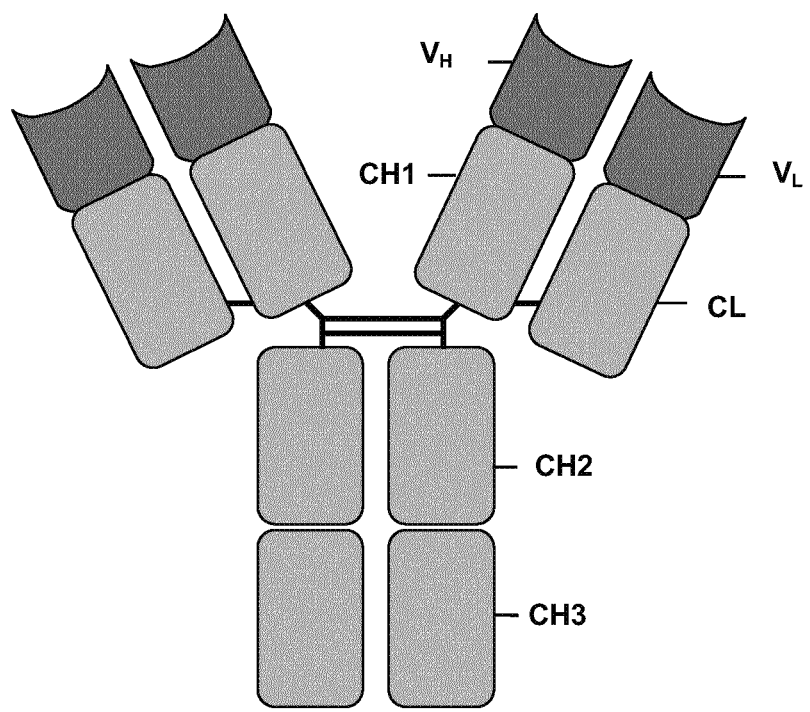
FIG. 2 Immunoglobulin structure showing heavy and light chain polypeptides and the variable (VL and VH) and constant domains (CL and CH1, CH2 and CH3) of each.

The constant region of an antibody includes the portion of each of the heavy and light chain polypeptides outside of the variable region. Immunoglobulin light chains typically include a single constant domain (denoted herein as CL or CL1) which lies C terminal to the VL domain. Immunoglobulin heavy chains typically include a constant region consisting of a first constant domain (CH1) a hinge region, a second constant domain (CH2) and a third constant domain (CH3). As shown in FIG. 2, these domains are positioned C terminal to the VH domain.

The numbering of the amino acids in the heavy and light immunoglobulin chains run from the N-terminus at the forked ends of the Y configuration to the C-terminus at the bottom of each chain. Unless otherwise specified, specific amino acid positions of the heavy chain constant domains are identified herein with reference to the EU numbering scheme for human IgG1 molecules (see Tables 2-4 below). For the kappa and lambda light chains, specific amino acid positions within the constant region are defined with reference to the nomenclature of Kabat et al., supra used for human light chains (see Tables 5 and 6 below)

The Tables below show the correspondence between the different numbering schemes used to identify the residues in the CH1, CH2 and CH3 domains of the human IgG1 heavy chain and the CL domains of the human kappa and human lambda light chains. It would be within the capabilities of the skilled person to align the sequence of a heavy chain or light chain polypeptide of different origin with the sequences shown in the Tables below in order to identify corresponding or equivalent residues.

TABLE 2

Amino acid residues of human IgG1 CH1 domain

| | | CH1 | | | |
|---|---|---|---|---|---|
| Strands, turns and loops for C-domain | IMGT unique numbering for C-domains | IGHG1 amino acid translation[1] | IMGT exon numbering 1-98 | EU numbering (98 aa) 118-215 | Kabat numbering |
| | 1.8 | — | — | — | — |
| | 1.7 | — | — | — | — |
| | 1.6 | — | — | — | — |
| | 1.5 | — | — | — | — |
| | 1.4 | (A) | 1 | 118 | 114 |

TABLE 2-continued

Amino acid residues of human IgG1 CH1 domain

| Strands, turns and loops for C-domain | IMGT unique numbering for C-domains | IGHG1 amino acid translation[1] | IMGT exon numbering | EU numbering (98 aa) 1-98 | Kabat numbering 118-215 |
|---|---|---|---|---|---|
| | 1.3 | S | 2 | 119 | 115 |
| | 1.2 | T | 3 | 120 | 116 |
| | 1.1 | K | 4 | 121 | 117 |
| A-STRAND | 1 | G | 5 | 122 | 118 |
| | 2 | P | 6 | 123 | 119 |
| | 3 | S | 7 | 124 | 120 |
| | 4 | V | 8 | 125 | 121 |
| | 5 | F | 9 | 126 | 122 |
| | 6 | P | 10 | 127 | 123 |
| | 7 | L | 11 | 128 | 124 |
| | 8 | A | 12 | 129 | 125 |
| | 9 | P | 13 | 130 | 126 |
| | 10 | S | 14 | 131 | 127 |
| | 11 | S | 15 | 132 | 128 |
| | 12 | K | 16 | 133 | 129 |
| | 13 | S | 17 | 134 | 130 |
| | 14 | T | 18 | 135 | 133 |
| | 15 | S | 19 | 136 | 134 |
| AB-TURN | 15.1 | — | — | — | — |
| | 15.2 | — | — | — | — |
| | 15.3 | — | — | — | — |
| B-STRAND | 16 | G | 20 | 137 | 135 |
| | 17 | G | 21 | 138 | 136 |
| | 18 | T | 22 | 139 | 137 |
| | 19 | A | 23 | 140 | 138 |
| | 20 | A | 24 | 141 | 139 |
| | 21 | L | 25 | 142 | 140 |
| | 22 | G | 26 | 143 | 141 |
| | 23 | C | 27 | 144 | 142 |
| | 24 | L | 28 | 145 | 143 |
| | 25 | V | 29 | 146 | 144 |
| | 26 | K | 30 | 147 | 145 |
| BC-LOOP | 27 | D | 31 | 148 | 146 |
| | 28 | Y | 32 | 149 | 147 |
| | 29 | F | 33 | 150 | 148 |
| | 30 | P | 34 | 151 | 149 |
| | 31 | — | — | — | — |
| | 34 | — | — | — | — |
| | 35 | E | 35 | 152 | 150 |
| | 36 | P | 36 | 153 | 151 |
| | 37 | V | 37 | 154 | 152 |
| | 38 | T | 38 | 155 | 153 |
| C-STRAND | 39 | V | 39 | 156 | 154 |
| | 40 | S | 40 | 157 | 156 |
| | 41 | W | 41 | 158 | 157 |
| | 42 | N | 42 | 159 | 162 |
| | 43 | S | 43 | 160 | 163 |
| | 44 | G | 44 | 161 | 164 |
| | 45 | A | 45 | 162 | 165 |
| CD-STRAND | 45.1 | L | 46 | 163 | 166 |
| | 45.2 | T | 47 | 164 | 167 |
| | 45.3 | S | 48 | 165 | 168 |
| | 45.4 | — | — | — | — |
| | 45.5 | — | — | — | — |
| | 45.6 | — | — | — | — |
| | 45.7 | — | — | — | — |
| D-STRAND | 77 | G | 49 | 166 | 169 |
| | 78 | V | 50 | 167 | 171 |
| | 79 | H | 51 | 168 | 172 |
| | 80 | T | 52 | 169 | 173 |
| | 81 | F | 53 | 170 | 174 |
| | 82 | P | 54 | 171 | 175 |
| | 83 | A | 55 | 172 | 176 |
| | 84 | V | 56 | 173 | 177 |
| DE-TURN | 84.1 | L | 57 | 174 | 178 |
| | 84.2 | Q | 58 | 175 | 179 |
| | 84.3 | S | 59 | 176 | 180 |
| | 84.4 | S | 60 | 177 | 182 |
| | 84.5 | — | — | — | — |
| | 84.6 | — | — | — | — |
| | 84.7 | — | — | — | — |
| | 85.7 | — | — | — | — |
| | 85.6 | — | — | — | — |
| | 85.5 | — | — | — | — |
| | 85.4 | G | 61 | 178 | 183 |
| | 85.3 | L | 62 | 179 | 184 |
| | 85.2 | Y | 63 | 180 | 185 |
| | 85.1 | S | 64 | 181 | 186 |
| E-STRAND | 85 | L | 65 | 182 | 187 |
| | 86 | S | 66 | 183 | 188 |
| | 87 | S | 67 | 184 | 189 |
| | 88 | V | 68 | 185 | 190 |
| | 89 | V | 69 | 186 | 191 |
| | 90 | T | 70 | 187 | 192 |
| | 91 | V | 71 | 188 | 193 |
| | 92 | P | 72 | 189 | 194 |
| | 93 | S | 73 | 190 | 195 |
| | 94 | S | 74 | 191 | 196 |
| | 95 | S | 75 | 192 | 197 |
| | 96 | L | 76 | 193 | 198 |
| EF-TURN | 96.1 | — | — | — | — |
| | 96.2 | — | — | — | — |
| F-STRAND | 97 | — | — | — | — |
| | 98 | G | 77 | 194 | 199 |
| | 99 | T | 78 | 195 | 200 |
| | 100 | Q | 79 | 196 | 203 |
| | 101 | T | 80 | 197 | 205 |
| | 102 | Y | 81 | 198 | 206 |
| | 103 | I | 82 | 199 | 207 |
| | 104 | C | 83 | 200 | 208 |
| FG-LOOP | 105 | N | 84 | 201 | 209 |
| | 106 | V | 85 | 202 | 210 |
| | 107 | N | 86 | 203 | 211 |
| | 108 | H | 87 | 204 | 212 |
| | 109 | K | 88 | 205 | 213 |
| | 110 | P | 89 | 206 | 214 |
| | 111 | — | — | — | — |
| | 112 | — | — | — | — |
| | 113 | S | 90 | 207 | 215 |
| | 114 | N | 91 | 208 | 216 |
| | 115 | T | 92 | 209 | 217 |
| | 116 | K | 93 | 210 | 218 |
| | 117 | V | 94 | 211 | 219 |
| G-STRAND | 118 | D | 95 | 212 | 220 |
| | 119 | K | 96 | 213 | 221 |
| | 120 | K | 97 | 214 | 222 |
| | 121 | V | 98 | 215 | 223 |
| | 122 | — | — | — | — |
| | 123 | — | — | — | — |
| | 124 | — | — | — | — |
| | 125 | — | — | — | — |
| | 126 | — | — | — | — |
| | 127 | — | — | — | — |
| | 128 | — | — | — | — |
| | 129 | — | — | — | — |
| | 130 | — | — | — | — |

[1] http://www.imgt.org/ligmdb/view?id=J00228

TABLE 3

Amino acid residues of human IgG1 CH2 domain

| Strands, turns and loops for C-domains | IMGT unique numbering for C-domains | IGHG1 amino acid translation[1] | IMGT exon numbering | EU numbering (110 aa) 1-110 | Kabat numbering 231-340 |
|---|---|---|---|---|---|
|  | 1.8 | — | — | — | — |
|  | 1.7 | — | — | — | — |
|  | 1.6 | (A) | 1 | 231 | 244 |
|  | 1.5 | P | 2 | 232 | 245 |
|  | 1.4 | E | 3 | 233 | 246 |
|  | 1.3 | L | 4 | 234 | 247 |
|  | 1.2 | L | 5 | 235 | 248 |
|  | 1.1 | G | 6 | 236 | 249 |
| A-STRAND | 1 | G | 7 | 237 | 250 |
|  | 2 | P | 8 | 238 | 251 |
|  | 3 | S | 9 | 239 | 252 |
|  | 4 | V | 10 | 240 | 253 |
|  | 5 | F | 11 | 241 | 254 |
|  | 6 | L | 12 | 242 | 255 |
|  | 7 | F | 13 | 243 | 256 |
|  | 8 | P | 14 | 244 | 257 |
|  | 9 | P | 15 | 245 | 258 |
|  | 10 | K | 16 | 246 | 259 |
|  | 11 | P | 17 | 247 | 260 |
|  | 12 | K | 18 | 248 | 261 |
|  | 13 | D | 19 | 249 | 262 |
|  | 14 | T | 20 | 250 | 263 |
|  | 15 | L | 21 | 251 | 264 |
| AB-TURN | 15.1 | M | 22 | 252 | 265 |
|  | 15.2 | I | 23 | 253 | 266 |
|  | 15.3 | — | — | — | — |
| B-STRAND | 16 | S | 24 | 254 | 267 |
|  | 17 | R | 25 | 255 | 268 |
|  | 18 | T | 26 | 256 | 269 |
|  | 19 | P | 27 | 257 | 270 |
|  | 20 | E | 28 | 258 | 271 |
|  | 21 | V | 29 | 259 | 272 |
|  | 22 | T | 30 | 260 | 273 |
|  | 23 | C | 31 | 261 | 274 |
|  | 24 | V | 32 | 262 | 275 |
|  | 25 | V | 33 | 263 | 276 |
|  | 26 | V | 34 | 264 | 277 |
| BC-LOOP | 27 | D | 35 | 265 | 278 |
|  | 28 | V | 36 | 266 | 279 |
|  | 29 | S | 37 | 267 | 280 |
|  | 30 | H | 38 | 268 | 281 |
|  | 31 | E | 39 | 269 | 282 |
|  | 34 | D | 40 | 270 | 283 |
|  | 35 | P | 41 | 271 | 284 |
|  | 36 | E | 42 | 272 | 285 |
|  | 37 | V | 43 | 273 | 286 |
|  | 38 | K | 44 | 274 | 287 |
| C-STRAND | 39 | F | 45 | 275 | 288 |
|  | 40 | N | 46 | 276 | 289 |
|  | 41 | W | 47 | 277 | 290 |
|  | 42 | Y | 48 | 278 | 291 |
|  | 43 | V | 49 | 279 | 292 |
|  | 44 | D | 50 | 280 | 295 |
|  | 45 | G | 51 | 281 | 296 |
| CD-STRAND | 45.1 | V | 52 | 282 | 299 |
|  | 45.2 | E | 53 | 283 | 300 |
|  | 45.3 | V | 54 | 284 | 301 |
|  | 45.4 | H | 55 | 285 | 302 |
|  | 45.5 | — | — | — | — |
|  | 45.6 | — | — | — | — |
|  | 45.7 | — | — | — | — |
| D-STRAND | 77 | N | 56 | 286 | 303 |
|  | 78 | A | 57 | 287 | 304 |
|  | 79 | K | 58 | 288 | 305 |
|  | 80 | T | 59 | 289 | 306 |
|  | 81 | K | 60 | 290 | 307 |
|  | 82 | P | 61 | 291 | 308 |
|  | 83 | R | 62 | 292 | 309 |
|  | 84 | E | 63 | 293 | 310 |
| DE-TURN | 84.1 | E | 64 | 294 | 311 |
|  | 84.2 | Q | 65 | 295 | 312 |
|  | 84.3 | Y | 66 | 296 | 313 |
|  | 84.4 | N | 67 | 297 | 314 |
|  | 84.5 | — | — | — | — |
|  | 84.6 | — | — | — | — |
|  | 84.7 | — | — | — | — |
|  | 85.7 | — | — | — | — |
|  | 85.6 | — | — | — | — |
|  | 85.5 | — | — | — | — |
|  | 85.4 | S | 68 | 298 | 317 |
|  | 85.3 | T | 69 | 299 | 318 |
|  | 85.2 | Y | 70 | 300 | 319 |
|  | 85.1 | R | 71 | 301 | 320 |
| E-STRAND | 85 | V | 72 | 302 | 321 |
|  | 86 | V | 73 | 303 | 322 |
|  | 87 | S | 74 | 304 | 323 |
|  | 88 | V | 75 | 305 | 324 |
|  | 89 | L | 76 | 306 | 325 |
|  | 90 | T | 77 | 307 | 326 |
|  | 91 | V | 78 | 308 | 327 |
|  | 92 | L | 79 | 309 | 328 |
|  | 93 | H | 80 | 310 | 329 |
|  | 94 | Q | 81 | 311 | 330 |
|  | 95 | D | 82 | 312 | 331 |
|  | 96 | W | 83 | 313 | 332 |
| EF-TURN | 96.1 | — | — | — | — |
|  | 96.2 | — | — | — | — |
| F-STRAND | 97 | L | 84 | 314 | 333 |
|  | 98 | N | 85 | 315 | 334 |
|  | 99 | G | 86 | 316 | 335 |
|  | 100 | K | 87 | 317 | 336 |
|  | 101 | E | 88 | 318 | 337 |
|  | 102 | Y | 89 | 319 | 338 |
|  | 103 | K | 90 | 320 | 339 |
|  | 104 | C | 91 | 321 | 340 |
| FG-LOOP | 105 | K | 92 | 322 | 341 |
|  | 106 | V | 93 | 323 | 342 |
|  | 107 | S | 94 | 324 | 343 |
|  | 108 | N | 95 | 325 | 344 |
|  | 109 | K | 96 | 326 | 345 |
|  | 110 | A | 97 | 327 | 346 |
|  | 111 | — | — | — | — |
|  | 112 | — | — | — | — |
|  | 113 | L | 98 | 328 | 347 |
|  | 114 | P | 99 | 329 | 348 |
|  | 115 | A | 100 | 330 | 349 |
|  | 116 | P | 101 | 331 | 350 |
|  | 117 | I | 102 | 332 | 351 |
| G-STRAND | 118 | E | 103 | 333 | 352 |
|  | 119 | K | 104 | 334 | 353 |
|  | 120 | T | 105 | 335 | 354 |
|  | 121 | I | 106 | 336 | 355 |
|  | 122 | S | 107 | 337 | 357 |
|  | 123 | K | 108 | 338 | 358 |
|  | 124 | A | 109 | 339 | 359 |
|  | 125 | K | 110 | 340 | 360 |
|  | 126 | — | — | — | — |
|  | 127 | — | — | — | — |
|  | 128 | — | — | — | — |
|  | 129 | — | — | — | — |
|  | 130 | — | — | — | — |

[1] http://www.imgt.org/ligmdb/view?id=J00228

TABLE 4

Amino acid residues of human IgG1 CH3 domain

| Strands, turns and loops for C-domains | CH3 IMGT unique numbering for C-domains | IGHG1 amino acid translation[1] | IMGT exon numbering | EU numbering (107 aa) 1-107 | Kabat numbering 341-446 |
|---|---|---|---|---|---|
| | 1.8 | — | — | — | — |
| | 1.7 | — | — | — | — |
| | 1.6 | — | — | — | — |
| | 1.5 | — | — | — | — |
| | 1.4 | (G) | 1 | 341 | 361 |
| | 1.3 | Q | 2 | 342 | 363 |
| | 1.2 | P | 3 | 343 | 364 |
| | 1.1 | R | 4 | 344 | 365 |
| A-STRAND | 1 | E | 5 | 345 | 366 |
| | 2 | P | 6 | 346 | 367 |
| | 3 | Q | 7 | 347 | 368 |
| | 4 | V | 8 | 348 | 369 |
| | 5 | Y | 9 | 349 | 370 |
| | 6 | T | 10 | 350 | 371 |
| | 7 | L | 11 | 351 | 372 |
| | 8 | P | 12 | 352 | 373 |
| | 9 | P | 13 | 353 | 374 |
| | 10 | S | 14 | 354 | 375 |
| | 11 | R | 15 | 355 | 376 |
| | 12 | D | 16 | 356 | 377 |
| | 13 | E | 17 | 357 | 378 |
| | 14 | L | 18 | 358 | 381 |
| | 15 | T | 19 | 359 | 382 |
| AB-TURN | 15.1 | — | — | — | — |
| | 15.2 | — | — | — | — |
| | 15.3 | — | — | — | — |
| B-STRAND | 16 | K | 20 | 360 | 383 |
| | 17 | N | 21 | 361 | 384 |
| | 18 | Q | 22 | 362 | 385 |
| | 19 | V | 23 | 363 | 386 |
| | 20 | S | 24 | 364 | 387 |
| | 21 | L | 25 | 365 | 388 |
| | 22 | T | 26 | 366 | 389 |
| | 23 | C | 27 | 367 | 390 |
| | 24 | L | 28 | 368 | 391 |
| | 25 | V | 29 | 369 | 392 |
| | 26 | K | 30 | 370 | 393 |
| BC-LOOP | 27 | G | 31 | 371 | 394 |
| | 28 | F | 32 | 372 | 395 |
| | 29 | Y | 33 | 373 | 396 |
| | 30 | P | 34 | 374 | 397 |
| | 31 | — | — | — | — |
| | 34 | — | — | — | — |
| | 35 | S | 35 | 375 | 398 |
| | 36 | D | 36 | 376 | 399 |
| | 37 | I | 37 | 377 | 400 |
| | 38 | A | 38 | 378 | 401 |
| C-STRAND | 39 | V | 39 | 379 | 402 |
| | 40 | E | 40 | 380 | 405 |
| | 41 | W | 41 | 381 | 406 |
| | 42 | E | 42 | 382 | 407 |
| | 43 | S | 43 | 383 | 408 |
| | 44 | N | 44 | 384 | 410 |
| | 45 | G | 45 | 385 | 411 |
| CD-STRAND | 45.1 | Q | 46 | 386 | 414 |
| | 45.2 | P | 47 | 387 | 415 |
| | 45.3 | E | 48 | 388 | 416 |
| | 45.4 | N | 49 | 389 | 417 |
| | 45.5 | — | — | — | — |
| | 45.6 | — | — | — | — |
| | 45.7 | — | — | — | — |
| D-STRAND | 77 | N | 50 | 390 | 418 |
| | 78 | Y | 51 | 391 | 419 |
| | 79 | K | 52 | 392 | 420 |
| | 80 | T | 53 | 393 | 421 |
| | 81 | T | 54 | 394 | 422 |
| | 82 | P | 55 | 395 | 423 |
| | 83 | P | 56 | 396 | 424 |
| | 84 | V | 57 | 397 | 425 |
| DE-TURN | 84.1 | L | 58 | 398 | 426 |
| | 84.2 | D | 59 | 399 | 427 |
| | 84.3 | S | 60 | 400 | 428 |
| | 84.4 | D | 61 | 401 | 430 |
| | 84.5 | — | — | — | — |
| | 84.6 | — | — | — | — |
| | 84.7 | — | — | — | — |
| | 85.7 | — | — | — | — |
| | 85.6 | — | — | — | — |
| | 85.5 | — | — | — | — |
| | 85.4 | G | 62 | 402 | 433 |
| | 85.3 | S | 63 | 403 | 434 |
| | 85.2 | F | 64 | 404 | 435 |
| | 85.1 | F | 65 | 405 | 436 |
| E-STRAND | 85 | L | 66 | 406 | 437 |
| | 86 | Y | 67 | 407 | 438 |
| | 87 | S | 68 | 408 | 439 |
| | 88 | K | 69 | 409 | 440 |
| | 89 | L | 70 | 410 | 441 |
| | 90 | T | 71 | 411 | 442 |
| | 91 | V | 72 | 412 | 443 |
| | 92 | D | 73 | 413 | 444 |
| | 93 | K | 74 | 414 | 445 |
| | 94 | S | 75 | 415 | 446 |
| | 95 | R | 76 | 416 | 447 |
| | 96 | W | 77 | 417 | 448 |
| EF-TURN | 96.1 | — | — | — | — |
| | 96.2 | — | — | — | — |
| F-STRAND | 97 | Q | 78 | 418 | 449 |
| | 98 | Q | 79 | 419 | 450 |
| | 99 | G | 80 | 420 | 451 |
| | 100 | N | 81 | 421 | 452 |
| | 101 | V | 82 | 422 | 453 |
| | 102 | F | 83 | 423 | 454 |
| | 103 | S | 84 | 424 | 455 |
| | 104 | C | 85 | 425 | 456 |
| FG-LOOP | 105 | S | 86 | 426 | 457 |
| | 106 | V | 87 | 427 | 458 |
| | 107 | M | 88 | 428 | 459 |
| | 108 | H | 89 | 429 | 460 |
| | 109 | E | 90 | 430 | 461 |
| | 110 | A | 91 | 431 | 462 |
| | 111 | — | — | — | — |
| | 112 | L | 92 | 432 | 463 |
| | 113 | H | 93 | 433 | 464 |
| | 114 | N | 94 | 434 | 465 |
| | 115 | H | 95 | 435 | 466 |
| | 116 | Y | 96 | 436 | 467 |
| | 117 | T | 97 | 437 | 468 |
| G-STRAND | 118 | Q | 98 | 438 | 469 |
| | 119 | K | 99 | 439 | 470 |
| | 120 | S | 100 | 440 | 471 |
| | 121 | L | 101 | 441 | 472 |
| | 122 | S | 102 | 442 | 473 |
| | 123 | L | 103 | 443 | 474 |
| | 124 | S | 104 | 444 | 475 |
| | 125 | P | 105 | 445 | 476 |
| | 126 | — | — | — | — |
| | 127 | — | — | — | — |
| | 128 | — | — | — | — |
| | 129 | G | CHS 106 | 446 | 477 |
| | 130 | K | CHS 107 | 447 | |

[1] http://www.imgt.org/ligmdb/view?id=J00228

TABLE 5

Amino acid residues of human kappa CL domain

| Strands, turns and loops for C-DOMAINs | IMGT unique numbering for C-DOMAINs | C-REGION | | | |
|---|---|---|---|---|---|
| | | IGKC amino acid translation | IMGT exon numbering 1-107 | EU numbering (107 aa) 108-214 | Kabat numbering |
| | 1.8 | — | — | — | — |
| | 1.7 | — | — | — | — |
| | 1.6 | — | — | — | — |
| | 1.5 | — | — | — | — |
| | 1.4 | (R) | 1 | 108 | 108 |
| | 1.3 | T | 2 | 109 | 109 |
| | 1.2 | V | 3 | 110 | 110 |
| | 1.1 | A | 4 | 111 | 111 |
| A-STRAND | 1 | A | 5 | 112 | 112 |
| | 2 | P | 6 | 113 | 113 |
| | 3 | S | 7 | 114 | 114 |
| | 4 | V | 8 | 115 | 115 |
| | 5 | F | 9 | 116 | 116 |
| | 6 | I | 10 | 117 | 117 |
| | 7 | F | 11 | 118 | 118 |
| | 8 | P | 12 | 119 | 119 |
| | 9 | P | 13 | 120 | 120 |
| | 10 | S | 14 | 121 | 121 |
| | 11 | D | 15 | 122 | 122 |
| | 12 | E | 16 | 123 | 123 |
| | 13 | Q | 17 | 124 | 124 |
| | 14 | L | 18 | 125 | 125 |
| | 15 | K | 19 | 126 | 126 |
| AB-TURN | 15.1 | — | — | — | — |
| | 15.2 | — | — | — | — |
| | 15.3 | — | — | — | — |
| B-STRAND | 16 | S | 20 | 127 | 127 |
| | 17 | G | 21 | 128 | 128 |
| | 18 | T | 22 | 129 | 129 |
| | 19 | A | 23 | 130 | 130 |
| | 20 | S | 24 | 131 | 131 |
| | 21 | V | 25 | 132 | 132 |
| | 22 | V | 26 | 133 | 133 |
| | 23 | C | 27 | 134 | 134 |
| | 24 | L | 28 | 135 | 135 |
| | 25 | L | 29 | 136 | 136 |
| | 26 | N | 30 | 137 | 137 |
| BC-LOOP | 27 | N | 31 | 138 | 138 |
| | 28 | F | 32 | 139 | 139 |
| | 29 | Y | 33 | 140 | 140 |
| | 30 | P | 34 | 141 | 141 |
| | 31 | — | — | — | — |
| | 34 | — | — | — | — |
| | 35 | R | 35 | 142 | 142 |
| | 36 | E | 36 | 143 | 143 |
| | 37 | A | 37 | 144 | 144 |
| | 38 | K | 38 | 145 | 145 |
| C-STRAND | 39 | V | 39 | 146 | 146 |
| | 40 | Q | 40 | 147 | 147 |
| | 41 | W | 41 | 148 | 148 |
| | 42 | K | 42 | 149 | 149 |
| | 43 | V | 43 | 150 | 150 |
| | 44 | D | 44 | 151 | 151 |
| | 45 | N | 45 | 152 | 152 |
| CD-STRAND | 45.1 | A | 46 | 153 | 153 |
| | 45.2 | L | 47 | 154 | 154 |
| | 45.3 | Q | 48 | 155 | 155 |
| | 45.4 | S | 49 | 156 | 156 |
| | 45.5 | G | 50 | 157 | 157 |
| | 45.6 | — | — | — | — |
| | 45.7 | — | — | — | — |
| D-STRAND | 77 | N | 51 | 158 | 158 |
| | 78 | S | 52 | 159 | 159 |
| | 79 | Q | 53 | 160 | 160 |
| | 80 | E | 54 | 161 | 161 |
| | 81 | S | 55 | 162 | 162 |
| | 82 | V | 56 | 163 | 163 |
| | 83 | T | 57 | 164 | 164 |
| | 84 | E | 58 | 165 | 165 |

TABLE 5-continued

| | Amino acid residues of human kappa CL domain | | | | |
|---|---|---|---|---|---|
| | | | C-REGION | | |
| Strands, turns and loops for C-DOMAINs | IMGT unique numbering for C-DOMAINs | IGKC amino acid translation | IMGT exon numbering 1-107 | EU numbering (107 aa) 108-214 | Kabat numbering |
| DE-TURN | 84.1 | Q | 59 | 166 | 166 |
| | 84.2 | D | 60 | 167 | 167 |
| | 84.3 | S | 61 | 168 | 168 |
| | 84.4 | K | 62 | 169 | 169 |
| | 84.5 | D | 63 | 170 | 170 |
| | 84.6 | — | — | — | — |
| | 84.7 | — | — | — | — |
| | 85.7 | — | — | — | — |
| | 85.6 | — | — | — | — |
| | 85.5 | — | — | — | — |
| | 85.4 | S | 64 | 171 | 171 |
| | 85.3 | T | 65 | 172 | 172 |
| | 85.2 | Y | 66 | 173 | 173 |
| | 85.1 | S | 67 | 174 | 174 |
| E-STRAND | 85 | L | 68 | 175 | 175 |
| | 86 | S | 69 | 176 | 176 |
| | 87 | S | 70 | 177 | 177 |
| | 88 | T | 71 | 178 | 178 |
| | 89 | L | 72 | 179 | 179 |
| | 90 | T | 73 | 180 | 180 |
| | 91 | L | 74 | 181 | 181 |
| | 92 | S | 75 | 182 | 182 |
| | 93 | K | 76 | 183 | 183 |
| | 94 | A | 77 | 184 | 184 |
| | 95 | D | 78 | 185 | 185 |
| | 96 | Y | 79 | 186 | 186 |
| EF-TURN | 96.1 | — | — | — | — |
| | 96.2 | — | — | — | — |
| F-STRAND | 97 | E | 80 | 187 | 187 |
| | 98 | K | 81 | 188 | 188 |
| | 99 | H | 82 | 189 | 189 |
| | 100 | K | 83 | 190 | 190 |
| | 101 | V | 84 | 191 | 191 |
| | 102 | Y | 85 | 192 | 192 |
| | 103 | A | 86 | 193 | 193 |
| | 104 | C | 87 | 194 | 194 |
| FG-LOOP | 105 | E | 88 | 195 | 195 |
| | 106 | V | 89 | 196 | 196 |
| | 107 | T | 90 | 197 | 197 |
| | 108 | H | 91 | 198 | 198 |
| | 109 | Q | 92 | 199 | 199 |
| | 110 | G | 93 | 200 | 200 |
| | 111 | — | — | — | — |
| | 112 | — | — | — | — |
| | 113 | L | 94 | 201 | 201 |
| | 114 | S | 95 | 202 | 202 |
| | 115 | S | 96 | 203 | 203 |
| | 116 | P | 97 | 204 | 204 |
| | 117 | V | 98 | 205 | 205 |
| G-STRAND | 118 | T | 99 | 206 | 206 |
| | 119 | K | 100 | 207 | 207 |
| | 120 | S | 101 | 208 | 208 |
| | 121 | F | 102 | 209 | 209 |
| | 122 | N | 103 | 210 | 210 |
| | 123 | R | 104 | 211 | 211 |
| | 124 | G | 105 | 212 | 212 |
| | 125 | E | 106 | 213 | 213 |
| | 126 | C | 107 | 214 | 214 |
| | 127 | — | — | — | 215 |
| | 128 | — | — | — | 216 |

[1] http://www.imgt.org/ligmdb/view?id=J00241

TABLE 6

Amino acid residues of human lambda CL domain

| Strands, turns and loops for C-DOMAINs | IMGT unique numbering for C-DOMAINs | C-REGION IGLC amino acid translation[1] | C-REGION IMGT exon numbering 1-106 | Kabat numbering |
|---|---|---|---|---|
| | 1.8 | — | — | — |
| | 1.7 | — | — | — |
| | 1.6 | — | — | — |
| | 1.5 | (G) | 1 | 107A |
| | 1.4 | Q | 2 | 108 |
| | 1.3 | P | 3 | 109 |
| | 1.2 | K | 4 | 110 |
| | 1.1 | A | 5 | 111 |
| A-STRAND | 1 | N | 6 | 112 |
| | 2 | P | 7 | 113 |
| | 3 | T | 8 | 114 |
| | 4 | V | 9 | 115 |
| | 5 | T | 10 | 116 |
| | 6 | L | 11 | 117 |
| | 7 | F | 12 | 118 |
| | 8 | P | 13 | 119 |
| | 9 | P | 14 | 120 |
| | 10 | S | 15 | 121 |
| | 11 | S | 16 | 122 |
| | 12 | E | 17 | 123 |
| | 13 | E | 18 | 124 |
| | 14 | L | 19 | 125 |
| | 15 | Q | 20 | 126 |
| AB-TURN | 15.1 | — | — | — |
| | 15.2 | — | — | — |
| | 15.3 | — | — | — |
| B-STRAND | 16 | A | 21 | 127 |
| | 17 | N | 22 | 128 |
| | 18 | K | 23 | 129 |
| | 19 | A | 24 | 130 |
| | 20 | T | 25 | 131 |
| | 21 | L | 26 | 132 |
| | 22 | V | 27 | 133 |
| | 23 | C | 28 | 134 |
| | 24 | L | 29 | 135 |
| | 25 | I | 30 | 136 |
| | 26 | S | 31 | 137 |
| BC-LOOP | 27 | D | 32 | 138 |
| | 28 | F | 33 | 139 |
| | 29 | Y | 34 | 140 |
| | 30 | P | 35 | 141 |
| | 31 | — | — | — |
| | 34 | — | — | — |
| | 35 | G | 36 | 142 |
| | 36 | A | 37 | 143 |
| | 37 | V | 38 | 144 |
| | 38 | T | 39 | 145 |
| C-STRAND | 39 | V | 40 | 146 |
| | 40 | A | 41 | 147 |
| | 41 | W | 42 | 148 |
| | 42 | K | 43 | 149 |
| | 43 | A | 44 | 150 |
| | 44 | D | 45 | 151 |
| | 45 | G | 46 | 152 |
| CD-STRAND | 45.1 | S | 47 | 153 |
| | 45.2 | P | 48 | 154 |
| | 45.3 | V | 49 | 155 |
| | 45.4 | K | 50 | 156 |
| | 45.5 | A | 51 | 157 |
| | 45.6 | — | — | — |
| | 45.7 | — | — | — |
| D-STRAND | 77 | G | 52 | 158 |
| | 78 | V | 53 | 159 |
| | 79 | E | 54 | 160 |
| | 80 | T | 55 | 161 |
| | 81 | T | 56 | 162 |
| | 82 | K | 57 | 163 |
| | 83 | P | 58 | 164 |
| | 84 | S | 59 | 165 |
| DE-TURN | 84.1 | K | 60 | 166 |
| | 84.2 | Q | 61 | 167 |
| | 84.3 | S | 62 | 168 |
| | 84.4 | N | 63 | 170 |
| | 84.5 | — | — | — |
| | 84.6 | — | — | — |
| | 84.7 | — | — | — |
| | 85.7 | — | — | — |
| | 85.6 | — | — | — |
| | 85.5 | — | — | — |
| | 85.4 | N | 64 | 171 |
| | 85.3 | K | 65 | 172 |
| | 85.2 | Y | 66 | 173 |
| | 85.1 | A | 67 | 174 |
| E-STRAND | 85 | A | 68 | 175 |
| | 86 | S | 69 | 176 |
| | 87 | S | 70 | 177 |
| | 88 | Y | 71 | 178 |
| | 89 | L | 72 | 179 |
| | 90 | S | 73 | 180 |
| | 91 | L | 74 | 181 |
| | 92 | T | 75 | 182 |
| | 93 | P | 76 | 183 |
| | 94 | E | 77 | 184 |
| | 95 | Q | 78 | 185 |
| | 96 | W | 79 | 186 |
| EF-TURN | 96.1 | — | — | — |
| | 96.2 | — | — | — |
| F-STRAND | 97 | K | 80 | 187 |
| | 98 | S | 81 | 188 |
| | 99 | H | 82 | 189 |
| | 100 | R | 83 | 190 |
| | 101 | S | 84 | 191 |
| | 102 | Y | 85 | 192 |
| | 103 | S | 86 | 193 |
| | 104 | C | 87 | 194 |
| FG-LOOP | 105 | Q | 88 | 195 |
| | 106 | V | 89 | 196 |
| | 107 | T | 90 | 197 |
| | 108 | H | 91 | 198 |
| | 109 | E | 92 | 199 |
| | 110 | — | — | — |
| | 111 | — | — | — |
| | 112 | — | — | — |
| | 113 | — | — | — |
| | 114 | G | 93 | 200 |
| | 115 | S | 94 | 203 |
| | 116 | T | 95 | 204 |
| | 117 | V | 96 | 205 |
| G-STRAND | 118 | E | 97 | 206 |
| | 119 | K | 98 | 207 |
| | 120 | T | 99 | 208 |
| | 121 | V | 100 | 209 |
| | 122 | A | 101 | 210 |
| | 123 | P | 102 | 211 |
| | 124 | T | 103 | 212 |
| | 125 | E | 104 | 213 |
| | 126 | C | 105 | 214 |
| | 127 | S | 106 | 215 |
| | 128 | — | — | 216 |

[1] http://www.imgt.org/ligmdb/view?id=X51755

"Immunoglobulin Allotype"

As used herein the term "allotype" or "immunoglobulin allotype" indicates that the immunoglobulin chain or polypeptide is encoded by a particular allele found in an individual. Different immunoglobulin allotypes have different sequences reflecting the natural variation found in the alleles of an individual's genome. The natural variation normally manifests in the constant region of the immunoglobulin heavy and light chain alleles and therefore different allotypes typically differ in the constant region of the polypeptide, as defined above.

"Derived From"

As used herein the term "derived from" a designated protein (e.g. a human protein) refers to the origin of the polypeptide or amino acid sequence. In the context of the present invention, a fragment "derived from" a designated protein means a fragment having an amino acid sequence which is essentially identical to the amino acid sequence of the originating or starting polypeptide. For example, a fragment derived from a human immunoglobulin allotype will have an amino acid sequence corresponding to the section of the human immunoglobulin polypeptide from which the fragment is taken.

In certain embodiments, the amino acid sequence which is derived from a particular starting polypeptide is not contiguous. For example, in one embodiment, one, two, three, four, five, or six CDRs are derived from a starting antibody. In one embodiment, the polypeptide or amino acid sequence which is derived from a particular starting polypeptide or amino acid sequence has an amino acid sequence that is essentially identical to that of the starting sequence, or a portion thereof wherein the portion consists of at least 3-5 amino acids, at least 5-10 amino acids, at least 10-20 amino acids, at least 20-30 amino acids, or at least 30-50 amino acids, or which is otherwise identifiable to one of ordinary skill in the art as having its origin in the starting sequence. In one embodiment, the one or more CDR sequences derived from the starting antibody are altered to produce variant CDR sequences, e.g. affinity variants, wherein the variant CDR sequences maintain target antigen binding activity.

"Specificity" and "Multispecific Antibody"

The term "specificity" refers to the ability of an antibody to specifically bind (e.g., immunoreact with) a given target antigen, e.g., a human target antigen. An antibody molecule may be monospecific and contain one or more binding sites which specifically bind a single epitope on a single target antigen. Alternatively, an antibody molecule may be "multispecific" and contain two or more antigen binding sites which specifically bind different epitopes either within the same antigen or located within different target antigens. For example, a bispecific antibody has two antigen binding sites capable of recognising and binding two different target epitopes or antigens. In order to achieve multiple specificities, multispecific antibodies are engineered to include different combinations or pairings of heavy and light chain polypeptides with different VH-VL pairs.

"Chimeric"

A "chimeric" protein comprises a first amino acid sequence linked to a second amino acid sequence with which it is not naturally linked in nature. The amino acid sequences may normally exist in separate proteins that are brought together in the fusion polypeptide or they may normally exist in the same protein but are placed in a new arrangement in the fusion polypeptide. A chimeric protein may be created, for example, by chemical synthesis, or by creating and translating a polynucleotide in which the peptide regions are encoded in the desired relationship. Exemplary chimeric antibodies include fusion proteins comprising VH and/or VL domains derived from one species e.g. a species of the camelid family (or humanised variants thereof) fused to the constant domains of a human antibody, e.g. human IgG1, IgG2, IgG3 or IgG4.

"Conservative Amino Acid Substitution"

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, an amino acid residue in an immunoglobulin polypeptide may be replaced with another amino acid residue from the same side chain family. In another embodiment, a string of amino acids can be replaced with a structurally similar string that differs in order and/or composition of side chain family members.

"Engineered"

As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques). The antibodies of the invention may be engineered as described herein below to incorporate variation into the region of the antibody molecule outside of the antigen binding site(s). The antibodies may also be engineered, for example, humanized and/or chimeric antibodies, and antibodies which have been engineered to improve one or more properties such as antigen binding, stability/half-life or effector function.

"Humanising Substitutions"

As used herein, the term "humanising substitutions" refers to amino acid substitutions in which the amino acid residue present at a particular position in the VH or VL domain antibody (for example a camelid-derived antibody) is replaced with an amino acid residue which occurs at an equivalent position in a reference human VH or VL domain. The reference human VH or VL domain may be a VH or VL domain encoded by the human germline. Humanising substitutions may be made in the framework regions and/or the CDRs of an antibody, defined herein.

"Humanised Antibody or Variant"

As used herein the term "humanised antibody" or "humanised variant" refers to a variant antibody which contains one or more "humanising substitutions" compared to a reference antibody, wherein a portion of the reference antibody (e.g. the VH domain and/or the VL domain or parts thereof containing at least one CDR) has an amino acid derived from a non-human species, and the "humanising substitutions" occur within the amino acid sequence derived from a non-human species.

"Heavy-Chain Only Antibody" or "VHH Antibody"

As used herein, the term "heavy-chain only antibody" or "VHH antibody" refers to a second type of antibody produced only by species of the Camelidae family, which includes camels, llama, alpaca. Heavy chain-only antibodies are composed of two heavy chains and are devoid of light chains. Each heavy chain has a variable domain at the N-terminus, and these variable domains are referred to as "VHH" domains in order to distinguish them from the variable domains of the heavy chains of the conventional heterotetrameric antibodies i.e. the VH domains, described above.

B. Multispecific Antibodies

The present invention relates to multispecific antibodies having binding specificity for multiple distinct epitopes, wherein "multiple" means two or more distinct epitopes. The multispecific antibodies of the present invention may have binding specificity for at least two, at least three, at least four, at least five epitopes either within the same target antigen or in different target antigens. In preferred embodiments, the antibodies of the invention are bispecific antibodies having specificity for two distinct epitopes either within the same target antigen or in different target antigens.

First and Second Heavy Chain-Light Chain Pairings Define First and Second Antigen Binding Sites In order to achieve a multispecific binding profile, multispecific antibodies incorporate different heavy chain-light pairings or combinations. The term "pairing" as used herein refers to the paired configuration of heavy and light chains within the immunoglobulin molecule, for example as shown in FIG. 2, wherein each heavy chain-light chain pair (or pairing) forms a variable region consisting of the VH and VL domains of the heavy and light chains, respectively. It is these variable regions of the antibody molecule and in particular, the CDR sequences contained within each of the VH and VL domains that define the antigen binding sites.

Multispecific antibodies of the present invention comprise or consist of a first pairing between a first heavy chain and a first light chain and a second pairing between a second heavy chain and a second light chain. The corresponding heavy and light chains may pair via a disulphide bond as found in naturally occurring immunoglobulin molecules, although in the context of the present invention, "pairing" may be association of the chains via any suitable means including non-covalent association.

The first and second heavy chain-light chain pairings create two distinct variable regions within the antibody such that the antibody has at least two distinct antigen binding sites capable of recognising and binding different epitopes on the same or different antigens. It is thus the precise pairing of the correct heavy and light chain combinations within the overall quaternary structure of the antibody molecule that ensures that the multispecific antibody has the correct binding profile. Mispairing between the respective heavy and light chains of the antibody will result in an antibody either lacking the multispecific properties required and/or an immunoglobulin lacking antigen binding activity altogether.

Selective Recognition Sites Outside the Antigen Binding Sites

The present invention addresses the problem of heavy chain-light chain mispairing by providing multispecific antibodies comprising or consisting of first and second heavy chain-light chain pairings, wherein the pairings can be distinguished by distinct or unique "selective recognition sites" located outside the antigen binding sites of the molecule. The "selective recognition sites" are distinct or unique in the sense that they can be selectively recognised or selectively bound by different "selective recognition agents", wherein such agents are characterised further below in the context of the methods of the present invention. The selective binding of "selective recognition agents" to their cognate "selective recognition sites" allows the first and second selective recognition sites to be distinguished or differentiated from each other. The first and second selective recognition sites are thus differentially bound by their respective selective recognition agents.

A selective recognition site according to the present invention is a site in the antibody molecule comprising or consisting of a distinct or unique combination of amino acid residues formed by a distinct heavy chain-light chain pairing. As described below, each selective recognition site comprises or consists of at least one amino acid residue from the heavy chain and at least one amino acid residue from the light chain of each pairing. For sites comprising more than one amino acid residue from the heavy chain and/or more than one amino acid from the light chain, the residues from the same immunoglobulin chain may be contiguous or non-contiguous in the polypeptide sequence. The combination of amino acid residues of each selective recognition site typically form a conformational epitope that can be selectively recognised by a cognate selective recognition agent. The amino acid residues that define the selective recognition site or conformational epitope are the residues that contribute to the binding interface between the site/epitope and the recognition agent that binds to the site/epitope.

Each selective recognition site must comprise or consist of enough amino acid residues and in particular, enough different amino acid residues, for it to be bound exclusively or at least preferentially by a selective recognition agent as described further below. The combination of amino acid residues that form each selective recognition site will typically be clustered i.e. in close spatial proximity, in the overall quaternary structure of the antibody molecule so as to form a conformational epitope selectively recognised by a selective recognition agent.

Multispecific antibodies of the present invention include at least two selective recognition sites: a first selective recognition site formed by the first heavy chain-light chain pairing and a second selective recognition site formed by the second heavy chain-light chain pairing. Each of the first and second selective recognition sites comprises at least one amino acid residue from the heavy chain of the pair and at least one amino acid residue from the light chain of the pair. In certain embodiments, one or both first and second selective recognition sites comprise at least two, at least three, at least four, at least five amino acid residues from the heavy chain of the pair and/or at least two, at least three, at least four, at least five amino acid residues from the light chain of the pair. Amino acid residues from both the heavy chain and light chain of each pair contribute to their respective selective recognition sites as this allows for antibodies having the correct heavy chain-light chain pairings to be detected and isolated using the methods described herein.

In order for the first and second selective recognition sites to be distinguished from each other and potentially from other recognition sites located within the same antibody molecule, each selective recognition site must include enough amino acid residues for it to be recognised and bound by a selective recognition agent. Each selective recognition site may comprise or consist of a total of at least 2, at least 3, at least 4, at least 5, at least 6, at least 7, at least 8, at least 9, at least 10 residues wherein at least one residue is from the heavy chain and at least one residue is from the light chain of each pairing.

Each selective recognition site must include enough amino acid residues that differ, as compared with other recognition sites within the same molecule, in order for the individual sites to be selectively recognised i.e. distinguished from each other. In order for the first and second selective recognition sites to be distinguished from each other, the combination of amino acid residues of the first selective recognition site must differ by at least one amino acid residue from the combination of amino acid residues of the second selective recognition site, and any further sites within the same molecule. In certain embodiments, the combination of amino acid residues of the first and second selective recognition sites differ by at least 1, 2, 3, 4, 5, 6, 7, 8, 9, 10, 15 amino acid residues.

The amino acid residues that contribute to each selective recognition site may be located within any suitable part of the heavy chain and any suitable part of the light chain, with the exception of the antigen binding site. The term "antigen binding site" is defined elsewhere herein and contains residues from the CDR sequences of the VH and VL domains.

In certain embodiments, the first and/or second selective recognition sites comprise or consist of one or more residues located within the framework region of the VH domain of the heavy chain and/or one or more residues located within the framework region of the VL domain of the light chain. In certain embodiments, one or both selective recognition sites comprise one or more residues located within the framework regions of the VH domain and/or the VL domain, preferably framework region 2 (FR2) of the VH domain and/or the VL domain.

In preferred embodiments of the invention, the first and/or second selective recognition site comprises or consists of one or more residues located within any suitable part of the constant region of the light chain and one or more residues located within any suitable part of the constant region of the heavy chain, wherein the constant region of the heavy chain is defined by the CH1-hinge-CH2-CH3 region of the molecule. Since each selective recognition site must include at least one residue contributed from the heavy chain and light chain of each pairing, the residue(s) from the heavy chain and the residue(s) from the light chain are preferably in close spatial proximity in the three-dimensional pairwise configuration of the antibody. In certain embodiments, the residue(s) from the heavy chain and the residue(s) from the light chain are within a distance of from about 20 Å to about 100 Å or from about 20 Å to about 50 Å or from about 20 Å to about 25 Å in the three-dimensional pairwise configuration of the antibody.

In certain embodiments, the first selective recognition site will comprise or consist of one or more amino acid residues from the CL domain of the first light chain and one or more residues from the CH1 domain of the first heavy chain. Alternatively or in addition, the second selective recognition site will comprise or consist of one or more amino acid residues from the CL domain of the second light chain and one or more amino acid residues from the CH1 domain of the second heavy chain.

The selective recognition sites may comprise or consist of one or more solvent-exposed residues located within the heavy chain and/or light chain of the pairing. Solvent-exposed amino acids can be identified using the program NACCESS as described by Rothlisberger et al. (J. Mol. Biol. (2005) 347, 773-789), the contents of which are incorporated herein in their entirety, and on the Plueckthun website.

As explained above, the combination of amino acid residues of each selective recognition site must differ by at least one amino acid residue from the combination of amino acid residues of any other recognition sites within the same molecule in order for each selective recognition site to be distinguished by the binding of a selective recognition agent. The residues that differ between first and second selective recognition sites may be contributed from the heavy chain of the pair and/or the light chain of the pair.

In certain embodiments, the multispecific antibodies of the invention comprise first and second heavy chains wherein the amino acid sequence outside of the antigen binding site differs by at least one amino acid residue, and the first and/or second selective recognition site comprises or consists of one or more of the residues that differ between the chains.

In the context of the present invention, amino acid residues are held to differ if a comparison between two heavy chain polypeptides or two light chain polypeptides identifies a different residue at a corresponding position in the two chains.

In certain embodiments, the multispecific antibodies comprise first and second heavy chains wherein the amino acid sequences of the constant regions, and preferably the amino acid sequences of the CH1 domains, differ by at least one amino acid residue and the first and/or second selective recognition site comprises or consists of one or more of the residues that differ in the constant region, particularly in the CH1 domain. In certain embodiments, the first and second heavy chains differ by at least one amino acid residue in the solvent exposed regions of the heavy chains, the first and/or second selective recognition site comprises or consists of one of said solvent-exposed residues. In certain embodiments, the first and second heavy chains differ by at least one residue located outside of the binding interface between the paired or dimerized CH3 domains of the first and second heavy chains and the first and/or second selective recognition site comprises or consists of at least one of said residues.

In certain embodiments, the first and second heavy chains differ by at least one amino acid residue in the CH1 domain located outside of the binding interface between the CH1 domain of the heavy chain and the CL domain of the paired light chain and the first and/or second selective recognition site comprises or consists of one or more of said residues. Residues located at the CH1/CL interface are typically defined as residues having a reduction in solvent accessibility of more than 40% when the CH1 domain and CL domain are paired (Rothlisberger et al. J. Mol. Biol. (2005) 347, 773-789). Tables 7 and 8 below identify the residues in the CH1 domain of an IgG1 and the CL domain of a kappa light chain, respectively, that exhibit a loss of more than 40% solvent accessibility when a CH1-CL domain pairing is formed. In certain embodiments, the first and second heavy chains differ by at least one amino acid residue in the CH1 domain that is not listed in Table 7 and/or the first and second light chains differ by at least one amino acid residue in the CL domain that is not listed in Table 8 and the first and/or second selective recognition site comprises or consists of one or more of said residues.

TABLE 7

Residues of CH1 buried in the CH1-CL domain interface (loss of more than 40% solvent accessibility when in complex) according to Rothlisberger et al. (J. Mol. Biol. (2005) 347, 773-789)

| | | CH1 | | |
|---|---|---|---|---|
| IMGT unique numbering for C-domains | IGHG1 amino acid translation[1] | IMGT exon numbering 1-98 | EU numbering (98 aa) 118-215 | Kabat numbering |
| 5 | F | 9 | 126 | 122 |
| 6 | P | 10 | 127 | 123 |
| 7 | L | 11 | 128 | 124 |
| 9 | P | 13 | 130 | 126 |
| 10 | S | 14 | 131 | 127 |
| 11 | S | 15 | 132 | 128 |
| 14 | T | 18 | 135 | 133 |
| 20 | A | 24 | 141 | 139 |
| 21 | L | 25 | 142 | 140 |
| 22 | G | 26 | 143 | 141 |
| 24 | L | 28 | 145 | 143 |
| 26 | K | 30 | 147 | 145 |
| 79 | H | 51 | 168 | 172 |
| 81 | F | 53 | 170 | 174 |
| 82 | P | 54 | 171 | 175 |
| 84 | V | 56 | 173 | 177 |

TABLE 7-continued

Residues of CH1 buried in the CH1-CL domain interface (loss of more than 40% solvent accessibility when in complex) according to Rothlisberger et al. (J. Mol. Biol. (2005) 347, 773-789)

| IMGT unique numbering for C-domains | IGHG1 amino acid translation[1] | CH1 IMGT exon numbering 1-98 | EU numbering (98 aa) 118-215 | Kabat numbering |
|---|---|---|---|---|
| 84.2 | Q | 58 | 175 | 179 |
| 85.1 | S | 64 | 181 | 186 |
| 86 | S | 66 | 183 | 188 |
| 88 | V | 68 | 185 | 190 |
| 119 | K | 96 | 213 | 221 |

TABLE 8

Residues of CL buried in the CH1-CL domain interface (loss of more than 40% solvent accessibility when in complex) according to Rothlisberger et al. (J. Mol. Biol. (2005) 347, 773-789)

| IMGT unique numbering for C-DOMAINs | IGKC amino acid translation | C-REGION IMGT exon numbering 1-107 | EU numbering (107 aa) 108-214 | Kabat numbering |
|---|---|---|---|---|
| 5 | F | 9 | 116 | 116 |
| 6 | I | 10 | 117 | 117 |
| 7 | F | 11 | 118 | 118 |
| 8 | P | 12 | 119 | 119 |
| 9 | P | 13 | 120 | 120 |
| 10 | S | 14 | 121 | 121 |
| 12 | E | 16 | 123 | 123 |
| 13 | Q | 17 | 124 | 124 |
| 20 | S | 24 | 131 | 131 |
| 22 | V | 26 | 133 | 133 |
| 24 | L | 28 | 135 | 135 |
| 26 | N | 30 | 137 | 137 |
| 27 | N | 31 | 138 | 138 |
| 79 | Q | 53 | 160 | 160 |
| 81 | S | 55 | 162 | 162 |
| 83 | T | 57 | 164 | 164 |
| 84.2 | D | 60 | 167 | 167 |
| 85.1 | S | 67 | 174 | 174 |
| 85 | L | 68 | 175 | 175 |
| 86 | S | 69 | 176 | 176 |
| 88 | T | 71 | 178 | 178 |
| 90 | T | 73 | 180 | 180 |
| 121 | F | 102 | 209 | 209 |
| 126 | C | 107 | 214 | 214 |

Alternatively or in addition, the multispecific antibodies of the invention may comprise first and second light chains wherein the amino acid sequence outside of the antigen binding site differs by at least one amino acid residue and the first and/or second selective recognition site comprises or consists of one or more of the residues that differ between the chains. In certain embodiments, the multispecific antibodies comprise first and second light chains wherein the amino acid sequences of the constant regions i.e. the CL domains, differ by at least one amino acid residue and the first and/or second selective recognition site comprises one or more of the residues that differ in the CL domain. In certain embodiments, the first and second light chains differ by at least one amino acid residue in the CL domain located outside of the interface between the CL domain of the light chain and the CH1 domain of the paired heavy chain and the first and/or second selective recognition site comprises or consists of one or more of said residues.

In preferred embodiments, the multispecific antibodies comprise first and second heavy chains that differ by at least one amino acid residue outside of the antigen binding sites and first and second light chains that differ by at least one amino acid residue outside of the antigen binding sites and the first and/or second selective recognition sites comprise or consist of residues that differ between both the heavy chains and the light chains. In particularly preferred embodiments, the first and second heavy chains differ by at least one amino acid residue in the CH1 domain and the first and second light chains differ by at least one amino acid residue in the CL domain and the first and/or second selective recognition sites comprise or consist of residues that differ between the CH1 domains of the heavy chains and the CL domains of the light chains. In particularly preferred embodiments, the residue(s) that differ between the first and second heavy chains and the residue(s) that differ between the first and second light chains are located outside of the binding interface between the CL domain and CH1 domain.

Naturally Occurring Variation in Immunoglobulin Heavy and Light Chains

One of the advantages of the present invention is that multispecific antibodies having at least two distinct selective recognition sites as defined above can be generated using combinations of naturally occurring heavy and light chains, and in particular heavy chains and light chains comprising at least the constant region of naturally occurring heavy and light chains. This minimises the need for extensive protein engineering and ensures that any unfavourable properties associated with mutated immunoglobulin sequences e.g. unwanted immunogenicity can be avoided. Furthermore, the use of naturally occurring heavy chains or fragments thereof in multispecific antibodies according to the present invention helps to preserve the natural effector function of the antibodies.

Heavy Chains

In certain embodiments, the multispecific antibodies as described herein comprise a first pairing comprising a first heavy chain of a particular immunoglobulin subtype and a second pairing comprising a second heavy chain of a different immunoglobulin subtype. In particular, provided herein are multispecific antibodies wherein at least the constant region of the first heavy chain and at least the constant region of the second heavy chain are derived from different immunoglobulin subtypes. The term "immunoglobulin subtype" is as defined elsewhere herein and is used interchangeably with the terms "immunoglobulin subclass" and "immunoglobulin isotype".

The different immunoglobulin subtypes are preferably from the same species and are preferably human. In a particular embodiment, the present invention provides a multispecific antibody comprising first and second heavy chain-light chain pairings as defined above wherein the first and second heavy chain each comprise the constant region of a different human immunoglobulin subtype and the different subtypes differ by at least one amino acid residue in the constant region, preferably in the CH1 domain.

In certain embodiments, the different immunoglobulin subtypes are selected from IgG1, IgG2, IgG3 and IgG4, preferably IgG1, IgG2, IgG3 and IgG4 of human origin. Polypeptide chains of different immunoglobulin subtypes, for example IgG1 and IgG2, differ in their amino acid sequence outside of the antigen binding site including in the constant region. Therefore, in embodiments wherein the first and second heavy chains are different immunoglobulin subtypes or comprise at least the constant region thereof, the first and/or second selective recognition sites can comprise or consist of one or more of the amino acid residues that differ at the corresponding position between the different subtypes. In certain embodiments, the first and/or second selective recognition sites comprise or consist of one or more of the amino acid residues that differ between the CH1 domains of the different immunoglobulin subtypes.

The present invention can also exploit the variation in the amino acid sequences of different immunoglobulin heavy chain allotypes, particularly human heavy chain allotypes. Therefore, in certain embodiments, the multispecific antibodies as provided herein comprise a first pairing with a first heavy chain of a particular immunoglobulin allotype and a second pairing with a second heavy chain of a different immunoglobulin allotype. In particular, provided herein are multispecific antibodies comprising first and second heavy chain-light chain pairings as defined above wherein at least the constant region of the first heavy chain and at least the constant region of the second heavy chain are derived from different immunoglobulin allotypes and the different allotypes differ by at least one amino acid residue in the constant region, preferably in the CH1 domain.

In preferred embodiments, the first and second heavy chains are different human immunoglobulin allotypes or comprise at least the constant region of different human immunoglobulin allotypes. For example, the first and second heavy chains may comprise at least the constant region of different human immunoglobulin allotypes selected from: IGGH1.1, IGGH1.3, IGGH2, IGGH2.2, IGGH2.4, IGGH4, IGGH3, IGG3.17 and IGGH3.18.

Similar to the situation concerning multispecific antibodies comprising heavy chains of different immunoglobulin subtypes, in embodiments wherein the first and second heavy chains are different immunoglobulin allotypes or comprise at least the constant region of different immunoglobulin allotypes, the first and/or second selective recognition sites may comprise or consist of one or more amino acid residues that naturally differ at the corresponding position between the different allotypes. In preferred embodiments, the first and/or second selective recognition site comprises or consists of one or more amino acid residues within the CH1 domain that differs at the corresponding position between the different immunoglobulin allotypes.

Figure 3:
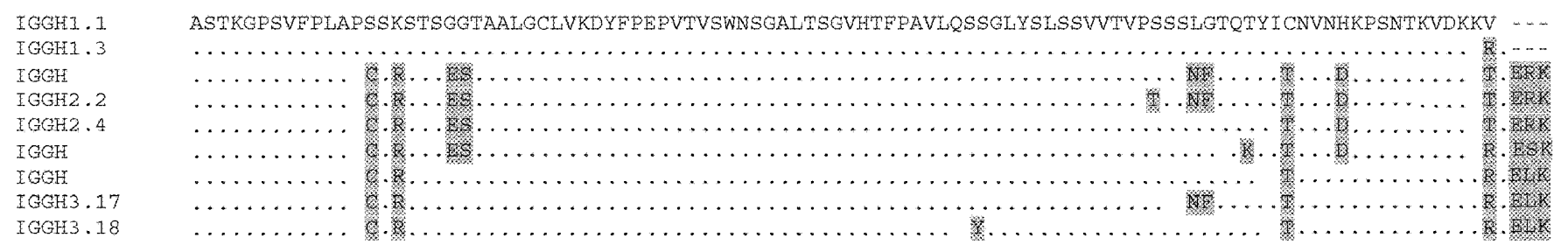

The sequences of the CH1 domains found within some of the different human IgG heavy chain allotypes are shown in Table 9 and an alignment of the sequences is shown in FIG. 3 with natural variation indicated at amino acid positions 131, 133, 137, 138, 178, 189, 192, 193, 196, 199, 203 and 214 of the sequences (based on EU numbering).

TABLE 9

CH1 sequences of different human immunoglobulin allotypes

| Allotype | CH1 amino acid sequence | SEQ ID NO. |
|---|---|---|
| IGGH1.1 | ASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKKV | 1 |
| IGGH1.3 | ASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKRV | 2 |
| IGGH2 | ASTKGPSVFPLAPCSRSTSESTAALGCLVKDYFPEPVTVSWNSGALTSGVHT FPAVLQSSGLYSLSSVVTVPSSNFGTQTYTCNVDHKPSNTKVDKTVERK | 3 |
| IGGH2.2 | ASTKGPSVFPLAPCSRSTSESTAALGCLVKDYFPEPVTVSWNSGALTSGVHT FPAVLQSSGLYSLSSVVTVTSSNFGTQTYTCNVDHKPSNTKVDKTVERK | 4 |
| IGGH2.4 | ASTKGPSVFPLAPCSRSTSESTAALGCLVKDYFPEPVTVSWNSGALTSGVHT FPAVLQSSGLYSLSSVVTVPSSSLGTQTYTCNVDHKPSNTKVDKTVERK | 5 |
| IGGH4 | ASTKGPSVFPLAPCSRSTSESTAALGCLVKDYFPEPVTVSWNSGALTSGVHT FPAVLQSSGLYSLSSVVTVPSSSLGTKTYTCNVDHKPSNTKVDKRVESK | 6 |
| IGGH3 | ASTKGPSVFPLAPCSRSTSGGTAALGCLVKDYFPEPVTVSWNSGALTSGVHT FPAVLQSSGLYSLSSVVTVPSSSLGTQTYTCNVNHKPSNTKVDKRVELKTPL GDTTHT | 7 |
| IGG3.17 | ASTKGPSVFPLAPCSRSTSGGTAALGCLVKDYFPEPVTVSWNSGALTSGVHT FPAVLQSSGLYSLSSVVTVPSSNFGTQTYTCNVNHKPSNTKVDKRVELKTPL GDTTHT | 8 |
| IGGH3.1 | ASTKGPSVFPLAPCSRSTSGGTAALGCLVKDYFPEPVTVSWNSGALTSGVHT FPAVLQYSGLYSLSSVVTVPSSSLGTQTYTCNVNHKPSNTKVDKRVELKTPL GDTTHT | 9 |

The multispecific antibodies of the invention may comprise or consist of first and second heavy chain amino acid residues selected from the following:

(i) at position 131: C in the first heavy chain; S in the second heavy chain; and/or
(ii) at position 133: R in the first heavy chain; K in the second heavy chain; and/or
(iii) at position 137: E in the first heavy chain; G in the second heavy chain; and/or
(iv) at position 138: S in the first heavy chain; G in the second heavy chain; and/or
(v) at position 178: S in the first heavy chain; Y in the second heavy chain; and/or
(vi) at position 192: N in the first heavy chain; S in the second heavy chain; and/or
(vii) at position 193: F in the first heavy chain; L in the second heavy chain.

In preferred embodiments, multispecific antibodies of the invention comprise or consist of a first heavy chain comprising or consisting of E at position 137 and S at position 138, and a second heavy chain comprising or consisting of G at position 137 and G at position 138. In preferred embodiments, multispecific antibodies of the invention comprise or consist of a first heavy chain comprising or consisting of N at position 192 and F at position 193, and a second heavy chain comprising or consisting of S at position 192 and L at position 193.

Figure 7:
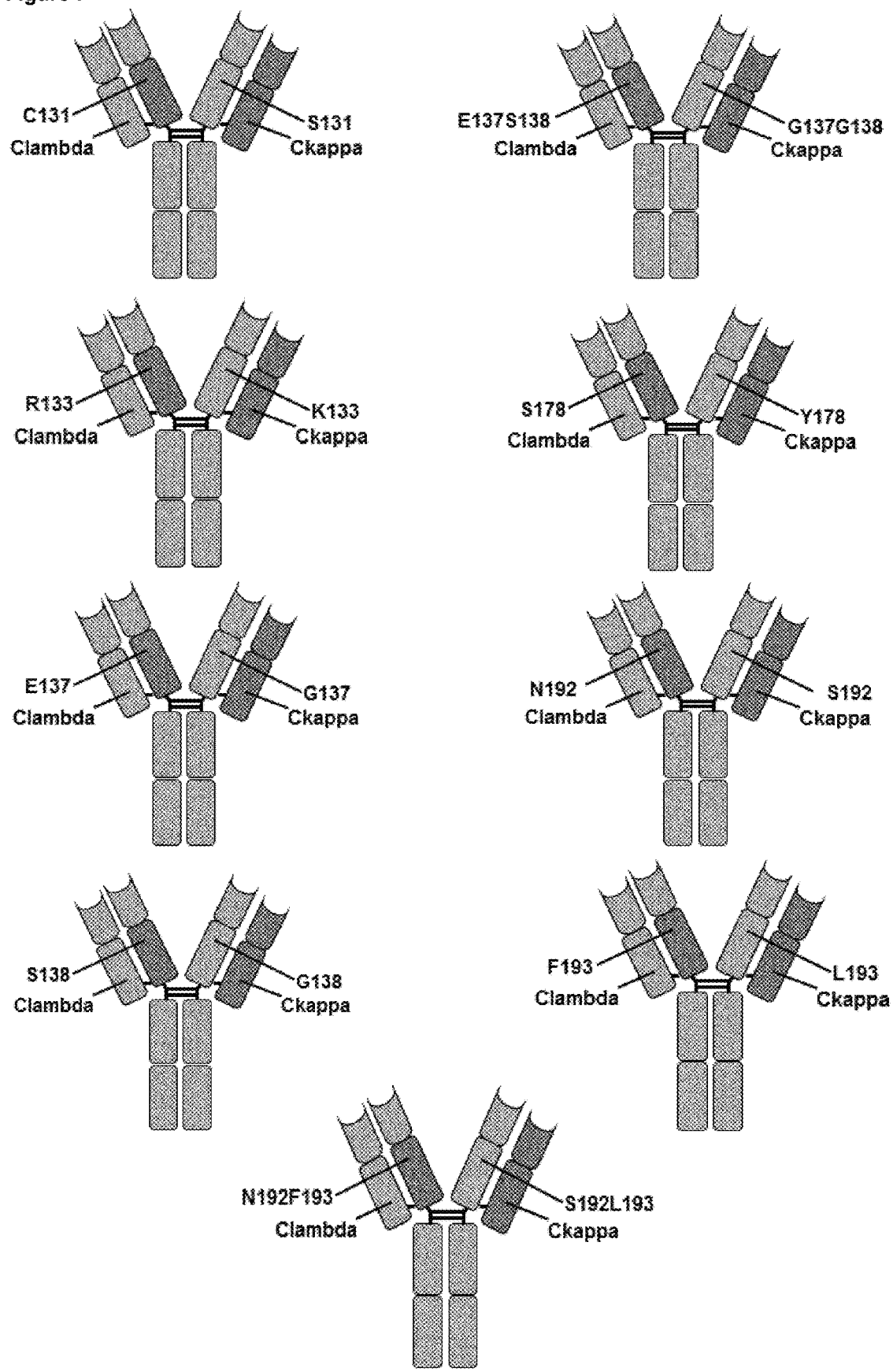
FIG. 7 Exemplary bispecific antibodies of the invention having CH1 domains that differ by at least one amino acid residue and CL domains that differ by virtue of the fact that they are derived from the lambda and kappa light chains.

Exemplary bispecific antibodies of the invention are shown in FIG. 7. The differences in the CH1 domains of the antibodies are shown in combination with first and second lambda and kappa light chains. However, it will be appreciated that the lambda and kappa chains could be reversed such that the different CH1 domains are paired with a light chain of the opposite class. For example, in the first embodiment shown, the CH1 domain comprising the C131 residue is shown paired with a Clambda domain and the S131 residue is shown paired with a Ckappa domain. However, this pairing could be reversed such that the CH1 domain comprising the C131 residue is paired with the Ckappa domain and the CH1 domain comprising the S131 residue is paired with the Clambda domain.

In certain embodiments, wherein multispecific antibodies of the invention comprise a first heavy chain and a different second heavy chain, each having at least a constant region selected from the human immunoglobulin allotypes: IGGH1.1, IGGH1.3, IGGH2, IGGH2.2, IGGH2.4, IGGH4, IGGH3, IGG3.17 and IGGH3.18, the first and/or second selective recognition sites may comprise one or more residues selected from positions: 131, 133, 137, 138, 178, 189, 192, 193, 196, 199, 203 and 214 of the CH1 domain, preferably positions 131, 133, 137, 138, 178, 192 and 193 of the CH1 domain.

Figure 4:
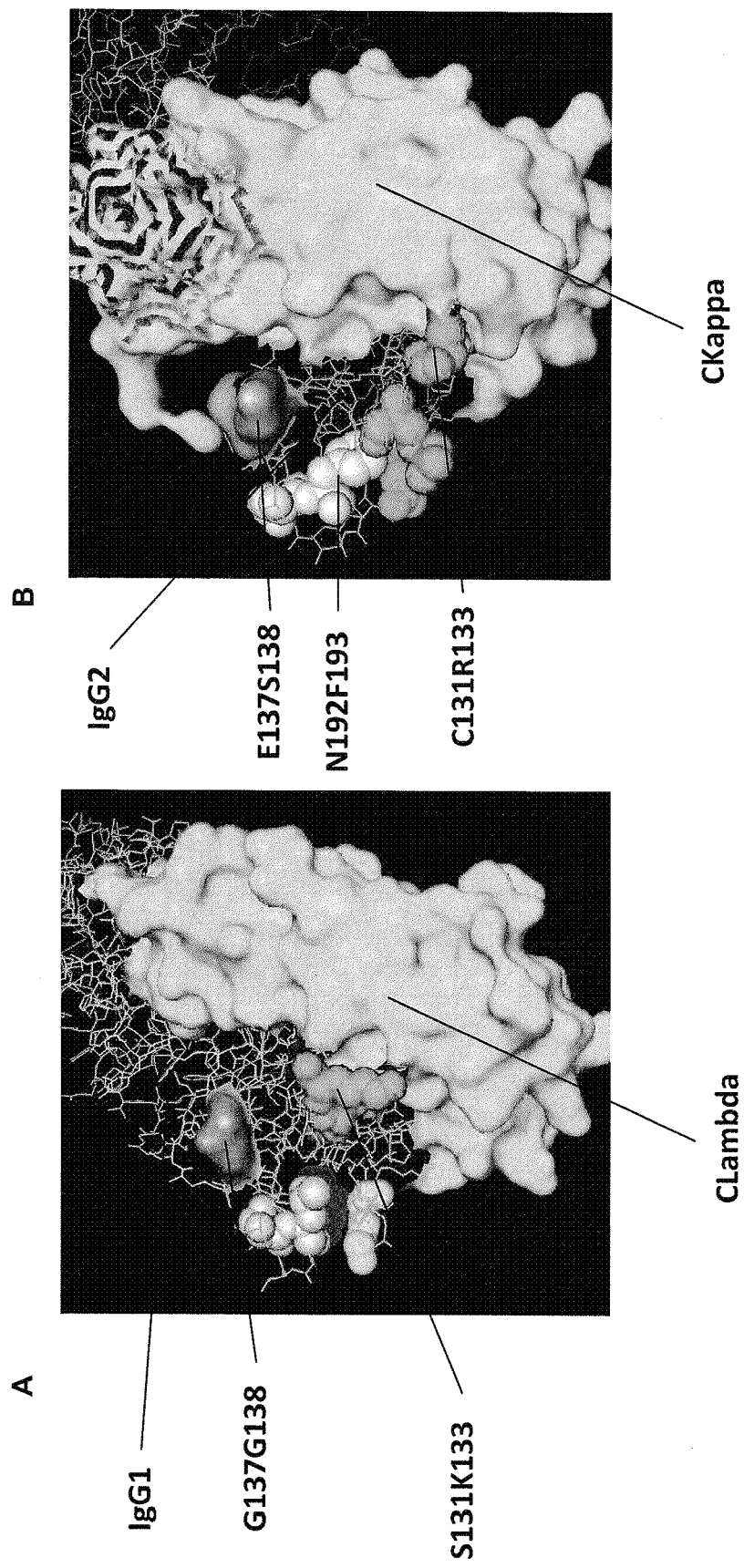
FIG. 4 Crystal structure of human IgG heavy chain CH1 domains paired with human light chain CL domains. (A) CH1 domain of an IgG1 molecule paired with the CL domain of a lambda light chain; (B) CH1 domain of an IgG2 molecule paired with the CL domain of a kappa light chain.

The amino acid residues of the heavy chain constant region in close spatial proximity to the constant region of the paired light chain are preferred residues for contributing to the selective recognition site. Exemplary residues are indicated in the space fill model shown in FIG. 4. In certain embodiments, the first and second selective recognition sites, respectively, comprise or consist of heavy chain residues selected from the following:

(i) at position 131: C in the first heavy chain; S in the second heavy chain; and/or
(ii) at position 133: R in the first heavy chain; K in the second heavy chain; and/or
(iii) at position 137: E in the first heavy chain; G in the second heavy chain; and/or
(iv) at position 138: S in the first heavy chain; G in the second heavy chain; and/or
(v) at position 178: S in the first heavy chain; Y in the second heavy chain; and/or
(vi) at position 192: N in the first heavy chain; S in the second heavy chain; and/or
(vii) at position 193: F in the first heavy chain; L in the second heavy chain.

In preferred embodiments, the first and second selective recognition sites, respectively, comprise or consist of combinations of heavy chain residues selected from the following:

(i) E at position 137 and S at position 138 in the first heavy chain and G at position 137 and G at position 138 in the second heavy chain; and/or
(ii) N at position 192 and F at position 193 in the first heavy chain and S at position 192 and L at position 193 in the second heavy chain.

As noted above, exemplary bispecific antibodies of the invention are shown in FIG. 7 and the residues indicated in the CH1 domains that differ between the heavy chains may contribute to the first and/or second selective recognition sites, respectively.

The positions of the amino acid residues in the heavy chains are identified above with reference to the EU numbering scheme as applied to human IgG1 molecules (see Table 2). It would be within the capabilities of the skilled person to align the amino acid sequence of a human IgG1 heavy chain with the amino acid sequence of a different heavy chain in order to identify equivalent or corresponding residues. These equivalent or corresponding residues are within the scope of the present invention.

Light Chains

Alternatively or in addition to naturally occurring heavy chains, multispecific antibodies of the invention may comprise first and second light chains of different immunoglobulin classes or different immunoglobulin allotypes. In particular, provided herein are multispecific antibodies wherein at least the constant region of the first light chain and at least the constant region of the second light chain are derived from different immunoglobulin classes or allotypes.

In certain embodiments, multispecific antibodies of the invention comprise a lambda light chain as the first light chain and a kappa light chain as the second light chain or a kappa light chain as the first light chain and lambda light chain as the second light chain. The lambda and/or kappa light chains, or at least the constant regions thereof, are preferably human lambda and/or kappa light chains. In embodiments wherein the antibody comprises a first lambda light chain and a second kappa light chain, the first selective recognition site may comprise one or more residues specific to the lambda light chain and/or the selective recognition site may comprise one or more residues specific to the kappa light chain. As used herein, a residue "specific" to the kappa or lambda light chain is a residue located at a position within the polypeptide amino acid sequence that differs from the amino acid residue located at the corresponding position within the polypeptide sequence of the other class of light chain.

As an alternative to antibodies comprising light chains of different classes, the multispecific antibodies as provided herein may comprise a first pairing having a first light chain of a particular immunoglobulin allotype and a second pairing having a second light chain of a different immunoglobulin allotype. In certain embodiments, at least the constant region of the first light chain and at least the constant region of the second light chain are derived from different immunoglobulin allotypes. In preferred embodiments, the first and second light chains are different human immunoglobulin allotypes, optionally selected from different kappa or lambda allotypes. For example, the first and second light chains or at least the constant regions thereof may be different human immunoglobulin allotypes selected from the human lambda chain allotypes: IGLC1*01, IGLC2*01, IGLC3*01, IGLC7*01, IGLC6*01.

As described above for multispecific antibodies comprising heavy chains of different allotypes, in embodiments wherein the first and second light chains are different immunoglobulin allotypes or comprise at least the constant region of different immunoglobulin allotypes, the first and/or second selective recognition sites may comprise or consist of one or more amino acid residues that naturally differ at the corresponding position between the different allotypes. In preferred embodiments, the first and/or second selective recognition site comprises or consists of one or more amino acid residues within the CL domain that differs between the different immunoglobulin allotypes. The sequences of the CL domains found within some of the different human lambda chain allotypes are shown in Table 10 and an alignment of the sequences is shown in FIG. 5.

TABLE 10

CL sequences of different human lambda immunoglobulin allotypes

| Allotype | CL amino acid sequence | SEQ ID NO. |
|---|---|---|
| IGLC1*01 | PKANPTVTLFPPSSEELQANKATLVCLISDFYPGAVTVAWKADGSPVKA GVETTKPSKQSNNKYAASSYLSLTPEQWKSHRSYSCQVTHEGSTVEKTV APTECS | 10 |
| IGLC2*01 | GQPKAAPSVTLFPPSSEELQANKATLVCLISDFYPGAVTVAWKADSSPV KAGVETTTPSKQSNNKYAASSYLSLTPEQWKSHRSYSCQVTHEGSTVEK TVAPTECS | 11 |
| IGLC3*01 | QPKAAPSVTLFPPSSEELQANKATLVCLISDFYPGAVTVAWKADSSPVK AGVETTTPSKQSNNKYAASSYLSLTPEQWKSHRSYSCQVTHEGSTVEKT VAPTECS | 12 |
| IGLC7*01 | GQPKAAPSVTLFPPSSEELQANKATLVCLVSDFYPGAVTVAWKADGSPV KVGVETTKPSKQSNNKYAASSYLSLTPEQWKSHRSYSCRVTHEGSTVEK TVAPAECS | 13 |
| IGLC6*01 | GQPKAAPSVTLFPPSSEELQANKATLVCLISDFYPGAVKVAWKADGSPV NTGVETTTPSKQSNNKYAASSYLSLTPEQWKSHRSYSCQVTHEGSTVEK TVAPAECS | 14 |

The multispecific antibodies of the invention may comprise or consist of first and second light chain amino acid residues selected from the following:
 (i) at position 112: N in the first light chain; A in the second light chain; and/or
 (ii) at position 114: T in the first light chain; S in the second light chain; and/or
 (iii) at position 212: T in the first light chain; A in the second light chain.

Figure 6:
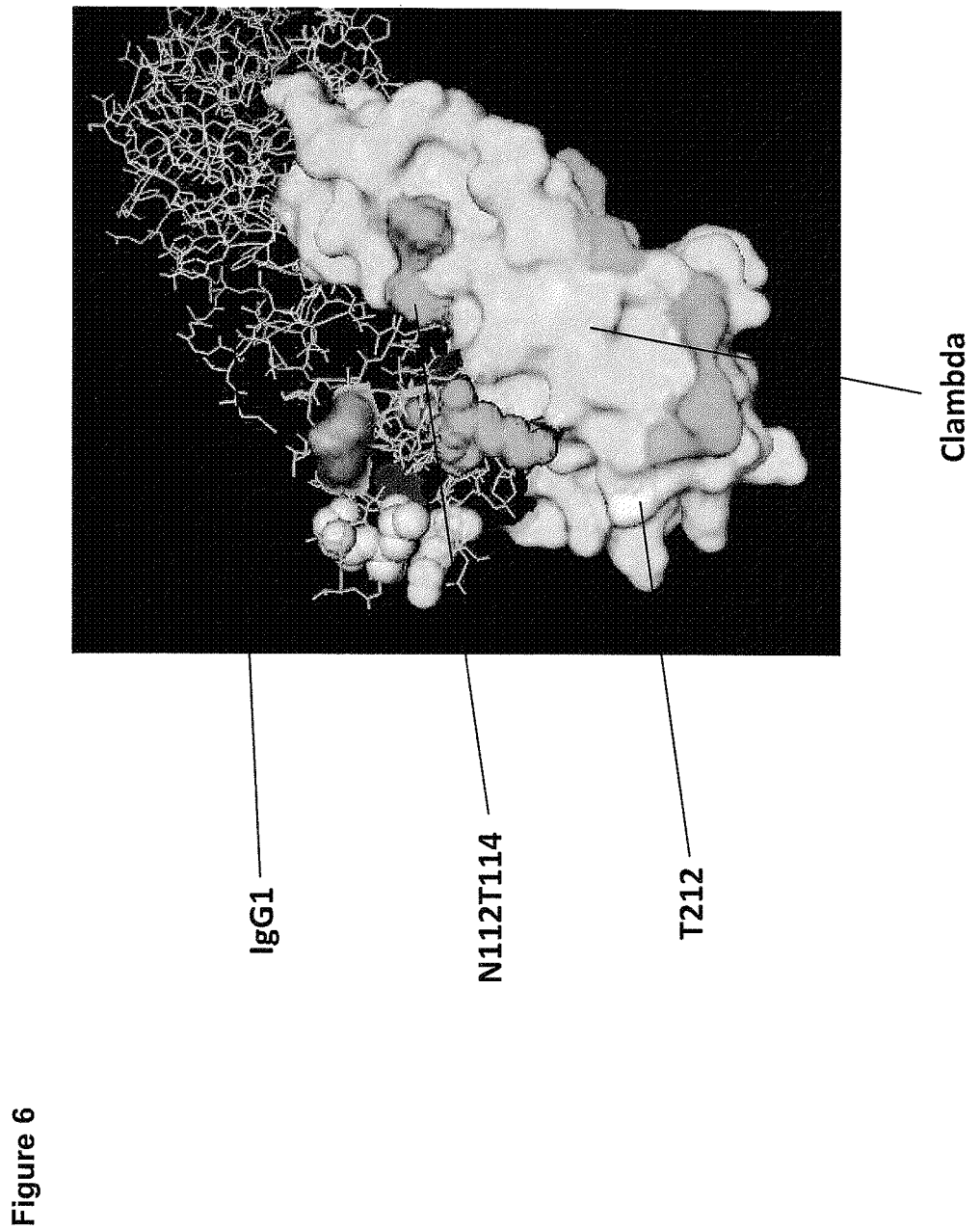
FIG. 6 Crystal structure of the CL domain of the human lambda light chain paired with the CH1 domain of human IgG1.

In certain embodiments, wherein multispecific antibodies of the invention comprise a first light chain and a different second light chain, each selected from the human immunoglobulin allotypes: IGLC1*01, IGLC2*01, IGLC3*01, IGLC7*01, IGLC6*01, the first and/or second selective recognition sites may comprise or consist of one or more residues selected from positions 112, 114 and 212. As shown in the space fill model in FIG. 6, these residues are in close spatial proximity to the CH1 domain of the paired heavy chain and are preferred residues for contributing to the selective recognition site.

In certain embodiments, the first and second selective recognition sites, respectively, include light chain residues selected from the following:
 (i) at position 112: N in the first light chain; A in the second light chain; and/or
 (ii) at position 114: T in the first light chain; S in the second light chain; and/or
 (iii) at position 212: T in the first light chain; A in the second light chain.

The positions of the amino acid residues in the light chain are identified with reference to the numbering scheme developed by Kabat et al. as applied to human lambda light chains (see Table 6). It would be within the capabilities of the skilled person to align the amino acid sequence of a human lambda light chain with the amino acid sequence of a different light chain in order to identify equivalent or corresponding residues. These equivalent or corresponding residues are within the scope of the present invention.

In preferred embodiments of the present invention, the multispecific antibody comprises a first heavy chain comprising at least the constant region of a particular immunoglobulin allotype, preferably a human allotype, and a second heavy chain comprising at least the constant region of a different immunoglobulin allotype, preferably a human allotype, wherein the allotypes differ by at least one amino acid residue in the CH1 domain, and further comprises a lambda light chain, wherein at least the constant region is preferably human, as the first light chain and a kappa light chain, wherein at least the constant region is preferably human, as the second light chain. In such embodiments, the first and/or second selective recognition sites comprise or consist of one or more residues that differ between the heavy chain allotypes, preferably in the constant region, more preferably in the CH1 domain, and one or more residues that are specific to the lambda/kappa light chains, preferably in the CL domain.

Modified Antibodies

The multispecific antibodies of the present invention can be modified, as compared with naturally occurring immunoglobulin molecules, in a number of different ways. Described below are various modifications and modified antibody forms/structures that are applicable to multispecific antibodies according to all aspects of the invention described herein.

Antibodies Incorporating Fragments and/or Amino Acid Substitutions from Naturally Occurring Immunoglobulin Chains In addition to naturally occurring immunoglobulin chains and constant regions derived therefrom, the multispecific antibodies of the present invention may include immunoglobulin chains incorporating fragments derived from different naturally occurring immunoglobulin chains and/or immunoglobulin chains from different species. As used herein, a "fragment derived from" a particular polypeptide is a length of amino acids with a sequence identical to or substantially identical to a sequence of amino acids in the originating polypeptide.

The immunoglobulin chains of the multispecific antibodies described herein may be full length as compared with naturally occurring immunoglobulin heavy and/or light chains and "incorporate a fragment" such that a region of the full length immunoglobulin chain backbone is substituted with the fragment. The fragment will typically correspond to the region equivalent to the substituted region located within the originating polypeptide. The immunoglobulin chains of the multispecific antibodies described herein may thus be composite immunoglobulin chains incorporating fragments derived from different immunoglobulin chains into a full-length polypeptide chain (see FIG. 8A).

Alternatively, the immunoglobulin chains of the multispecific antibodies described herein may be truncated, as described further below, and incorporate fragments shorter in length than the overall heavy chain/light chain length. Such truncated chains may also be composite chains incorporating fragments derived from different immunoglobulin chains.

The multispecific antibodies of the invention may comprise first and second heavy chains wherein the first heavy chain comprises a fragment derived from a particular immunoglobulin subtype or allotype and the second heavy chain comprises a corresponding fragment derived from the same region of a different immunoglobulin subtype or allotype, including but not limited to the immunoglobulin subtypes and allotypes described elsewhere herein. Alternatively or in addition, the multispecific antibodies of the present invention may comprise first and second light chains wherein the first light chain comprises a fragment derived from a particular immunoglobulin class (kappa or lambda) or allotype and the second light chain comprises a corresponding fragment derived from the same region of a different immunoglobulin class (kappa or lambda) or allotype, including but not limited to the immunoglobulin allotypes described elsewhere herein.

The position and length of each fragment may be selected such that it includes at least some of the natural variation i.e. amino acid differences, found at particular positions of naturally occurring different immunoglobulin classes, subtypes and allotypes. For example, the human IgG subtypes and allotypes shown in FIG. 3 exhibit variation at positions 131, 133, 137, 138, 178, 189, 192, 193, 196, 199, 203 and 214. Therefore, a fragment incorporated into the first heavy chain may comprise or consist of a region incorporating at least one of the residues identified above derived from a first human IgG subtype or allotype and a fragment incorporated into the second heavy chain may comprise or consist of a region incorporating at least one of the residues identified above derived from a second human IgG subtype or allotype and having at least one amino acid difference located in this region.

Figure 8:
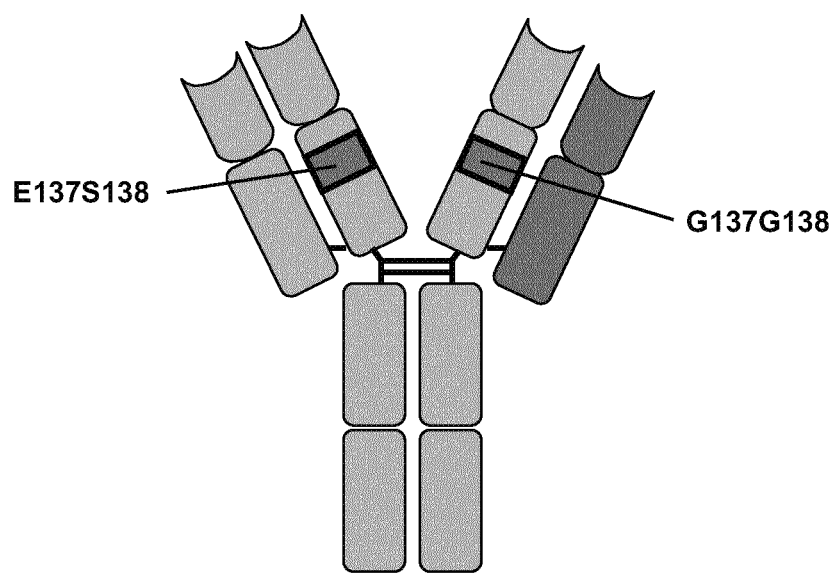
FIG. 8 (A) An exemplary composite bispecific IgG antibody of the invention incorporating fragments derived from the CH1 domains of different human immunoglobulin heavy chain allotypes. The fragments comprise residues 137 and 138 of the heavy chain allotypes, wherein the amino acids at positions 137 and 138 differ between the allotypes. (B) An exemplary bispecific IgG antibody of the invention incorporating amino acid substitutions derived from naturally occurring human immunoglobulin allotypes in the CH1 domains of the heavy chains.
Figure 8:
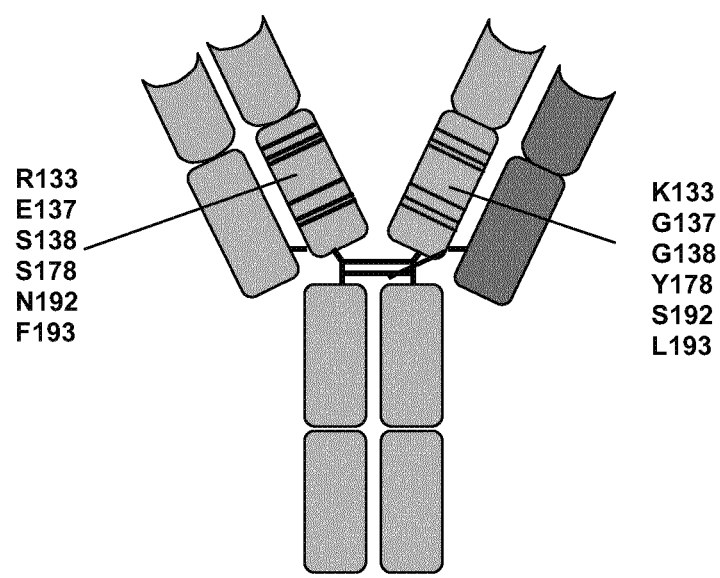

An exemplary composite bispecific IgG antibody according to the present invention is shown schematically in FIG. 8A. This bispecific antibody has a first IgG heavy chain backbone incorporating a fragment derived from the CH1 domain of a first human IgG allotype and a second IgG heavy chain backbone incorporating a fragment derived from the CH1 domain of a second human IgG allotype. The fragment incorporated into the first chain includes residues E137 and S138 and the fragment incorporated in the second chain includes residues G137 and G138. These differences in the CH1 domains allow the first and second heavy chains to be distinguished or differentiated from each other.

The first and second light chains may also include fragments as described above, for example fragments derived from different human allotypes. The human lambda allotypes shown in FIG. 5 exhibit variation i.e. amino acid differences, for example at positions 112 and 114. Therefore, a fragment incorporated into the first light chain may comprise or consist of a region including one or both of these positions from a first human lambda allotype and a fragment incorporated into the second light chain may comprise or consist of a region including one or both of these positions from a second human lambda allotype wherein there is at least one amino acid difference between the allotypes. It would be within the capabilities of a person skilled in the art to identify suitable fragments from naturally occurring heavy and light chain immunoglobulin classes, subtypes and/or allotypes which incorporate similar amino acid sequence variation and engineer multispecific antibodies incorporating such fragments so as to generate antibodies having amino acid sequence variation outside of the antigen binding site, preferably in the constant regions, between the first and second heavy chain-light chain pairings.

A fragment according to the present invention may have a length of at least 2, at least 3, at least 4, at least 5, at least 6, at least 7, at least 8, at least 9, at least 10 residues wherein the position of the fragment is selected such that the corresponding fragment derived from a different immunoglobulin class, subtype or allotype has an amino acid sequence differing by at least one amino acid residue. In certain embodiments, a fragment derived from an immunoglobulin chain and in particular, a human immunoglobulin chain may be at least 20, at least 40, at least 50, at least 60, at least 70, at least 80, at least 90, at least 100, at least 110, at least 120, at least 130, at least 140, at least 150, at least 160, at least 170, at least 180, at least 190 or at least 200 amino acids in length. A fragment may also comprise or consist of a complete domain derived from the immunoglobulin chain wherein the domain is selected from the CH1, CH2 or CH3 domain of the heavy chain or the CL domain of the light chain. In preferred embodiments, the fragments inserted into the heavy chains comprise or consist of the entire CH1 domain and the fragments inserted into the light chains comprise or consist of the entire CL domain.

For antibodies of the invention comprising fragments that produce one or more amino acid sequence differences between the first and second heavy chains and/or the first and second light chains, the first and/or second selective recognition sites may comprise one or more of the residues that differ between the fragments. Therefore, the introduction of distinct fragments from naturally occurring immunoglobulin heavy and light chains can be used to create the distinct first and second selective recognition sites within the multispecific antibodies of the invention.

Alternatively, or in addition to the embodiments described above, multispecific antibodies according to the present invention may comprise immunoglobulin chains including one or more amino acid substitutions derived from different naturally occurring immunoglobulin chains and/or immunoglobulin chains from different species. In particular, multispecific antibodies may comprise or consist of heavy chains and/or light chains wherein a particular amino acid in the heavy and/or light polypeptide chain is substituted with a different amino acid that is found at the corresponding position in a different immunoglobulin class, subtype or allotype.

The amino acid substitutions introduced into the heavy and/or light chains of the multispecific antibodies of the present invention may derive from any naturally occurring immunoglobulin chains, preferably immunoglobulin chains of human origin, including but not limited to the immunoglobulin classes, subtypes and allotypes described elsewhere herein.

In certain embodiments, the multispecific antibodies of the invention comprise or consist of first and second heavy chains wherein the first heavy chain comprises one or more amino acid substitution(s) derived from a particular immunoglobulin subtype or allotype and the second heavy chain comprises one or more amino acid substitution(s) from a different immunoglobulin subtype or allotype, wherein the substitutions create differences between the amino acid sequences of the first and second heavy chains. Preferably, the amino acid substitution(s) are located in the CH1 domains of the heavy chains. Alternatively or in addition, the multispecific antibodies may comprise first and second light chains wherein the first light chain comprises one or more amino acid substitution(s) derived from a particular immunoglobulin class (kappa or lambda) or allotype and the second light chain comprises one or more amino acid substitution(s) derived from a different immunoglobulin class (kappa or lambda) or allotype, wherein the substitutions create differences between the amino acid sequences of the first and second light chains. Preferably, the amino acid substitution(s) are located in the CL domains of the light chains.

In certain embodiments, the heavy chains and/or light chains comprise or consist of combinations of amino acid substitutions derived from naturally occurring immunoglobulin chains such that the first and second heavy chains and/or first and second light chains differ in amino acid sequence at the substituted positions. A "combination" of amino acid substitutions may include at least 2, 3, 4, 5, 6, 7 amino acid substitutions, wherein the substitutions occur at contiguous or non-contiguous locations in the polypeptide chains.

An exemplary bispecific IgG antibody according to the present invention is shown schematically in FIG. 8B. This bispecific antibody has a first IgG heavy chain including the amino acid substitutions R133, E137, S138, S178, N192, F193 and a second IgG heavy chain including the amino acid substitutions K133, G137, G138, Y178, S192, L193. These amino acid substitutions derive from the naturally occurring human IgG allotypes shown in FIG. 3. Multispecific antibodies of the invention may comprise or consist of amino acid substitutions derived from any of the immunoglobulin allotypes described elsewhere herein and in preferred embodiments include amino acid substitutions corresponding to the amino acid differences between first and second heavy chains shown in FIG. 7.

In certain embodiments, multispecific antibodies comprise or consist of first and second heavy chain amino acid substitutions selected from the following:
 (i) at position 131: C in the first heavy chain; S in the second heavy chain; and/or
 (ii) at position 133: R in the first heavy chain; K in the second heavy chain; and/or
 (iii) at position 137: E in the first heavy chain; G in the second heavy chain; and/or
 (iv) at position 138: S in the first heavy chain; G in the second heavy chain; and/or
 (v) at position 178: S in the first heavy chain; Y in the second heavy chain; and/or
 (vi) at position 192: N in the first heavy chain; S in the second heavy chain; and/or
 (vii) at position 193: F in the first heavy chain; L in the second heavy chain.

In preferred embodiments, multispecific antibodies comprise or consist of first and second heavy chain amino acid substitutions selected from the following:
 (i) E at position 137 and S at position 138 in the first heavy chain and G at position 137 and G at position 138 in the second heavy chain;
 (ii) N at position 192 and F at position 193 in the first heavy chain and S at position 192 and L at position 193 in the second heavy chain;
 (iii) R at position 133, E at position 137, S at position 138, S at position 178, N at position 192 and F at position 193 in the first heavy chain and K at position 133, G at position 137, G at position 138, Y at position 178, S at position 192 and L at position 193 in the second heavy chain.

For antibodies of the invention comprising amino acid substitutions that produce one or more amino acid sequence differences between the first and second heavy chains and/or the first and second light chains, the first and/or second selective recognition sites may comprise one or more of the substituted residues. Therefore, the introduction of distinct amino acid substitutions from naturally occurring immunoglobulin heavy and light chains can be used to create the distinct first and second selective recognition sites within the multispecific antibodies of the invention.

Mutations Affecting the Selective Recognition Sites

Alternatively or in addition to the natural variation found in the amino acid sequences of naturally occurring immunoglobulin heavy and light chains, the heavy and/or light chains incorporated into the multispecific antibodies described herein may be mutated. In particular, mutations may be introduced into the first and/or second heavy chain outside of the antigen binding site, preferably in the constant region, more preferably in the CH1 domain, so as to create at least one difference or at least one further difference (in addition to any natural variation) between the amino acid residues at the corresponding positions of the amino acid sequences of the first and second heavy chains. Alternatively or in addition, mutations may be introduced into the first and/or second light chain outside of the antigen binding site, preferably in the constant region i.e. the CL domain, so as to create at least one difference or at least one further difference (in addition to any natural variation) between the amino acid residues at the corresponding positions of the first and second light chains. These mutations may be mutations not found in naturally occurring immunoglobulin chains. In certain embodiments, the multispecific antibodies of the present invention comprise or consist of first and second heavy chains and/or first and second light chains wherein the amino acid differences between the heavy chains and/or the amino acid differences between the light chains represent a combination of natural variation between the amino acid sequences of the chains and the presence of one or more amino acid substitutions or engineered mutations not found in naturally occurring immunoglobulin chains.

The mutations may be introduced in solvent-exposed regions of the heavy and/or light chains. Alternatively or in addition, the mutations may be introduced in regions of the heavy and/or light chain outside of the binding interface between the CH1 and CL domains of the heavy chain-light chain pairing as defined elsewhere herein. Techniques for introducing mutations into the polynucleotide sequences encoding the heavy chain and/or the light chain polypeptides are known in the art and could readily be used by a person skilled in the art to produce antibodies according to the invention.

For embodiments in which the first and/or second heavy chain has been mutated to produce at least one difference in the amino acid sequence of the heavy chains outside of the antigen binding site, preferably within the constant region, the first and/or second selective recognition site may comprise one or more of the amino acid residues that differ between the heavy chains. Alternatively or in addition, for embodiments in which the first and/or second light chain has been mutated to create at least one difference in the amino acid sequence of the light chains outside of the antigen binding site, preferably within the constant domain, the first and/or second selective recognition site may comprise one or more of the amino acid residues that differ between the light chains. In preferred embodiments, the first and/or second selective recognition sites comprise or consist of amino acid residues that differ between first and second heavy chains and first and second light chains.

In certain embodiments, the first and/or second selective recognition site comprises or consists of amino acid residues that differ between first and second heavy chains wherein the site comprises or consists of at least one residue that differs due to natural variation between the immunoglobulin chains and at least one residue that has been substituted or mutated so as to create a difference between first and second heavy chains. Alternatively or in addition, the first and/or second selective recognition sites may comprise or consist of amino acid residues that differ between first and second light chains wherein the site comprises or consists of at least one residue that differs due to natural variation between the immunoglobulin chains and at least one residue that has been substituted or mutated so as to create a difference between first and second light chains.

Additional Features and Mutations

The heavy and light chain polypeptides of the multispecific antibodies of the present invention may derive from any source including heavy and light chain polypeptides of mouse, rat, rabbit, goat, hamster, chicken, monkey or human origin. In certain embodiments, the multispecific antibodies of the invention may be derived from the Camelidae family and in particular llama (*Lama glama*).

The multispecific antibodies of the present invention may incorporate chimeric, humanised or substantially humanised variants of antibodies (as defined elsewhere herein), wherein portions of the multispecific antibody, and in particular portions or regions of the different immunoglobulin chains, are derived from different sources. For example, multispecific antibodies of the present invention may comprise at least one camelid derived domain, preferably a camelid-derived VH and/or VL domain. The camelid-derived domain(s) may incorporate humanising substitutions as described in WO2011/080350, the contents of which are incorporated herein in their entirety.

The present invention encompasses chimeric antibodies having VH and/or VL domains derived from any species including but not limited to antibodies of mouse, rat, rabbit, goat, hamster, chicken, monkey or human origin, and heavy chain and/or light chain constant regions derived from antibodies of another species. In preferred embodiments, the VH and/or VL domains are camelid-derived and the constant regions of the heavy and/or light chains are substantially human.

The multispecific antibodies of the present invention may also be engineered so as to incorporate mutations or modifications which have previously been reported to address the problem of multispecific antibody chain mispairing. For example, the CH3 domains of the first and second heavy chains may be engineered to include the "knobs into holes" mutations reported in (Carter P. J. Immunol. Methods (2001) 248: 7-15), which promote correct heavy chain heterodimerization in the Fc region. The VH and VL domains and/or CH1 and CL domains may also be engineered as described in Lewis et al. (Nature Biotechnology (2014) 32: 191-198) so as to promote the correct pairing between the heavy and light chains of the antibody molecule.

The antibodies of the invention may further comprise additional modifications, for example modifications to improve properties such as antigen binding, effector function and/or stability/half-life and/or reduce unfavourable properties such as immunogenicity in a human host. The antibodies of the invention may comprise any of the mutations or combinations of amino acid residues described in WO2006/130834 (the contents of which are incorporated herein in their entirety). These include the combination of mutations: Lys433, Phe434, Tyr436 in the CH3 domain of the heavy chain, which together can enhance the binding affinity of the antibody for the FcRn receptor and therefore can help to prolong the serum half life of the antibody.

The additional mutations or modifications described above, either to address the issue of chain mispairing or to alter the properties of the antibodies described herein, do not contribute to or affect the selective recognition sites.

Multispecific Antibodies Having Native Structure

Multispecific antibodies of the present invention may comprise full length heavy chains and/or full length light chains, wherein "full-length" is used herein to mean that the amino acid sequence of the immunoglobulin chain is essentially identical in length to the length of a naturally occurring heavy and/or light chain.

The antibodies may comprise first and second heavy chain-light chain pairings wherein the antigen binding site of each pairing recognises a different epitope (on the same or different antigens) and the antibody is monovalent for each epitope. In preferred embodiments, the antibodies as described herein are bispecific and/or have the standard domain structure shown in FIG. 2 for bispecific antibodies having first and second heavy chain-light chain pairings i.e. a domain structure of VH-CH1-hinge-CH2-CH3 for the first and second heavy chains, and a domain structure of VL-CL for the first and second light chains. In further preferred embodiments, the antibodies of the invention are IgG molecules and/or have the structure of a native or naturally-occurring IgG molecule.

Truncated Multispecific Antibodies

The present invention also covers truncated forms of multispecific antibodies wherein "truncated" is used herein to mean antibodies having heavy chains and/or light chains that are not full length as compared with naturally occurring heavy and light immunoglobulin chains or polypeptides. Multispecific antibodies according to the present invention are required to have a first heavy chain-light chain pairing and a second heavy chain-light chain pairing, wherein the pairings can be detected by first and second selective recognition agents that recognise distinct first and second selective recognition sites outside of the antigen binding site of each pairing. However, the heavy and light chains need not be full length as compared with naturally occurring immunoglobulin chains, provided that they contain a VH or VL domain capable of binding to a target antigen and a region or domain of adequate length to contribute residues to the distinct selective recognition sites of the antibody molecules described herein. The scope of the present invention therefore extends to any multispecific antibody having the combination of a first heavy chain-light chain pairing and second heavy chain-light chain pairing wherein the four chains are required to assemble correctly in order to produce an antibody having the correct binding profile.

In certain embodiments, the multispecific antibodies comprise or consist of a first heavy chain-light chain pairing and a second heavy chain-light chain pairing wherein the first and second heavy chains each consist of a VH domain and a CH1 domain and the first and second light chains each consist of a VL domain and a CL domain and the heavy chains associate via any non-covalent means. In a preferred embodiment, multispecific antibodies of the present invention are F(ab')₂ fragments, particularly F(ab')₂ fragments wherein the first and second heavy chains are modified by means permitting dimerization of the chains, for example by the formation of a leucine zipper.

C. Polynucleotides, DNA Constructs and Host Cells

The present invention also provides polynucleotides encoding the multispecific antibodies described herein, and expression vectors comprising such polynucleotides operably linked to regulatory sequences which permit expression of the multispecific antibodies in a host cell or cell-free expression system. Further provided are host cells or cell-free expression systems containing these expression vectors.

Polynucleotide molecules encoding the multispecific antibodies of the invention include, for example, recombinant DNA molecules. The terms "nucleic acid", "polynucleotide" or a "polynucleotide molecule" are used herein interchangeably and refer to any DNA or RNA molecule, either single- or double-stranded and, if single-stranded, the molecule of its complementary sequence. In discussing nucleic acid molecules, a sequence or structure of a particular nucleic acid molecule may be described herein according to the normal convention of providing the sequence in the 5' to 3' direction. In some embodiments of the invention, nucleic acids or polynucleotides are "isolated." This term, when applied to a nucleic acid molecule, refers to a nucleic acid molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or non-human host organism.

An isolated polynucleotide (either DNA or RNA) may further represent a molecule produced directly by biological or synthetic means and separated from other components present during its production. For recombinant production of a multispecific antibody according to the invention, one or more recombinant polynucleotide(s) encoding the multispecific antibody may be prepared (using standard molecular biology techniques) and inserted into a replicable vector for expression in a chosen host cell, or a cell-free expression system. Suitable host cells may be prokaryote, yeast, or higher eukaryote cells, specifically mammalian cells. Expression vectors suitable for use in each of these host cells are also generally known in the art.

It should be noted that the term "host cell" generally refers to a cultured cell line (prokaryote or eukaryote). Whole human beings into which an expression vector encoding a multispecific antibody according to the invention has been introduced are explicitly excluded from the definition of a "host cell".

D. Methods for Isolating Multispecific Antibodies

In a further aspect, the present invention provides methods for isolating the multispecific antibodies described herein. All embodiments described above in connection with multispecific antibodies of the present invention are applicable to the methods of the invention. The methods exploit the distinct selective recognition sites and/or distinct amino acid sequences comprised within each of the heavy chain-light chain pairings of the antibody molecule. This allows for the isolation of only those multispecific antibodies comprising both of the correct first and second heavy chain-light chain pairings.

For multispecific antibodies having first and second heavy chains that each comprise at least a fragment derived from the constant region of different human immunoglobulin subtypes or different allotypes, the methods as described herein can exploit the natural variation found within the constant region of these naturally occurring heavy chains so as to distinguish between the first and second heavy chain-light chain pairings. This also allows for the isolation of only those multispecific antibodies comprising both of the correct first and second heavy chain-light chain pairings.

Selective Recognition Agents

As discussed above, the first and second selective recognition sites comprised within the first and second heavy chain-light chain pairings are distinct in the sense that they can be selectively recognised and selectively or differentially bound by distinct first and second selective recognition agents.

The selective recognition agents according to the present invention bind exclusively or at least exhibit preferential binding to their respective selective recognition site. The selective recognition agents preferably have at least 50× higher affinity, preferably at least 100× higher affinity for their cognate selective recognition site as compared with any other site or selective recognition site located within the same antibody molecule or in an antibody molecule formed from the mispairing of the respective heavy and light chains of the antibody of interest. In order for the methods of the invention to be used to isolate multispecific antibodies having the correct first and second heavy chain-light chain pairings, the selective recognition agents must exhibit no or minimal cross-reactivity with other recognition sites within the same antibody molecule or in an antibody molecule formed from the mispairing of the heavy and light chains of the antibody of interest.

Selective recognition agents according to the present invention may take any suitable form, provided that the agent is capable of distinguishing between first and second selective recognition sites. In certain embodiments, at least one of the first and second selective recognition agents is a polypeptide having binding specificity for its cognate selective recognition site. Such polypeptides may be selected from, but not limited to: peptides; helix bundles and Affibody molecules or binding fragments thereof.

In certain embodiments, at least one of the first and second selective recognition agents is a conventional antibody or antigen binding fragment thereof, wherein the term "conventional antibody" is used herein to describe heterotetrameric antibodies containing heavy and light immunoglobulin chains arranged according to the "Y" configuration shown in FIG. 2. Such conventional antibodies may derive from any suitable species including but not limited to antibodies of mouse, rat, rabbit, goat, hamster, chicken, monkey or human origin. In certain embodiments, the first and/or second selective recognition agents are conventional antibodies derived from a species of the Camelidae family, preferably llama (*Lama glama*).

The conventional antibodies for use as selective recognition agents in the context of the present invention may include modified conventional antibody variants, such as chimeric antibodies, humanised antibodies and such like. The first and/or second selective recognition agents may be antigen binding fragments of conventional antibodies wherein the term "antigen binding fragment" includes F(ab')₂ fragments, Fab fragments, Fv fragments, sFv fragments and highly related molecules such as those based upon antibody domains which retain specific binding affinity (for example, single domain antibodies).

Conventional antibodies are particularly suitable as selective recognition agents for use in accordance with the methods of the present invention because antibodies typically exhibit binding specificity for an epitope associated with a particular target antigen. In embodiments of the present methods in which the first and/or second selective recognition agent is a conventional antibody, the target antigen is the multispecific antibody molecule of interest and the first and/or second selective recognition site is a first and/or second "epitope", which can be selectively recognised by a particular antibody.

Alternatively, or in addition, at least one of the first and second selective recognition agents may be a camelid-derived heavy chain only antibody or an antigen binding fragment thereof. Camelid heavy chain antibodies, also referred to herein as "VHH antibodies" represent a second type of antibody naturally produced in camelids. Heavy chain only antibodies are so called because they are composed of two heavy chains and are devoid of light chains (Hamers-Casterman, et al. Nature. 1993; 363; 446-8). Each heavy chain has a variable domain at the N-terminus, and these variable domains are referred to in the art as "VHH" domains in order to distinguish them from the variable domains of the heavy chains of the conventional antibodies i.e. the VH domains. Similar to conventional antibodies, the VHH domains of the molecule confer antigen binding specificity and therefore VHH antibodies or fragments such as isolated VHH domains, are suitable for use in accordance with the methods of the present invention as selective first and/or second recognition agents.

For embodiments wherein the first and second selective recognition agents are selected from either conventional heterotetrameric antibodies or VHH antibodies, antibodies specific for their respective selective recognition sites or "epitopes" may be generated or obtained by active immunization of a host species with a polypeptide comprising the first or second selective recognition site i.e. the first or second epitope. For the production of conventional antibodies, the host species may be selected from any of the following: mouse, rat, rabbit, goat, hamster, chicken, monkey, or species of the family Camelidae. For the production of VHH antibodies, any species from the family Camelidae, including *lama* species, may be immunized with a polypeptide including the respective selective recognition site or epitope.

Methods of Isolation and/or Purification

The methods as described herein can be used for isolation of a multispecific antibody from any suitable sample. In certain embodiments, the methods are used for purification of a multispecific antibody having a defined antigen binding profile from a crude preparation including the antibody of interest, for example a preparation obtained from a recombinant expression system. The methods are particularly useful for the production of an antibody preparation enriched for the multispecific antibody of interest from a starting material comprising a mixture of antibodies. In certain embodiments, the methods may be used to prepare an enriched or a homogeneous preparation of a multispecific antibody having a defined antigen binding profile from a mixture of antibodies, wherein the mixture contains antibodies having the antigen binding profile of interest and one or more different antibodies that do not have the required antigen binding profile, or have no binding activity at all. In certain embodiments, the mixture of antibodies from which the multispecific antibody is isolated contains antibodies having various different pairings of the first and second heavy and light chains found in the multispecific antibody of interest. However, within the mixture are antibodies that either do not include the full complement of first and second heavy and light chains such that they are not multispecific, or do not include the correct pairings of first and second heavy and light chains. For example, the mixture may include antibodies having the first and second pairings as required but also antibodies having (i) first heavy chain paired with first light chain only; (ii) second heavy chain paired with second light chain only; (iii) first heavy chain paired with second light chain; and/or (iv) second heavy chain paired with first light chain (see for example, the mixture shown in FIG. 1).

In certain embodiments, the methods of the present invention can be used to isolate or purify multispecific antibodies following recombinant expression in any suitable expression system or host system as described elsewhere herein. Recombinant expression of different heavy and light chain polypeptides in the same expression system, for example the same host cell or cell-free expression system, can lead to the production of antibodies having incorrect chain pairings and therefore the methods of the present invention can be used to isolate only those multispecific antibodies having the correct heavy chain-light chain pairings conferring the antigen binding profile of interest.

Figure 9:
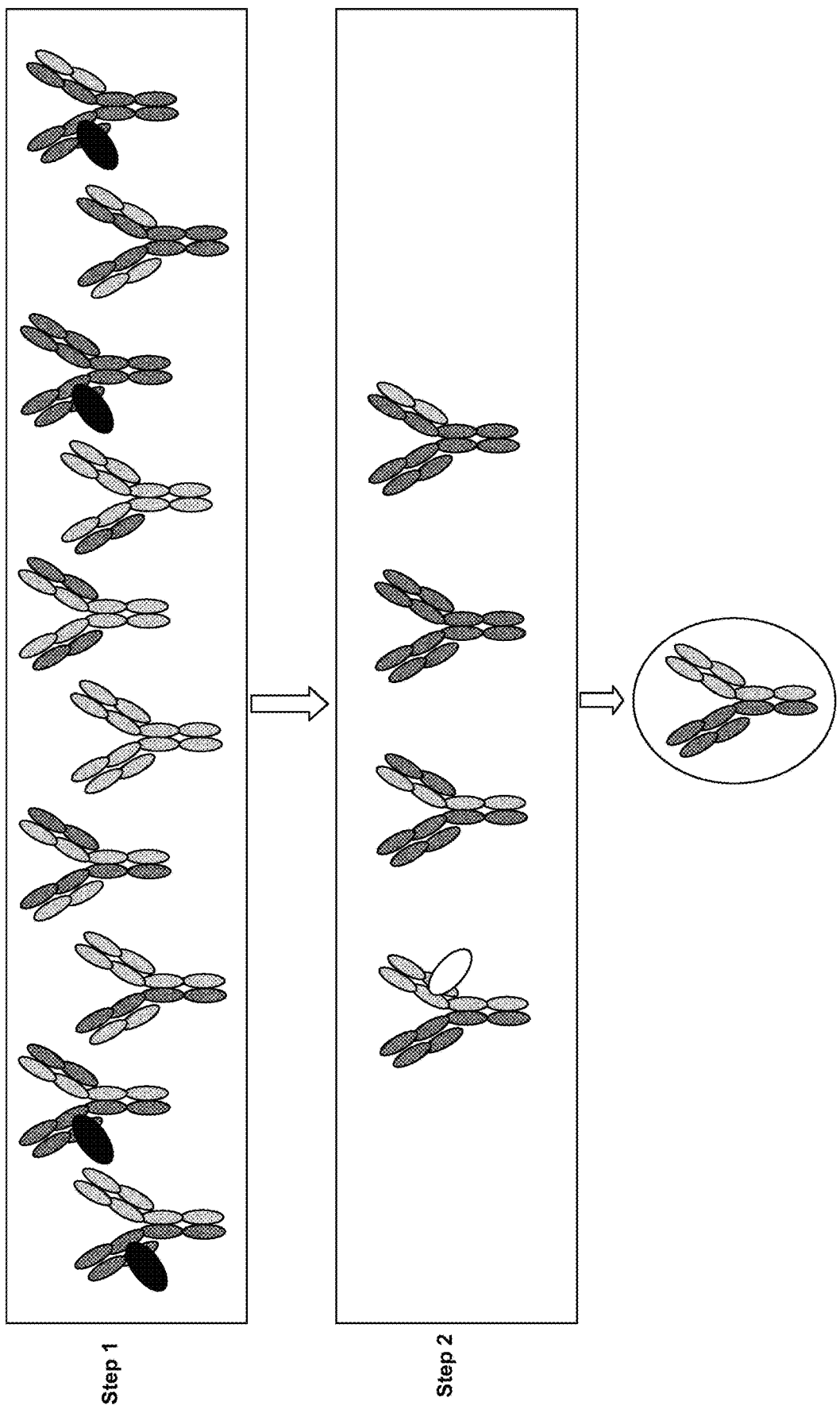
FIG. 9 Schematic of a method for isolating bispecific antibodies according to the invention. In step 1, a mixture of bispecific antibodies having various heavy chain-light chain pairings is contacted with a first selective recognition agent that selectively binds to a first selective recognition site comprised within the first heavy chain-light chain pairing of interest, but outside the antigen binding site. Antibodies bound to the first selective recognition agent are released to produce a second sample. In step 2, the second sample is contacted with a second selective recognition agent that selectively binds to a second selective recognition site comprised within the second heavy chain-light chain pairing of interest. Antibodies bound to the second selective recognition agent can be released to yield bispecific antibodies having the correct heavy chain-light chain pairings and therefore the correct antigen binding profile.

The methods of the present invention involve a two-step selection process which allows for the isolation of multispecific antibodies having both the first and second heavy chain-light chain pairings and thereby having the desired antigen binding profile. This two-step selection process is represented diagrammatically in FIG. 9.

In the first step, the sample containing the multispecific antibody of interest or suspected of containing such multispecific antibody is contacted with a first selective recognition agent under conditions that permit binding of the first selective recognition agent to the first selective recognition site, if present. Any antibodies incorporating the first heavy chain-light chain pairing will be bound by the first selective recognition agent and can therefore be separated from the sample. Antibodies bound to the first selective recognition agent can be released or dissociated using any suitable technique so as to generate a second sample containing all antibodies having at least the first heavy chain-light chain pairing.

It is possible that only some of the antibodies in the second sample contain the second heavy chain-light chain pairing and therefore the method requires a second step wherein the second sample is contacted with a second selective recognition agent with specificity for the second selective recognition site comprised within the second heavy chain-light chain pairing. Multispecific antibodies having the second pairing will be selectively bound by the second selective recognition agent and can therefore be separated from the second sample. Release of the bound antibodies will yield a preparation enriched for the multispecific antibody of interest having both first and second heavy chain-light chain pairings and thus having the antigen binding profile of interest.

In particular embodiments of the methods described herein, the multispecific antibodies to be isolated comprise or consist of a first heavy chain-light chain pairing and a second heavy chain pairing wherein the first and second heavy chain differ by at least one amino acid residue in the constant region. In particular, the first and second heavy chains may each comprise at least a fragment derived from the constant region of different human immunoglobulin subtypes or different immunoglobulin allotypes, as described elsewhere herein. For multispecific antibodies of the invention having first and second heavy chains with fragments derived from different immunoglobulin subtypes or allotypes, the selective recognition agents may differentially recognise first and second heavy chain-light chain pairings by selectively binding to first and second sites within the constant regions of the first and second heavy chain-light chain pairings, respectively, wherein one or both sites comprises at least one of the residues that differ between the immunoglobulin subtypes or allotypes, preferably at least one of the resides that differ between the CH1 domains.

The selective recognition agents may be arranged according to any suitable format to permit contact with the sample. In certain embodiments, the first and/or second selective recognition agents may be immobilized, for example, by attachment to a solid support. The first and/or second selective recognition agents may in particular, be fixed to a solid support to generate affinity chromatography columns to which the sample(s) can be applied.

In a particular embodiment of the method of the invention, the initial sample or mixture is applied to a first affinity chromatography column loaded with the first selective recognition agent capable of binding the first selective recognition site in the multispecific antibody of interest. Once all of the sample has passed through the column, bound antibodies may be eluted using any suitable technique and/or elution buffer. The eluate from this first column is then applied to a second affinity chromatography column loaded with the second selective recognition agent capable of binding to the second selective recognition site in the multispecific antibody of interest. Once all of the eluate from the first column has been left to pass through the second column, the antibody bound to the second column may be eluted using any suitable technique or elution buffer. The eluate from the second column will contain a preparation of antibodies enriched for multispecific antibodies having the desired binding specificity for at least first and second antigens via correct first and second heavy chain-light chain pairings.

The methods of the present invention may be employed in combination with other antibody purification or isolation methods in order to achieve increased yields or higher purity yields of homogenous antibody preparations. For example, the methods described herein may be preceded by passing the sample through a protein A affinity column so as to select for only properly assembled antibodies containing at least two heavy and two light chains.

The multispecific antibodies and methods of the present invention represent an improvement over the prior art multispecific antibodies and methods for a number of reasons. Firstly, in contrast to approaches based on the use of anti-idiotypic binding agents, the antibodies and methods of the present invention allow for the isolation of multispecific antibodies having the correct heavy chain-light chain pairings using a universally applicable technique. In particular, the fact that the multispecific antibodies comprise at least first and second heavy chain-light chain pairings which can be distinguished on the basis of distinct amino acid sequences in the form of distinct selective recognition sites located outside of the antigen binding site allows for the isolation of any multispecific antibodies comprising at least first and second selective recognition sites, irrespective of the antigen binding profile of the multispecific antibody. In particular, multispecific antibodies having binding specificity for any combination of epitopes and target antigens can be engineered so as to contain common first and second selective recognition sites within the heavy chain-light chain pairings outside of the antigen binding sites. It follows that common selective recognition agents designed to specifically recognise and bind particular first and second selective recognition sites may be developed and used to isolate and/or purify multispecific antibodies having any number of different antigen binding profiles, provided that the heavy chain-light chain pairings of the molecule include the first and second selective recognition sites bound by the selective recognition agents. The broad applicability of selective recognition agents that bind particular selective recognition sites represents an improvement on methods that rely on anti-idiotypic agents that recognise differences at the level of the antigen binding site.

The methods of the present invention also represent an improvement over prior art methods that focus solely on addressing the problem of mispairing between heavy chains of bispecific antibodies. The methods described herein allow multispecific antibodies having the correct heavy chain-light chain pairings to be isolated, for example from a mixture containing antibodies having various combinations of pairings of heavy and light chains. The isolation of multispecific antibodies having only the correct pairings is achieved by virtue of the fact that each selective recognition site includes residues derived from the heavy chain and the light chain of the pairing. In the absence of the correct heavy chain-light chain pairings, the first and/or second selective recognition sites are not present such that these molecules are not recognised and bound by the selective recognition agents. Only multispecific antibodies having the correct heavy chain-light chain pairings and thus presenting both selective recognition sites are selectively bound and captured by both first and second selective recognition agents in the first and second stages of the isolation method described herein.

A further advantage conferred by the methods of the present invention is that the methods can exploit the natural variation found in the constant regions of heavy chains and light chains of different classes, subtypes and allotypes. As described above, the first and second heavy chains may be different allotypes and therefore be distinguished by virtue of the natural amino acid differences found in the constant regions, and in particular the CH1 domains, of the naturally occurring heavy chain polypeptides. Alternatively, or in addition, the first and second light chains may belong to different classes e.g. the lambda and kappa light chain classes. The differences in amino acid sequence between these two classes of light chain may be exploited in the production of selective recognition agents that selectively recognise either the first pairing or second pairing of the antibody molecule.

In view of the natural variation to be found in the constant regions of different heavy and light polypeptide chains, the need for extensive protein engineering of multispecific antibodies is minimised using the methods of the present invention. Furthermore, the fact that the multispecific antibodies can include naturally occurring heavy and light polypeptide chains or fragments thereof means that any unfavourable properties associated with mutated immunoglobulin sequences e.g. unwanted immunogenicity can be avoided, and favourable properties, such as the retention of natural effector function, can be preserved.

E. Reagents and Kits

The present invention also relates to reagents for producing multispecific antibodies according to the present invention, and reagents, particularly antibodies, for isolating or purifying multispecific antibodies according to the present invention. Combinations of these reagents may be packaged in kit form.

Polynucleotides Encoding Fragments of Multispecific Antibodies

As described in section C above, the present invention includes expression vectors comprising polynucleotide sequences encoding the multispecific antibodies provided herein. Such expression vectors may be incorporated into host cells or cell-free expression systems leading to recombinant expression of multispecific antibodies of the invention.

The present invention further includes polynucleotides or isolated polynucleotides encoding each of the separate immunoglobulin chains of the multispecific antibodies described herein. In addition, the invention includes polynucleotides or isolated polynucleotides encoding fragments of each of the separate immunoglobulin chains, for example fragments of the first and/or second heavy and light chains, wherein a fragment is shorter than the full length immunoglobulin polypeptide chain by 1, 2, 3, 4, 5, 6, 7, 8, 9, 10, 20, 30, 40, 50, 60, 70, 80, 90, 100, 200 amino acid residues.

In certain embodiments, polynucleotides of the present invention encode fragments of the respective first and/or second heavy and/or light chains wherein the fragment consists only of the constant region of each chain. Polynucleotides may also encode fragments of the respective first and/or second heavy and/or light chains wherein the fragment excludes the polynucleotide regions encoding the CDR sequences. Polynucleotides of the invention must encode fragments that are large enough to include the specific residues from both the first and second heavy and light chains that contribute to the first and second selective recognition sites. Alternatively, polynucleotides of the invention must encode fragments of naturally occurring heavy and light chains that are long enough to encode a length of amino acid residues that differ by at least one residue when produced as part of the first heavy chain and/or second heavy chain.

Polynucleotides encoding fragments as described above may be useful as reagents for producing multispecific antibodies of the present invention. The polynucleotides may be inserted into plasmids or cloning vectors which allow for the introduction of polynucleotide sequences encoding the portion or portions of the multispecific antibody which is/are absent from the fragment. Suitable plasmids or vectors would be known to those skilled in the art.

For example, polynucleotides encoding fragments consisting only of the constant region of the heavy chain or light chain may be incorporated into a plasmid or cloning vector such that separate polynucleotides encoding the VH and/or VL domains of antibodies of interest can be inserted in-frame into the open reading frame of the polynucleotide encoding the immunoglobulin chain constant regions. It would also be within the capabilities of the skilled person to take a polynucleotide encoding a fragment of a multispecific antibody lacking the CDR sequences and introduce polynucleotides encoding CDR sequences from two or more antibodies of interest. The polynucleotides encoding fragments serve as the starting material for the production of multispecific antibodies having particular first and second selective recognition sites associated with heavy chain-light chain pairings comprising antigen binding sites targeting any antigens of interest.

Antibodies that Bind Multispecific Antibodies

As described in section D, the selective recognition agents used in the context of the methods of the present invention may be antibodies or antigen binding fragments thereof. All embodiments of the invention described above in the context of the methods of the invention are equally applicable to antibodies or antigen binding fragments provided herein as reagents for isolating or purifying multispecific antibodies according to the invention.

The present invention further provides an antibody or antigen binding fragment thereof that binds to a multispecific antibody as described elsewhere herein, wherein the antibody or antigen binding fragment thereof binds to an epitope, wherein the epitope is:

(i) comprised within the first pairing (the first heavy chain paired with the first light chain) but not the second pairing (the second heavy chain paired with the second light chain); or (ii) comprised within the second pairing (the second heavy chain paired with the second light chain) but not the first pairing (the first heavy chain paired with the first light chain) and wherein the epitope does not include residues from the antigen binding site.

The epitope to which the antibody or antigen binding fragment thereof binds is distinct or unique in that it is comprised only within either the first heavy chain-light chain pairing or the second heavy chain-light chain pairing of the multispecific antibody. Thus, in certain embodiments wherein the multispecific antibody comprises first and second selective recognition sites comprised within the first and second heavy chain-light chain pairings, respectively, the epitope to which the antibody binds comprises or consists of either the first selective recognition site or the second selective recognition site. As mentioned above, wherein the selective recognition agents of the invention are antibodies, the term "selective recognition site" may be used interchangeably with the term "epitope".

For multispecific antibodies of the invention comprising first and second heavy chains wherein the heavy chains differ by at least one amino acid residue in the constant region, preferably the CH1 domain, the epitope to which the antibody binds may comprise at least one of said residues that differs between the constant regions of the heavy chains. In certain embodiments, the epitope to which the antibody binds may comprise or consist of 2, 3, 4, 5, 6 or 7 amino acids that differ between the constant regions, preferably the CH1 domains, of the first and second heavy chains.

Multispecific antibodies comprising first and/or second heavy chains with fragments and/or amino acid substitutions derived from various naturally occurring heavy chain subtypes and allotypes are described elsewhere herein. In certain embodiments, antibodies are provided that bind to an epitope comprised either within the first heavy chain-light chain pairing or the second heavy chain-light chain pairing of the multispecific antibody, wherein the epitope comprises one or more residues in the first or second heavy chain that differs between the subtype and/or allotypes of the first and second heavy chains.

In certain embodiments, provided herein are antibodies or antigen binding fragments that bind to a multispecific antibody of the invention, wherein the epitope:

(i) is comprised within the first pairing and comprises one or more amino acid residues selected from the following residues in the first heavy chain: C131, R133, E137, S138, S178, N192 and/or F193; or (ii) is comprised within the second pairing and comprises one or more amino acid residues selected from the following residues in the second heavy chain: S131, K133, G137, G138, Y178, S192 and/or L193.

In certain embodiments, the epitope comprises a distinct combination of amino acid residues in the heavy chain. For example, the epitope may be comprised within the first pairing and comprise the first heavy chain amino acid residues E137 and S138; or
(ii) comprised within the second pairing and comprise the second heavy chain amino acid residues G137 and G138; or
(iii) comprised within the first pairing and comprise the first heavy chain amino acid residues N192 and F193; or
(iv) comprised within the second pairing and comprises the second heavy chain amino acid residues S192 and L193; or
(v) comprised within the first pairing and comprise the first heavy chain amino acid residues R133, E137, S138, S178, N192 and F193; or
(vi) comprised within the second pairing and comprise the second heavy chain amino acid residues K133, G137, G138, S192, L193, Y178.

The antibodies and antigen binding fragments thereof for use in the isolation or purification of multispecific antibodies according to the present invention may take any of the forms described above in the context of "selective recognition agents" for use in the methods of the present invention. For example, the antibodies may be camelid-derived VHH antibodies. Alternatively, the antibodies may be conventional antibodies, preferably conventional antibodies comprising at least one complementarity determining region in the VH domain or VL domain derived from an antibody of a species in the family Camelidae. In particularly preferred embodiments, the entire VH and/or VL domain of the conventional antibody is derived from a camelid species, preferably a llama (*Lama glama*).

The present invention also provides polynucleotides encoding the antibodies and antigen binding fragments described herein, and expression vectors comprising such polynucleotides operably linked to regulatory sequences which permit expression of the antibodies in a host cell or cell-free expression system. Further provided are host cells or cell-free expression systems containing these expression vectors.

Kits

Also provided herein are kits with reagents for isolating multispecific antibodies according to the methods of the present invention. In particular, the present invention provides kits comprising first and second selective recognition agents, preferably wherein the first and second selective recognition agents are antibodies as described elsewhere herein. First and second selective recognition agents recognising particular combinations of first and second selective recognition sites may be packaged together to be used for the isolation and/or purification of multispecific antibodies having specific combinations of first and second selective recognition sites.

The kits comprising first and second selective recognition agents may further include polynucleotide sequences (or plasmids or vectors comprising the same) as described above wherein the polynucleotides encode fragments of multispecific antibodies of the present invention, particularly fragments encoding at least the regions of the multispecific antibody incorporating first and second selective recognition sites. In this way, the kit can be used by one of skill in the art to produce multispecific antibodies having distinct first and second selective recognition sites recognised by the first and second selective recognition agents provided within the same kit. It follows that kits of the invention may be used to produce multispecific antibodies as described herein, and also to isolate such multispecific antibodies according to the methods of the invention.

The kits may optionally include labelling and or instructional materials providing directions for practising the methods of the invention.

The invention will be further understood with reference to the following non-limiting examples.

EXAMPLES

Example 1: Identification of Relevant Residues in CH1 Domains

The aim of this experiment was to identify heavy chain-only antibodies (VHHs) with the ability to specifically recognise and differentiate between distinct CH1-CL domain pairings. In particular, the aim was to identify VHH antibodies having binding specificity for either a CH1-CL complex formed between a first heavy chain CH1 domain and the CL domain of a lambda light chain (referred to herein as CLambda) or a second CH1-CL complex formed between a second heavy chain CH1 domain and a kappa light chain (referred to herein as Ckappa). In order to achieve the desired binding specificity, the aim was to identify an epitope formed by each pairing having residues contributed from both the CH1 and CLambda/Ckappa domains, and with at least one amino acid difference between the residues contributed from the first and second heavy chain CH1 domains.

The amino acid sequences of all publicly accessible CH1 domains from IgG1, IgG2, IgG3 and IgG4 were aligned and variations in the amino acid sequences were identified. The amino acid variations or differences between the different subtypes and allotypes were identified by doing a simple protein alignment (see FIG. 3). The location of these amino acid variations in the three-dimensional structure of an antibody was determined by mapping these positions onto solved Fab structures (Lambda and Kappa Fabs).

Amino acid variation located at the surface of the CH1 domains and located in range of the Clambda and Ckappa chains was identified. Particular residues of interest (and combinations of residues) identified as suitable for contributing to epitopes distinguishing CH1/Clamdba and CH1/Ckappa pairings are listed below:

At position 131: residue C in the first heavy chain domain, and residue S in the second heavy chain domain;
At position 133: residue R in the first heavy chain domain, and residue K in the second heavy chain domain;
At position 137: residue E in the first heavy chain domain, and residue G in the second heavy chain domain;
At position 138: residue S in the first heavy chain domain, and residue G in the second heavy chain domain;
At positions 137 and 138: residues E and S in the first heavy chain domain, and residues G and G in the second heavy chain domain;
At position 178: residue S in the first heavy chain domain, and residue Y in the second heavy chain domain;
At position 192: residue N in the first heavy chain domain and residue S in the second heavy chain domain;
At position 193: residue F in the first heavy chain domain and residue L in the second heavy chain domain;
At positions 192 and 193: residues N and F in the first heavy chain domain, and residues S and L in the second heavy chain domain.

Example 2: Generation of IgG with Specific Variation in the CH1 Paired with Clambda or Ckappa Functional human IgG1 antibodies (binding to a target protein) having either a Lambda light chain (Antibody A, C, D and E) or a Kappa light chain (antibody B and F) were mutated in their CH1 domain by mutagenesis to create the antibodies as indicated in Table 11:

TABLE 11

|  | Mab A (Lambda) | Mab B (Kappa) | MabC (Lambda) | Mab D (Lambda) | Mab E (Lambda) | Mab F (Kappa) |
|---|---|---|---|---|---|---|
| R133K | mutA1/Amut1 | mutB1/Bmut1 | mutC1/Cmut1 | mutD1/Dmut1 | mutE1/Emut1 | mutF1/Fmut1 |
| E137G, S138G | mutA2/Amut2 | mutB2/Bmut2 | mutC2/Cmut2 | mutD2/Dmut2 | mutE2/Emut2 | mutF2/Fmut2 |
| N192S, F193L | mutA3/Amut3 | mutB3/Bmut3 | mutC3/Cmut3 | mutD3/Dmut3 | mutE3/Emut3 | mutF3/Fmut3 |
| R133K, E137G, S138G, N192S, F193L, S178Y | mutA4/Amut4 | mutB4/Bmut4 | mutC4/Cmut4 | mutD4/Dmut4 | mutE4/Emut4 | mutF4/Fmut4 |
| S178Y | mutA5/Amut5 | mutB5/Bmut5 | mutC5/Cmut5 | mutD5/Dmut5 | mutE5/Emut5 | mutF5/Fmut5 |

The antibodies were produced separately by transient transfection of mammalian expression vectors encoding the heavy chains and mammalian expression vectors encoding the light chains into HEK cells. Six days after the transfection, the supernatant of the cells was collected, and the antibody present was purified from the medium using standard Protein A purification methods.

All the antibodies were produced without significant loss in yield as compared to the non-mutagenised antibodies, suggesting no effect of the mutations on the stability or capacity to bind protein A.

Example 3: Identification of VHH Antibodies that Recognise the IgG Variation in the CH1 Paired with Clambda or Ckappa To identify VHH antibodies capable of recognising specific variation in a heavy chain CH1 domain paired with either a lambda or kappa CL domain, llama were immunized with the antibodies mutE1/Emut1, mutE2/Emut2, mutE3/Emut3 and mutE4/Emut4 (separately or in a mixture) or were immunized with mutF1/Fmut1, mutF2/Fmut2, mutF3/Fmut3 and mutF4/Fmut4 (separately or in a mixture). To further increase the immune response towards the human CH1 domains containing the mutations, the human CH1, Clambda and Ckappa domains were fused to llama variable domains (VH, Vlambda and Vkappa) as well as llama Fc. Immunization was done by 6 consecutive injections of antibodies mixed with non-complete Freund adjuvant, starting with two injections of 100 µg followed by four injections of 50 µg of antibody mixture.

After immunization, 400 ml of llama PBLs were isolated using standard ficoll separation and the RNA was extracted using an RNA Qiagen kit. cDNA was synthesised using random hexamer primers and the superscript III transcriptase kit from LifeTechnologies. Genes encoding the VHH antibodies were cloned by PCR (using a technique similar to that described in the literature, in particular Roovers et al. Cancer Immunol Immunother. 2007 March; 56(3):303-317) and cloned into phagemid vectors to allow phage display selection.

After library construction, the phage expressing VHH antibodies able to recognise the mutation(s) in the CH1 domains in a lambda antibody were selected by phage display using antibodies selected from: mutC1/Cmut1, mutC2/Cmut2, mutC3/Cmut3 or mutC4/Cmut4 (coated or biotinylated). All the selections were done in the presence of wild-type antibody (with no mutations in CH1) to avoid the identification of VHH antibodies lacking specificity for the mutation(s) in CH1. In addition, in some cases selection was also carried out in the presence of an antibody containing the same CH1 domain mutation but paired with a kappa light chain (called counter selection; for example using mutF4/Fmut4 when selection was being carried out for VHH antibodies specific for mutC4/Cmut4). The purpose of this additional selection was to isolate VHH antibodies having an epitope specific to the mutated CH1-Clambda pairing.

The phage expressing VHH antibodies able to recognise the CH1 mutation(s) in a Kappa antibody were selected by phage display using antibodies selected from: mutF1/Fmut1, mutF2/Fmut2, mutF3/Fmut3 or mutF4/Fmut4 (coated or biotinylated). All the selections were done in the presence of wild-type antibody (with no mutations in CH1) to avoid the identification of VHH antibodies lacking specificity for the mutation(s) in CH1. In addition, in some cases selection was also carried out in the presence of an antibody containing the same CH1 domain mutation but paired with a lambda light chain (called counter-selection; for example using mutC4/Cmut4 when selection was being carried out for VHH antibodies specific for mutF4/Fmut4). The purpose of this additional selection was to isolate VHH antibodies having an epitope specific to the mutated CH1-Ckappa pairing.

An example of the phage display selection rounds are indicated in Table 12 below.

TABLE 12

| LIBRARIES | ROUND 1 | | ROUND 2 | |
|---|---|---|---|---|
|  | PANNING SELECTION | COUNTER-SELECTION | IN-SOLUTION SELECTION | COUNTER-SELECTION |
| 2x E-llamas | Cmut1 | Cwt (+Fmut1) | bio-Cmut1 | Cwt (+Fmut1) |
|  | Cmut2 | Cwt (+Fmut2) | bio-Cmut2 | Cwt (+Fmut2) |
|  | Cmut3 | Cwt(+Fmut3) | bio-Cmut3 | Cwt(+Fmut3) |
|  | Cmut4 | Cwt(+Fmut4) | bio-Cmut4 | Cwt(+Fmut4) |
| 2x F-llamas | Fmut1 | Fwt (+Cmut1) | bio-Fmut1 | Fwt (+Cmut1) |
|  | Fmut2 | Fwt (+Cmut2) | bio-Fmut2 | Fwt (+Cmut2) |
|  | Fmut3 | Fwt (+Cmut3) | bio-Fmut3 | Fwt (+Cmut3) |
|  | Fmut4 | Fwt (+Cmut4) | bio-Fmut4 | Fwt (+Cmut4) |

Figure 10:
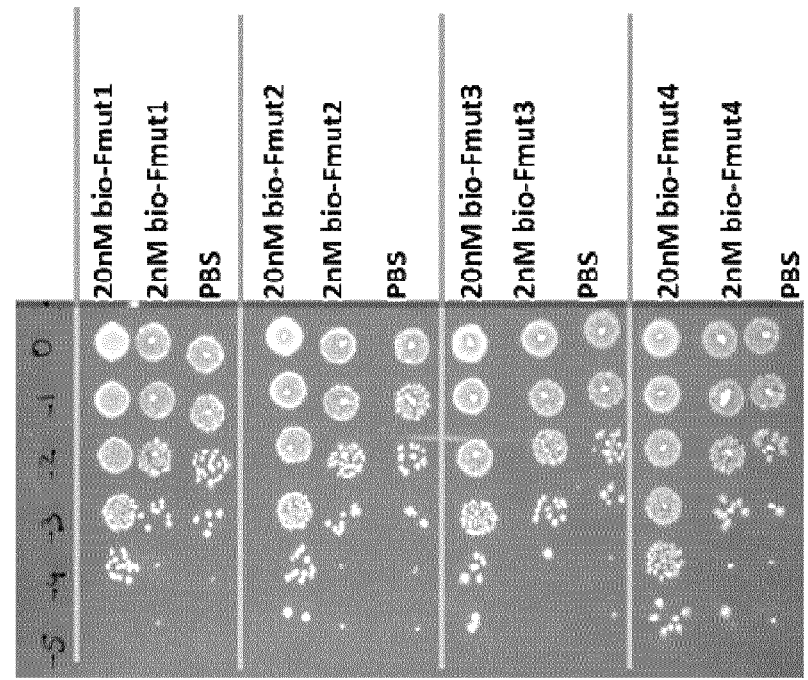
FIG. 10 Phage display selection for VHH antibodies with binding specificity for antibodies having mutations in the CH1 domain. Results of phage titration on *E. coli* TG1 cells following selection of VHH-expressing phage using the method described in Example 3 and summarised in Table 12.
Figure 10:
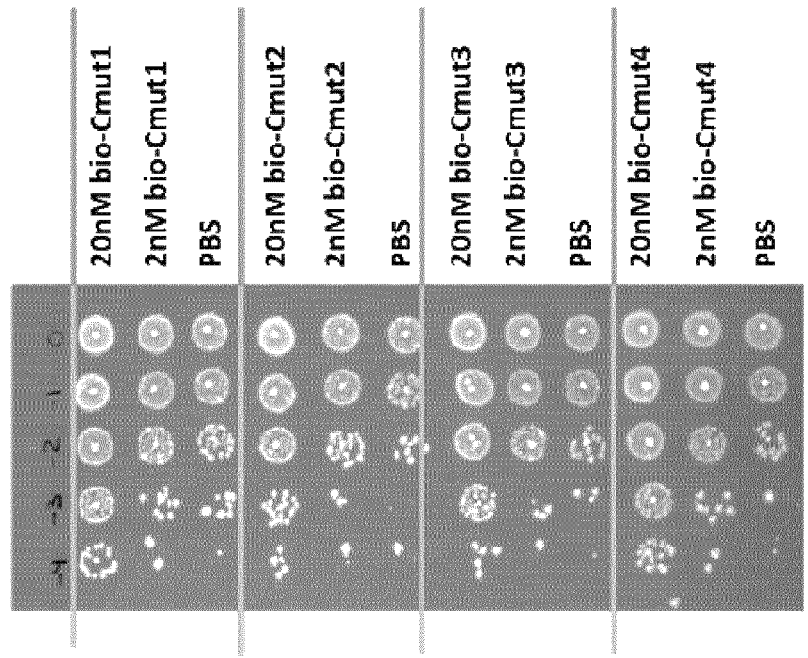

Phage display selections were carried out using the antibodies shown in the table above coated at 1 or 10 µg/ml on Maxisorp plates. The counter-selections were carried out with the antibodies indicated by adding an excess of the antibody in solution with the phage. After selection, the bound phage was removed by trypsin elution, and the number of phage were estimated by serially diluting the eluate in PBS and infecting TG1 bacteria. After bacterial infection, aliquots of TG1 were spotted on agar plates containing ampicillin and glucose. The number of colonies at each spot correlates with the number of phage present in the diluted aliquot. The results of the selection are shown in FIG. 10. The phage dilutions are indicated above the images: 0, $-1=10^{-1}$, $-2=10^{-2}$, $-3=10^{-3}$, $-4=10^{4}$, $-5=10^{-5}$.

Example 4: Screening of VHH Specific for the IgG Variation in the CH1 Paired with Clambda or Ckappa After selection (for example mutC4/Cmut4), the VHH antibodies of single clones were produced and VHHs were tested (using ELISA) for binding to:

- mutant antibodies having the correct light chain (for example mutC4/Cmut4);
- the same antibody without the mutation in the CH1 domain (for example, a wild-type antibody);
- the same antibody with a different mutation in the CH1 domain (for example mutC1/Cmut1, mutC2/Cmut2 etc.); and
- an antibody with a different light chain (for example mutF4/Fmut4, mutF3/Fmut3 etc. . . . ).

For example VHH selected for mutC4/Cmut4 (lambda) were tested in ELISA for binding to mutC4/Cmut4, wtC and mutF4/Fmut4. For example VHH selected for Fmut4 (kappa) were tested in ELISA for binding to Fmut4, wtF and Cmut4.

The ELISA results (OD) of some representative clones are indicated below in Table 13.

TABLE 13

| | Coating for ELISA | | | |
|---|---|---|---|---|
| VHH clone | Cmut4 | Fmut4 | Fwt | Specificity |
| 8G12 | 0.2 | 0.159 | 0.063 | variant 4 => not OK |
| 8G1 | 0.068 | 0.128 | 0.079 | Variant 4 in presence of Kappa light chain => OK |
| 8G11 | 0.054 | 0.123 | 0.073 | Variant 4 in presence of Kappa light chain => OK |
| 8B03 | 0.068 | 0.221 | 0.069 | Variant 4 in presence of Kappa light chain => OK |
| 8GO9 | 0.068 | 0.153 | 0.114 | F specific => not OK |

The sequences of the VHH clones in Table 13 are shown in Table 14.

TABLE 14

| VHH Clone | Sequence | SEQ ID NO |
|---|---|---|
| 8G12 | EVQLVESGGGLVRAGGSLRLSCAASGSIFGTTNMGW YRQAPGTQRDLVATINNGGITNYADSVKGRFTISTD YTKNTVYLQMDRLKPEDTAVYYCNAEYHFRPPSWGQ GTQVTVSS | 15 |

TABLE 14-continued

| VHH Clone | Sequence | SEQ ID NO |
|---|---|---|
| 8G1 | QVQLVESGGGLVQPGGSLRLSCRASGAIFSINHMGW YRQAPGKQRELVATITSGGSTNYADSVKGRFTISRD NAKNTVYLQMNSLKPEDTAVYSCNLDWTTGWGSRRD YWGQGTQVTVSS | 16 |
| 8G11 | EVQLVESGGGLVQAGGSLRLSCAASGRTFDIYTMGW FRQVPGKEREFVADIGRAGGTTHYADSVKGRFAISR DNANDAVHLQMNSLKPEDTAVYYCATKVVPRAGRRL LDYDYWGQGTQVTVSS | 17 |
| 8B03 | EVQLVESGGGLVQPGGSLRLSCRASGAIFSINHMGW YRQAPGKQRELVATITSGGSTNYADSVKGRFTISRD NAKNTVYLQMNSLKPEDTAVYSCNLDWTTGWGSRRD YWGQGTQVTVSS | 18 |
| 8GO9 | QVQLVESGGGLVQAGGSLRLSCAASGRTFSRYGMSW FRQAPGKEREFVATISRGGSSTNYADSTKGRFTVSR DNAKNTVVLQMNSLKPEDTAVYYCAADTNWPVGAYE YWGQGTQVTVSS | 19 |

In this example:

Clone 8G12 appears specific for the mut4 mutations (any of R133K, E137G, S138G, N192S, F193L, S178Y);

Clones 8G1, 8G11 and 8603 are binding to Fmut4 (having a kappa light chain) and not Cmut4 (having a lambda light chain) nor to Fwt (with a kappa light chain) suggesting binding to the mut4 mutation in the context of a kappa light chain and thereby indicating that their epitope is shared between the mutation and the Kappa light chain;

Clone 8G09 binds to Fmut4 and also Fwt, suggesting that it binds to the F antibody independently of the mutation.

To confirm that the VHH antibodies (i.e. the purification tools) are capable of distinguishing between the CH1/Clambda pairing (or CH1/Ckappa pairing) irrespective of the binding specificity of the antibody, the binding of the VHH antibodies can be tested against several antibodies having different variable domains, and therefore different functionalities, but the same mutation in the CH1 domains.

Example 5: Identification of VHH Antibodies that Recognise the IgG Variation in the CH1 Paired with Clambda or Ckappa To identify more VHH antibodies with the desired specificity for CH1 paired with Clambda or Ckappa, further llama immunizations were done with only mut4 (Cmut4 or Fmut4). Immunization, RNA extraction and library construction were carried out as described above.

Selection for clones from the phage libraries with specificity for the particular CH1/CL pairs was carried out as indicated below in Table 15, with novel antibody preparations used for the selection. Notably Cmut4/Mix (which is the heavy chain of Cmut4 with a Kappa light chain of the F antibody) and Fmut4/mix (which is the heavy chain of Fmut4 with a lambda light chain of the C antibody) were used also for counter-selection in parallel to Cwt and Fwt counter-selection, which allowed identification of mutation-specific VHH antibodies. These were screened later to test if their epitope overlaps with the lambda or kappa light chain.

TABLE 15

| Immunization | Type sel | R1 Coating R1 | R1 Counter-selection | R2 coating R2 | R2 Counter-selection | R3 coating R3 | R3 Counter-selection |
|---|---|---|---|---|---|---|---|
| Cmut4 | A1 | Cmut4 | Cwt | Cmut4 | Cwt | Fmut4/MIX | Cwt |
| (2 llamas) | B1 | Cmut4 | Cmut4/Mix | Cmut4 | Cmut4/Mix | Fmut4/MIX | Cwt |
| Fmut4 | A2 | Fmut4 | Fwt | Fmut4 | Fwt | Cmut4/MIX | Fwt |
| (2 llamas) | B2 | Fmut4 | Fmut4/Mix | Fmut4 | Fmut4/Mix | Cmut4/MIX | Fwt |

Figure 11:
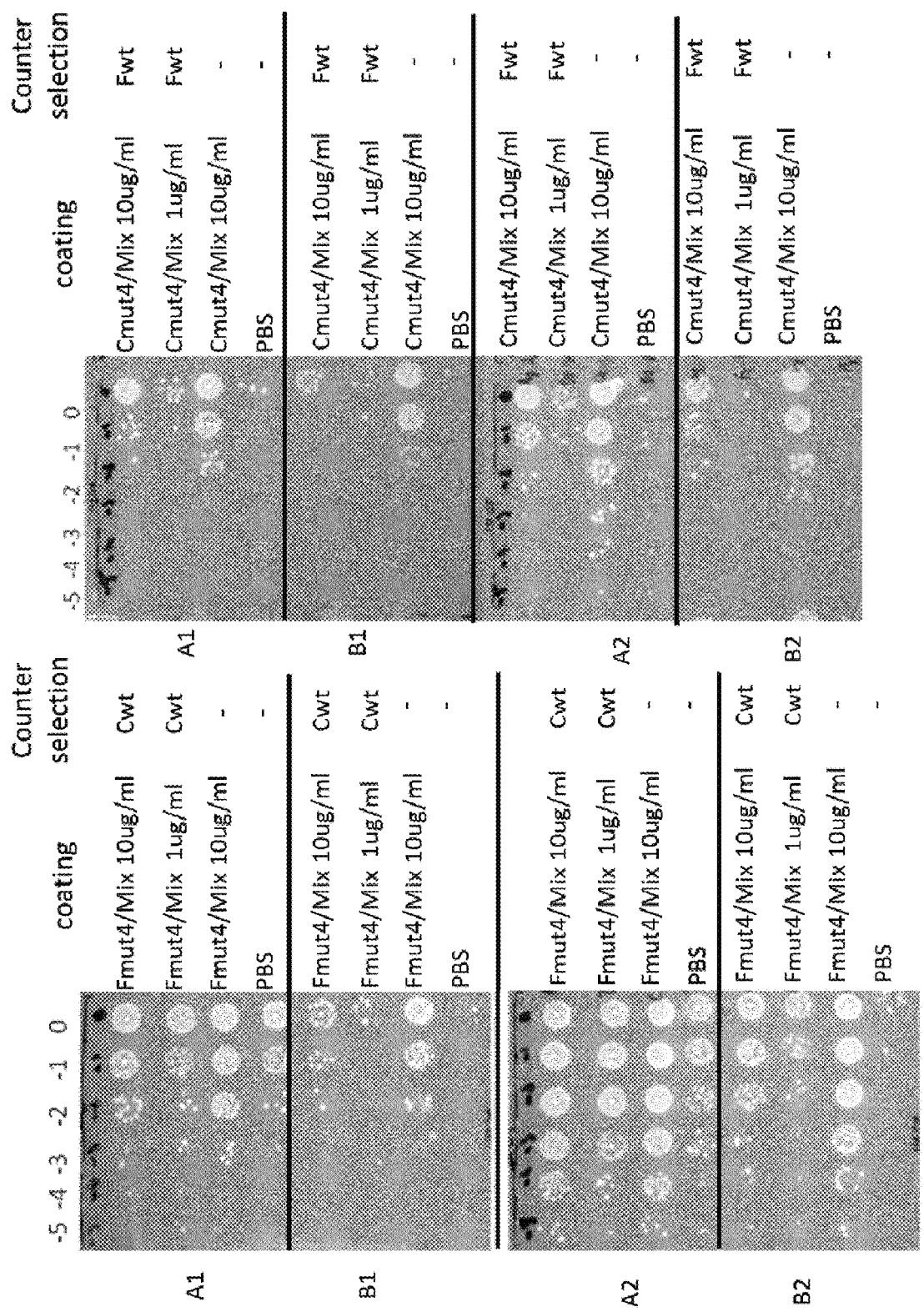
FIG. 11 Phage display selection for VHH antibodies with binding specificity for antibodies having mutations in the CH1 domain. Results of phage titration on *E. coli* TG1 cells following selection of VHH-expressing phage using the method described in Example 5 and summarised in Table 15.

The results of the selection were assessed as described above in Example 3 using phage titration and infection of TG1 bacterial cells, as shown in FIG. 11. The phage titrations clearly show that specific VHHs are selected over non-coated wells (PBS) and that the presence of a counter selection agent (to remove unwanted VHH) has the desired effect.

Example 6: Screening of VHH Specific for the IgG Variation in the CH1 Paired with Clambda or Ckappa After selection, the VHH antibodies of single clones were produced and VHHs were screened by ELISA. The desired binding characteristics are indicated in Table 16

TABLE 16

| Immunization/Selection | | Screening | | | |
|---|---|---|---|---|---|
| Cmut4 | Coating: | Cmut4 (lambda) | Cwt (lambda) | Fmut4 (Kappa) | Fmut4/mix (lambda) |
| | Desired binding: | + | − | − | + |
| Fmut4 | Coating: | Fmut4 (Kappa) | Fwt (Kappa) | Cmut4 (lambda) | Cmut4/mix (Kappa) |
| | Desired binding: | + | − | − | + |

Clones having the required binding characteristics in ELISA were identified from type selection A2 (6MP7 clones) and B2 (6MP8 clones) (see Table 17 below). Clones were scored positive when OD signal was at 1.5 higher than the blank (no VHH added=BLANK).

TABLE 17

| | ELISA OD value on the indicated coated antibodies | | | |
|---|---|---|---|---|
| VHH clones | Fmut4 (Kappa) | Fwt (Kappa) | Cmut4/mix (Kappa) | Cmut4 (Lambda) |
| 6MP8A8 | 0.150 | 0.052 | 1.032 | 0.048 |
| 6MP8C10 | 0.122 | 0.048 | 0.813 | 0.046 |
| 6MP8C12 | 0.147 | 0.051 | 0.927 | 0.049 |
| 6MP8C7 | 0.098 | 0.045 | 0.162 | 0.061 |
| 6MP8C8 | 0.434 | 0.046 | 0.166 | 0.047 |
| 6MP8C9 | 0.732 | 0.045 | 0.172 | 0.047 |
| 6MP8D7 | 3.864 | 0.047 | 0.217 | 0.048 |
| 6MP8D9 | 3.327 | 0.049 | 0.179 | 0.047 |
| 6MP8E9 | 0.387 | 0.047 | 0.205 | 0.047 |
| BLANK 6MP8 | 0.051 | 0.046 | 0.054 | 0.048 |
| 6MP7E6 | 0.475 | 0.042 | 0.099 | 0.079 |
| 6MP7B2 | 0.447 | 0.044 | 0.081 | 0.067 |
| 6MP7E10 | 0.114 | 0.044 | 0.079 | 0.065 |
| 6MP7E11 | 0.689 | 0.051 | 0.077 | 0.05 |
| BLANK 6MP7 | 0.051 | 0.066 | 0.046 | 0.061 |

Example 7: Purification of Antibodies Using the Purification Tools

VHH antibodies recognizing a specific epitope formed by the (variant-)CH1-CLambda pairing or formed by the (variant-)CH1-Ckappa pairing were selected for the preparation of affinity purification columns using conventional methods. For example, the VHH antibodies can be coupled to sepharose beads and VHH-functionalized sepharose is packed into small Tricorn columns, or a large 16K column with adaptors for small volumes. Analysis of the specificity of the columns is studied using chromatography and purified mAbs.

VHH-columns are equilibrated in PBS and the antibodies are injected on the column in PBS. After washing off the unbound monoclonal antibodies (properly paired second arm of the bispecific and mispaired first arm antibodies), bound monoclonal antibodies (containing the properly paired first arm) are eluted with 50 mM glycine pH=2.0. The identity of the antibodies present in the elution can be confirmed functionally (in ELISA or Biacore) or analytically by, for example, high resolution mass spectrometry and SDS-Page.

The compatibility of the tools to purify bispecific antibodies (in the case where one arm is a lambda and one arm is a kappa) is shown in Table 18 below (L: Lambda; K: Kappa).

TABLE 18

| | Mut1 (K) | Mut2 (K) | Mut3 (K) | Mut4 (K) | wt (K) |
|---|---|---|---|---|---|
| Mut1(L) | — | Y | Y | Y | Y |
| Mut2(L) | Y | — | Y | Y | Y |
| Mut3(L) | Y | Y | — | Y | Y |
| mut4(L) | Y | Y | Y | — | Y |
| wt (L) | Y | Y | Y | Y | — |

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. Moreover, all embodiments described herein are considered to be broadly applicable and combinable with any and all other consistent embodiments, as appropriate.

Various publications are cited herein, the disclosures of which are incorporated by reference in their entireties.

The invention claimed is:

1. A composition comprising:
   (i) a first polynucleotide and a second polynucleotide encoding a first pairing of a bispecific antibody, wherein the first polynucleotide encodes a heavy chain comprising a first CH1 domain and the second polynucleotide encodes a light chain comprising a first CL domain, wherein the first pairing comprises a first antigen binding site; and
   (ii) a third polynucleotide and a fourth polynucleotide encoding a second pairing of the bispecific antibody, wherein the third polynucleotide encodes a heavy chain comprising a second CH1 domain and the fourth polynucleotide encodes a light chain comprising a second CL domain, wherein the second pairing comprises a second antigen binding site, wherein:
   (a) the first CH1 domain and the second CH1 domain are of different human immunoglobulin subtypes selected from the group consisting of IgG1, IgG2, IgG3 and IgG4, or the first CH1 domain and the second CH1 domain—are of different human immunoglobulin allotypes selected from the group consisting of IGGH1.1 (SEQ ID NO: 1), IGGH1.3 (SEQ ID NO: 2), IGGH2 (SEQ ID NO: 3), IGGH2.2 (SEQ ID NO: 4), IGGH2.4 (SEQ ID NO: 5), IGGH4 (SEQ ID NO: 6), IGGH3 (SEQ ID NO: 7), IGG3.17 (SEQ ID NO: 8), and IGGH3.18 (SEQ ID NO: 9),
   (b) the first CL domain is a human lambda light chain and the second CL domain is a human kappa light chain, wherein the human lambda light chain is of a human immunoglobulin allotype selected from the group consisting of IGLC1*01 (SEQ ID NO: 10), IGLC2*01 (SEQ ID NO: 11), IGLC3*01 (SEQ ID NO: 12), IGLC7*01 (SEQ ID NO: 13), and IGLC6*01 (SEQ ID NO: 14), and
   (c) the first CH1 domain and the second CH1 domain differ at one or more positions selected from the group consisting of positions 131, 133, 137, 138, 178, 192, and 193, according to the EU numbering scheme, wherein:
      (i) at position 131: C in the first CH1 domain; S in the second CH1 domain; and/or
      (ii) at position 133: R in the first CH1 domain; K in the second CH1 domain; and/or
      (iii) at position 137: E in the first CH1 domain; Gin the second CH1 domain; and/or
      (iv) at position 138: S in the first CH1 domain; G in the second CH1 domain; and/or
      (v) at position 178: S in the first CH1 domain; Y in the second CH1 domain; and/or
      (vi) at position 192: N in the first CH1 domain; S in the second CH1 domain; and/or
      (vii) at position 193: F in the first CH1 domain; L in the second CH1 domain, in each case according to the EU numbering scheme.

2. The composition of claim 1, wherein the first CH1 domain and the second CH1 domain of the bispecific antibody are of different human immunoglobulin subtypes.

3. The composition of claim 1, wherein the first CH1 domain and the second CH1 domain of the bispecific antibody are of different human immunoglobulin allotypes.

4. The composition of claim 1, wherein the antibody is monovalent.

5. The composition of claim 1, wherein each polynucleotide is comprised within an expression vector.

6. The composition of claim 5, wherein:
   (i) each polynucleotide is comprised within the same expression vector;
   (ii) each polynucleotide is comprised within a separate expression vector;
   (iii) the first polynucleotide and the second polynucleotide are comprised within the same expression vector;
   (iv) the first polynucleotide and the third polynucleotide are comprised within the same expression vector;
   (v) the first polynucleotide and the fourth polynucleotide are comprised within the same expression vector;
   (vi) the second polynucleotide and the third polynucleotide are comprised within the same expression vector;
   (vii) the second polynucleotide and the fourth polynucleotide are comprised within the same expression vector;
   (viii) the third polynucleotide and the fourth polynucleotide are comprised within the same expression vector;
   (ix) the first polynucleotide, the second polynucleotide, and the fourth polynucleotide are comprised within the same expression vector;
   (x) the first polynucleotide, the second polynucleotide, and the third polynucleotide are comprised within the same expression vector;
   (xi) the first polynucleotide, the third polynucleotide, and the fourth polynucleotide are comprised within the same expression vector; or
   (xii) the second polynucleotide, the third polynucleotide, and the fourth polynucleotide are comprised within the same expression vector.

7. A host cell comprising the composition of claim 6.

8. A method of producing a bispecific antibody comprising culturing the host cell of claim 7 so that the polynucleotides are expressed and the bispecific antibody is produced.

9. An isolated polynucleotide encoding a VHH antibody comprising an amino acid sequence selected from the group consisting of SEQ ID NO: 15-18.

10. A host cell comprising the isolated polynucleotide of claim 9.

11. A method of producing a VHH antibody comprising culturing the host cell of claim 10 so that the polynucleotide is expressed and the VHH antibody is produced.

12. A host cell comprising:
(i) a first polynucleotide and a second polynucleotide encoding a first pairing of a bispecific antibody, wherein the first polynucleotide encodes a heavy chain comprising a first CH1 domain and the second polynucleotide encodes a light chain comprising a first CL domain, wherein the first pairing comprises a first antigen binding site; and
(ii) a third polynucleotide and a fourth polynucleotide encoding a second pairing of the bispecific antibody, wherein the third polynucleotide encodes a heavy chain comprising a second CH1 domain and the fourth polynucleotide encodes a light chain comprising a second CL domain, wherein the second pairing comprises a second antigen binding site, wherein:
(a) the first CH1 domain and the second CH1 domain are of different human immunoglobulin subtypes selected from the group consisting of IgG1, IgG2, IgG3 and IgG4, or the first CH1 domain and the second CH1 domain—are of different human immunoglobulin allotypes selected from the group consisting of IGGH1.1 (SEQ ID NO: 1), IGGH1.3 (SEQ ID NO: 2), IGGH2 (SEQ ID NO: 3), IGGH2.2 (SEQ ID NO: 4), IGGH2.4 (SEQ ID NO: 5), IGGH4 (SEQ ID NO: 6), IGGH3 (SEQ ID NO: 7), IGG3.17 (SEQ ID NO: 8), and IGGH3.18 (SEQ ID NO: 9),
(b) the first CL domain is a human lambda light chain and the second CL domain is a human kappa light chain, wherein the human lambda light chain is of a human immunoglobulin allotype selected from the group consisting of IGLC1*01 (SEQ ID NO: 10), IGLC2*01 (SEQ ID NO: 11), IGLC3*01 (SEQ ID NO: 12), IGLC7*01 (SEQ ID NO: 13), and IGLC6*01 (SEQ ID NO: 14), and
(c) the first CH1 domain and the second CH1 domain differ at one or more positions selected from the group consisting of positions 131, 133, 137, 138, 178, 192, and 193, according to the EU numbering scheme, wherein:
(i) at position 131: C in the first CH1 domain; S in the second CH1 domain; and/or
(ii) at position 133: R in the first CH1 domain; K in the second CH1 domain; and/or
(iii) at position 137: E in the first CH1 domain; G in the second CH1 domain; and/or
(iv) at position 138: S in the first CH1 domain; G in the second CH1 domain; and/or
(v) at position 178: S in the first CH1 domain; Y in the second CH1 domain; and/or
(vi) at position 192: N in the first CH1 domain; S in the second CH1 domain; and/or
(vii) at position 193: F in the first CH1 domain; L in the second CH1 domain, in each case according to the EU numbering scheme.

13. The host cell of claim 12, wherein the first CH1 domain and the second CH1 domain of the antibody are of different human immunoglobulin subtypes.

14. The host cell of claim 12, wherein the first CH1 domain and the second CH1 domain of the antibody are of different human immunoglobulin allotypes.

15. The host cell of claim 12, wherein the antibody is monovalent.

16. A method of producing a bispecific antibody comprising culturing the host cell of claim 12 so that the polynucleotides are expressed and the bispecific antibody is produced.

* * * * *